(12) United States Patent
Ma et al.

(10) Patent No.: US 9,193,745 B2
(45) Date of Patent: Nov. 24, 2015

(54) HETEROLEPTIC IRIDIUM COMPLEX

(75) Inventors: Bin Ma, Plainsboro, NJ (US); Zeinab Elshenawy, Holland, PA (US); Chuanjun Xia, Lawrenceville, NJ (US)

(73) Assignee: Universal Display Corporation, Ewing, NJ (US)

( * ) Notice: Subject to any disclaimer, the term of this patent is extended or adjusted under 35 U.S.C. 154(b) by 1015 days.

(21) Appl. No.: 13/296,806

(22) Filed: Nov. 15, 2011

(65) Prior Publication Data

US 2013/0119354 A1    May 16, 2013

(51) Int. Cl.
| | |
|---|---|
| *H01L 51/54* | (2006.01) |
| *C09K 11/06* | (2006.01) |
| *C07F 15/00* | (2006.01) |
| *H01L 51/00* | (2006.01) |
| *H05B 33/10* | (2006.01) |
| *H01L 51/50* | (2006.01) |

(52) U.S. Cl.
CPC ............. *C07F 15/0033* (2013.01); *C09K 11/06* (2013.01); *H01L 51/0085* (2013.01); *H05B 33/10* (2013.01); *C09K 2211/1007* (2013.01); *C09K 2211/1011* (2013.01); *C09K 2211/1029* (2013.01); *C09K 2211/1088* (2013.01); *C09K 2211/1092* (2013.01); *C09K 2211/185* (2013.01); *H01L 51/5016* (2013.01); *Y02E 10/549* (2013.01)

(58) Field of Classification Search
None
See application file for complete search history.

(56) References Cited

U.S. PATENT DOCUMENTS

| | | |
|---|---|---|
| 4,769,292 A | 9/1988 | Tang et al. |
| 5,061,569 A | 10/1991 | VanSlyke et al. |
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |

(Continued)

FOREIGN PATENT DOCUMENTS

| | | |
|---|---|---|
| CN | 101669226 A | 3/2010 |
| EP | 0650955 | 5/1995 |

(Continued)

OTHER PUBLICATIONS

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," *Adv. Mater.*, 6(9):677-679 (1994).

(Continued)

*Primary Examiner* — Marie R. Yamnitzky
(74) *Attorney, Agent, or Firm* — Duane Morris LLP

(57) ABSTRACT

Novel phosphorescent heteroleptic iridium complexes with phenylpyridine and dibenzo-containing ligands are provided. The disclosed compounds have low sublimation temperatures that allow for ease of purification and fabrication into a variety of OLED devices.

25 Claims, 3 Drawing Sheets

Formula I

(56) References Cited

U.S. PATENT DOCUMENTS

| | | | |
|---|---|---|---|
| 6,528,187 | B1 | 3/2003 | Okada |
| 6,687,266 | B1 | 2/2004 | Ma et al. |
| 6,835,469 | B2 | 12/2004 | Kwong et al. |
| 6,893,743 | B2 * | 5/2005 | Sato et al. ............ 428/690 |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,445,855 | B2 | 11/2008 | Mackenzie et al. |
| 7,534,505 | B2 | 5/2009 | Lin et al. |
| 8,709,615 | B2 * | 4/2014 | Kottas et al. ............ 428/690 |
| 8,722,205 | B2 * | 5/2014 | Xia et al. ............ 428/690 |
| 2002/0034656 | A1 | 3/2002 | Thompson et al. |
| 2002/0134984 | A1 | 9/2002 | Igarashi |
| 2002/0158242 | A1 | 10/2002 | Son et al. |
| 2003/0138657 | A1 | 7/2003 | Li et al. |
| 2003/0152802 | A1 | 8/2003 | Tsuboyama et al. |
| 2003/0162053 | A1 | 8/2003 | Marks et al. |
| 2003/0175553 | A1 | 9/2003 | Thompson et al. |
| 2003/0230980 | A1 | 12/2003 | Forrest et al. |
| 2004/0036077 | A1 | 2/2004 | Ise |
| 2004/0137267 | A1 | 7/2004 | Igarashi et al. |
| 2004/0137268 | A1 | 7/2004 | Igarashi et al. |
| 2004/0174116 | A1 | 9/2004 | Lu et al. |
| 2005/0025993 | A1 | 2/2005 | Thompson et al. |
| 2005/0112407 | A1 | 5/2005 | Ogasawara et al. |
| 2005/0238919 | A1 | 10/2005 | Ogasawara |
| 2005/0244673 | A1 | 11/2005 | Satoh et al. |
| 2005/0260441 | A1 | 11/2005 | Thompson et al. |
| 2005/0260449 | A1 | 11/2005 | Walters et al. |
| 2006/0008670 | A1 | 1/2006 | Lin et al. |
| 2006/0202194 | A1 | 9/2006 | Jeong et al. |
| 2006/0240279 | A1 | 10/2006 | Adamovich et al. |
| 2006/0251923 | A1 | 11/2006 | Lin et al. |
| 2006/0263635 | A1 | 11/2006 | Ise |
| 2006/0280965 | A1 | 12/2006 | Kwong et al. |
| 2007/0190359 | A1 | 8/2007 | Knowles et al. |
| 2007/0278938 | A1 | 12/2007 | Yabunouchi et al. |
| 2008/0015355 | A1 | 1/2008 | Schafer et al. |
| 2008/0018221 | A1 | 1/2008 | Egen et al. |
| 2008/0106190 | A1 | 5/2008 | Yabunouchi et al. |
| 2008/0124572 | A1 | 5/2008 | Mizuki et al. |
| 2008/0220265 | A1 | 9/2008 | Xia et al. |
| 2008/0297033 | A1 | 12/2008 | Knowles et al. |
| 2009/0008605 | A1 | 1/2009 | Kawamura et al. |
| 2009/0009065 | A1 | 1/2009 | Nishimura et al. |
| 2009/0017330 | A1 | 1/2009 | Iwakuma et al. |
| 2009/0030202 | A1 | 1/2009 | Iwakuma et al. |
| 2009/0039776 | A1 | 2/2009 | Yamada et al. |
| 2009/0045730 | A1 | 2/2009 | Nishimura et al. |
| 2009/0045731 | A1 | 2/2009 | Nishimura et al. |
| 2009/0101870 | A1 | 4/2009 | Prakash et al. |
| 2009/0108737 | A1 | 4/2009 | Kwong et al. |
| 2009/0115316 | A1 | 5/2009 | Zheng et al. |
| 2009/0165846 | A1 | 7/2009 | Johannes et al. |
| 2009/0167162 | A1 | 7/2009 | Lin et al. |
| 2009/0179554 | A1 | 7/2009 | Kuma et al. |
| 2010/0244004 | A1 * | 9/2010 | Xia et al. ............ 257/40 |

FOREIGN PATENT DOCUMENTS

| | | |
|---|---|---|
| EP | 01238981 | 9/2002 |
| EP | 1725079 | 11/2006 |
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | WO 0139234 | 5/2001 |
| WO | WO 0202714 | 1/2002 |
| WO | WO 0215645 | 2/2002 |
| WO | WO 03040257 | 5/2003 |
| WO | WO 03060956 | 7/2003 |
| WO | WO 2004093207 | 10/2004 |
| WO | WO 2004107822 | 12/2004 |
| WO | WO 2005014551 | 2/2005 |
| WO | WO 2005019373 | 3/2005 |
| WO | WO 2005030900 | 4/2005 |
| WO | WO 2005089025 | 9/2005 |
| WO | WO 2005123873 | 12/2005 |
| WO | WO 2006009024 | 1/2006 |
| WO | WO 2006056418 | 6/2006 |
| WO | WO 2006072002 | 7/2006 |
| WO | WO 2006082742 | 8/2006 |
| WO | WO 2006098120 | 9/2006 |
| WO | WO 2006100298 | 9/2006 |
| WO | WO 2006103874 | 10/2006 |
| WO | WO 2006114966 | 11/2006 |
| WO | WO 2006132173 | 12/2006 |
| WO | WO 2007002683 | 1/2007 |
| WO | WO 2007004380 | 1/2007 |
| WO | WO 2007063754 | 6/2007 |
| WO | WO 2007063796 | 6/2007 |
| WO | WO 2008056746 | 5/2008 |
| WO | WO 2008101842 | 8/2008 |
| WO | WO 2008132085 | 11/2008 |
| WO | WO 2009000673 | 12/2008 |
| WO | WO 2009003898 | 1/2009 |
| WO | WO 2009008311 | 1/2009 |
| WO | WO 2009018009 | 2/2009 |
| WO | WO 2009021126 | 2/2009 |
| WO | WO 2009/030981 A2 * | 3/2009 |
| WO | WO 2009050290 | 4/2009 |
| WO | WO 2009062578 | 5/2009 |
| WO | WO 2009063833 | 5/2009 |
| WO | WO 2009066778 | 5/2009 |
| WO | WO 2009066779 | 5/2009 |
| WO | WO 2009086028 | 7/2009 |
| WO | WO 2009100991 | 8/2009 |
| WO | WO 2010111175 | 9/2010 |

OTHER PUBLICATIONS

Paulose, Betty Marie Jennifer S. et al., "First Examples of Alkenyl Pyridines as Organic Ligands for Phosphorescent Iridium Complexes," *Adv. Mater.*, 16(22):2003-2007 (2004).

Tung, Yung-Liang et al., "Organic Light-Emitting Diodes Based on Charge-Neutral Ru$^{II}$ PHosphorescent Emitters," Adv. Mater., 17(8):1059-1064 (2005).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," *Adv. Mater.*, 19:739-743 (2007).

Wong, Wai-Yeung, "Multifunctional Iridium Complexes Based on Carbazole Modules as Highly Efficient Electrophosphors," *Angew. Chem. Int. Ed.*, 45:7800-7803 (2006).

Tang, C.W. and VanSlyke, S.A., "Organic Electroluminescent Diodes," *Appl. Phys. Lett.*, 51(12):913-915 (1987).

Adachi, Chihaya et al., "Organic Electroluminescent Device Having a Hole Conductor as an Emitting Layer," *Appl. Phys. Lett.*, 55(15):1489-1491 (1989).

Ma, Yuguang et al., "Triplet Luminescent Dinuclear-Gold(I) Complex-Based Light-Emitting Diodes with Low Turn-On voltage," *Appl. Phys. Lett.*, 74(10):1361-1363 (1999).

Gao, Zhiqiang et al., "Bright-Blue Electroluminescence From a Silyl-Substituted ter-(phenylene-vinylene) derivative," *Appl. Phys. Lett.*, 74(6):865-867 (1999).

Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).

Hung, L.S. et al., "Anode Modification in Organic Light-Emitting Diodes by Low-Frequency Plasma Polymerization of CHF$_3$," *Appl. Phys. Lett.*, 78(5):673-675 (2001).

(56) References Cited

OTHER PUBLICATIONS

Ikai, Masamichi et al., "Highly Efficient Phosphorescence From Organic Light-Emitting Devices with an Exciton-Block Layer," *Appl. Phys. Lett.*, 79(2):156-158 (2001).
Wang, Y. et al., "Highly Efficient Electroluminescent Materials Based on Fluorinated Organometallic Iridium Compounds," *Appl. Phys. Lett.*, 79(4):449-451 (2001).
Kwong, Raymond C. et al., "High Operational Stability of Electrophosphorescent Devices," *Appl. Phys. Lett.*, 81(1):162-164 (2002).
Holmes, R.J. et al., "Blue Organic Electrophosphorescence Using Exothermic Host-Guest Energy Transfer," *Appl. Phys. Lett.*, 82(15):2422-2424 (2003).
Sotoyama, Wataru et al., "Efficient Organic Light-Emitting Diodes with Phosphorescent Platinum Complexes Containing N^C^N-Coordinating Tridentate Ligand," *Appl. Phys. Lett.*, 86:153505-1-153505-3 (2005).
Okumoto, Kenji et al., "Green Fluorescent Organic Light-Emitting Device with External Quantum Efficiency of Nearly 10%," *Appl. Phys. Lett.*, 89:063504-1-063504-3 (2006).
Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).
Aonuma, Masaki et al., "Material Design of Hole Transport Materials Capable of Thick-Film Formation in Organic Light Emitting Diodes," *Appl. Phys. Lett.*, 90:183503-1-183503-3 (2007).
Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).
Adachi, Chihaya et al., "High-Efficiency Red Electrophosphorescence Devices," *Appl. Phys. Lett.*, 78(11):1622-1624 (2001).
Wong, Keith Man-Chung et al., "A Novel Class of Phosphorescent Gold(III) Alkynyl-Based Organic Light-Emitting Devices with Tunable Colour," *Chem. Commun.*, 2906-2908 (2005).
Hamada, Yuji et al., "High Luminance in Organic Electroluminescent Devices with Bis(10-hydroxybenzo[h]quinolinato)beryllium as an Emitter," Chem. Lett., 905-906 (1993).
Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).
Mi, Bao-Xiu et al., "Thermally Stable Hole-Transporting Material for Organic Light-Emitting Diode: an Isoindole Derivative," *Chem. Mater.*, 15(16):3148-3151 (2003).
Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).
Niu, Yu-Hua et al., "Highly Efficient Electrophosphorescent Devices with Saturated Red Emission from a Neutral Osmium Complex," *Chem. Mater.*, 17(13):3532-3536 (2005).
Lo, Shih-Chun et al., "Blue Phosphorescence from Iridium(III) Complexes at Room Temperature," *Chem. Mater.*, 18(21):5119-5129 (2006).
Takizawa, Shin-ya et al., "Phosphorescent Iridium Complexes Based on 2-Phenylimidazo[1,2-α]pyridine Ligands: Tuning of Emission Color toward the Blue Region and Application to Polymer Light-Emitting Devices," *Inorg. Chem.*, 46(10):4308-4319 (2007).

Lamansky, Sergey et al., "Synthesis and Characterization of Phosphorescent Cyclometalated Iridium Complexes," *Inorg. Chem.*, 40(7):1704-1711 (2001).
Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).
Noda, Tetsuya and Shirota,Yasuhiko, "5,5'-Bis(dimesitylboryl)-2,2'-bithiophene and 5,5''-Bis(dimesitylboryl)-2,2':5',2''-terthiophene as a Novel Family of Electron-Transporting Amorphous Molecular Materials," *J. Am. Chem. Soc.*, 120 (37):9714-9715 (1998).
Sakamoto,Youichi et al., "Synthesis, Characterization, and Electron-Transport Property of Perfluorinated Phenylene Dendrimers," *J. Am. Chem. Soc.*, 122(8):1832-1833 (2000).
Adachi, Chihaya et al., "Nearly 100% Internal Phosphorescence Efficiency in an Organic Light Emitting Device," *J. Appl. Phys.*, 90(10):5048-5051 (2001).
Shirota, Yasuhiko et al., "Starburst Molecules Based on π-Electron Systems as Materials for Organic Electroluminescent Devices," *Journal of Luminescence*, 72-74:985-991 (1997).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).
Kido, Junji et al.,"1,2,4-Triazole Derivative as an Electron Transport Layer in Organic Electroluminescent Devices," *Jpn. J. Appl. Phys.*, 32:L917-L920 (1993).
Van Slyke, S. A. et al., "Organic Electroluminescent Devices with Improved Stability," *Appl. Phys. Lett.*, 69(15):2160-2162 (1996).
Guo, Tzung-Fang et al., "Highly Efficient Electrophosphorescent Polymer Light-Emitting Devices," *Organic Electronics*, 1:15-20 (2000).
Palilis, Leonidas C., "High Efficiency Molecular Organic Light-Emitting Diodes Based on Silole Derivatives and Their Exciplexes," *Organic Electronics*, 4:113-121 (2003).
Ikeda, Hisao et al., "P-185: Low-Drive-Voltage OLEDs with a Buffer Layer Having Molybdenum Oxide," *SID Symposium Digest*, 37:923-926 (2006).
T. Östergård et al., "Langmuir-Blodgett Light-Emitting Diodes Of Poly(3-Hexylthiophene): Electro-Optical Characteristics Related to Structure," *Synthetic Metals*, 87:171-177 (1997).
Hu, Nan-Xing et al., "Novel High $T_g$ Hole-Transport Molecules Based on Indolo[3,2-b]carbazoles for Organic Light-Emitting Devices," Synthetic Metals, 111-112:421-424 (2000).
Salbeck, J. et al., "Low Molecular Organic Glasses for Blue Electroluminescence," *Synthetic Metals*, 91:209-215 (1997).
Baldo et al., "Very high-efficiency green organic light-emitting devices based on electrophosphorescence," Appl. Phys. Lett., vol. 75, No. 1, 4-6 (1999).
Baldo et al., "Highly Efficient Phosphorescent Emission from Organic Electroluminescent Devices," Nature, vol. 395, 151-154, (1998).
The U.S. Appl. No. 13/193,221, filed Jul. 28, 2011.
Chinese Patent Office, Notification of the First Office Action and English Version of Chinese Office Action regarding corresponding Chinese Application No. 201210478614.1 issued Apr. 21, 2015, pp. 1-13.
Chinese Patent Office, International Search Report regarding corresponding Chinese Application No. 201210478614.1 issued Apr. 21, 2015, pp. 1-4.

* cited by examiner

Formula I

HETEROLEPTIC IRIDIUM COMPLEX

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to heteroleptic iridium complexes, and in particular to complexes containing phenylpyridine and dibenzo ligands. The complexes are suitable for use in OLED devices.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

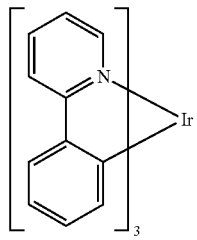

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A compound having the formula:

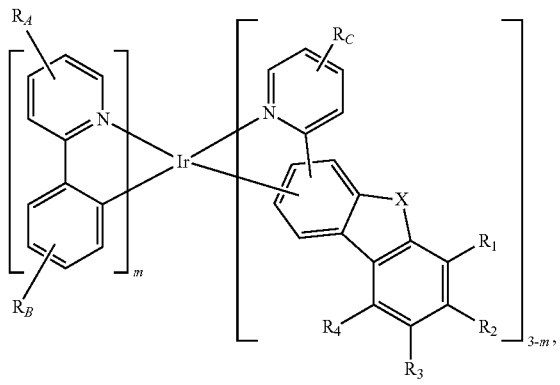

Formula I, is provided. In the compound of Formula I $R_1$, $R_2$, $R_3$, $R_4$, $R_A$, $R_B$, and $R_C$, are independently selected from the group consisting of hydrogen, deuterium, alkyl, cycloalkyl, aryl, heteroaryl, and combinations thereof. $R_A$, $R_B$, and $R_C$ may represent mono, di, tri, or tetra substitutions and at least one of $R_1$, $R_2$, $R_3$, and $R_4$ is not hydrogen or deuterium. Two adjacent substituents $R_1$, $R_2$, $R_3$, $R_4$, $R_A$, $R_B$, and $R_C$ are optionally joined to form a fused ring. X is selected from the group consisting of O, S, and Se, and m is 1 or 2.

In one aspect, $R_1$ is alkyl. In one aspect, $R_C$ and $R_1$ are alkyl. In one aspect, $R_1$ and $R_3$ are alkyl. In one aspect, $R_C$ and $R_3$ are alkyl. In one aspect, X is O. In one aspect, $R_A$ and $R_B$ are hydrogen. In one aspect, m is 2. In another aspect, $R_C$ represents mono-alkyl substitution and $R_C$ is para to N.

In one aspect, $R_1$, $R_2$, $R_3$, and $R_4$ are independently selected from the group consisting of methyl, $CH(CH_3)_2$, and phenyl. In one aspect $R_1$, $R_2$, $R_3$, and $R_4$ are independently selected from the group consisting of alkyl, hydrogen, and deuterium.

In another aspect, the compound has a sublimation temperature from about 180° C. to about 240° C. at pressure ranging from $10^{-7}$ to $10^{-8}$ torr.

In one aspect, the compound has the formula:

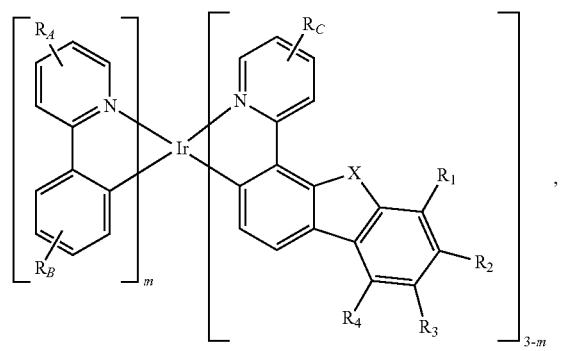

Formula II.

In one aspect, the compound is selected from the group consisting of Compound 1-Compound 63.

In one aspect, a first device is provided. The device comprises a first organic light emitting device, further comprising an anode, a cathode, and an organic layer, disposed between the anode and the cathode, comprising a compound having the formula:

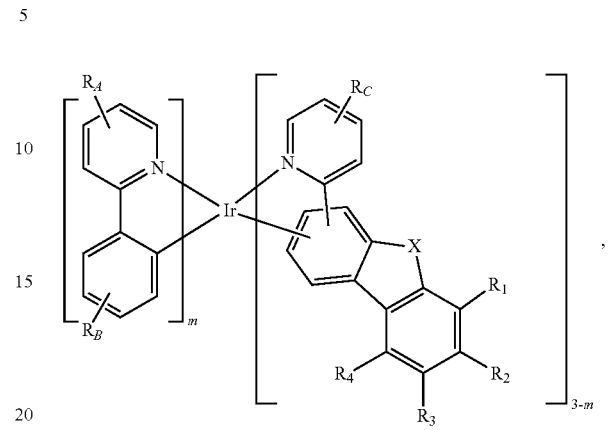

Formula I. In the compound of Formula I $R_1$, $R_2$, $R_3$, $R_4$, $R_A$, $R_B$, and $R_C$, are independently selected from the group consisting of hydrogen, deuterium, alkyl, cycloalkyl, aryl, heteroaryl, and combinations thereof. $R_A$, $R_B$, and $R_C$ may represent mono, di, tri, or tetra substitutions and at least one of $R_1$, $R_2$, $R_3$, and $R_4$ is not hydrogen or deuterium. Two adjacent substituents $R_1$, $R_2$, $R_3$, $R_4$, $R_A$, $R_B$, and $R_C$ are optionally joined to form a fused ring. X is selected from the group consisting of O, S, and Se, and m is 1 or 2.

In one aspect, the first device is a consumer product. In another aspect, the first device is an organic light-emitting device. In one aspect, the first device comprises a lighting panel.

In one aspect, the organic layer is an emissive layer and the compound is a non-emissive dopant. In one aspect, the organic layer further comprises a host.

In one aspect, the host comprises a triphenylene containing benzo-fused thiophene or benzo-fused furan, wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CC_nH_{2n+1}$, $Ar_1$, $Ar_1-Ar_2$, $C_nH_{2n}-Ar_1$, or no substitution. $Ar_1$ and $Ar_2$ are independently selected from the group consisting of benzene, biphenyl, naphthalene, triphenylene, carbazole, and heteroaromatic analogs thereof, and n is from 1 to 10.

In one aspect, the host has the formula:

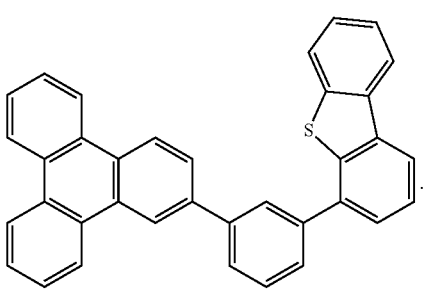

In one aspect, the host is selected from the group consisting of:

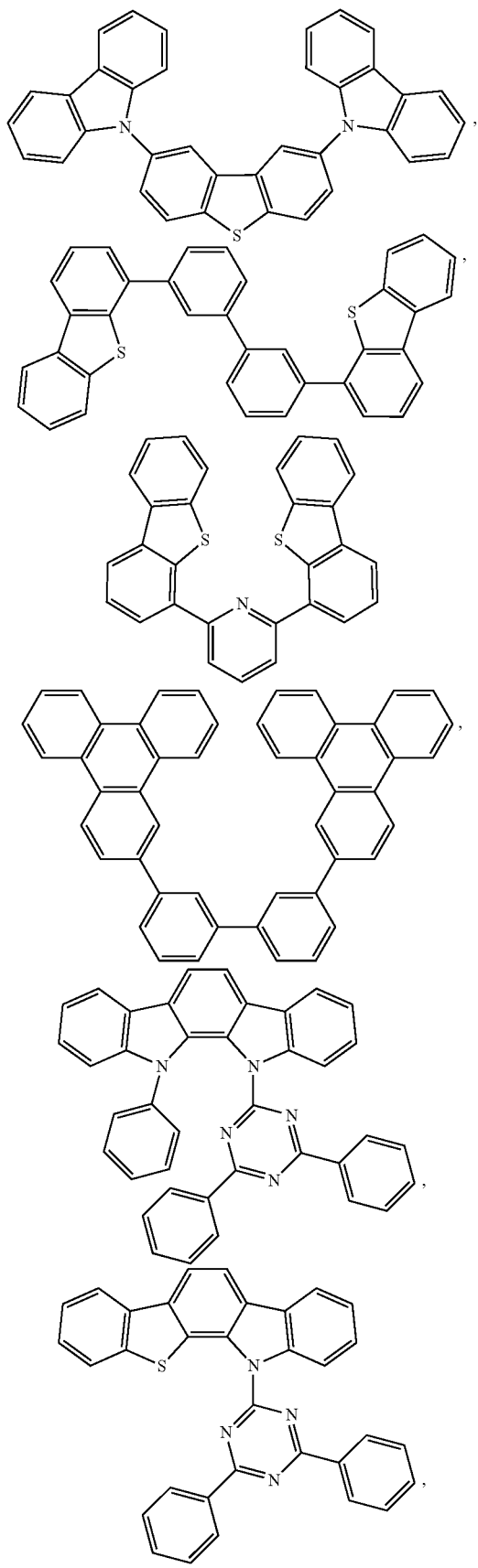

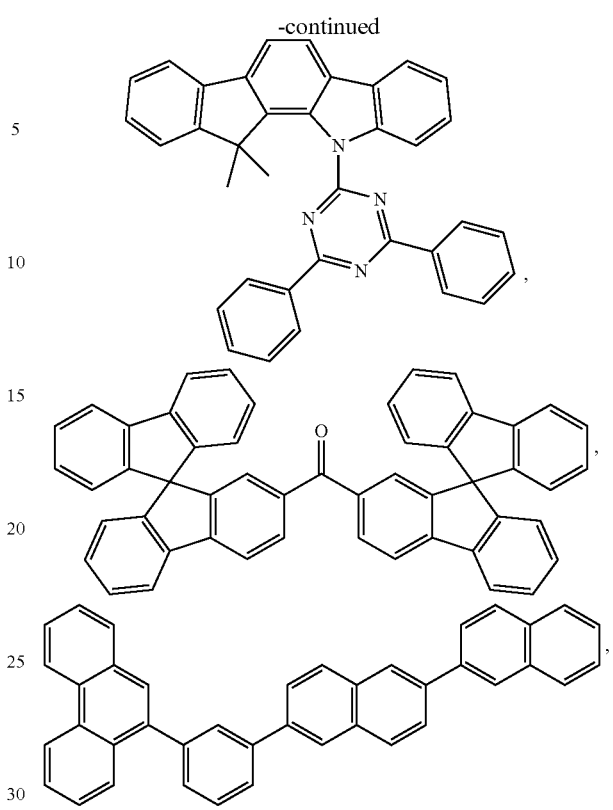

and combinations thereof.

In one aspect, the host is a metal complex.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
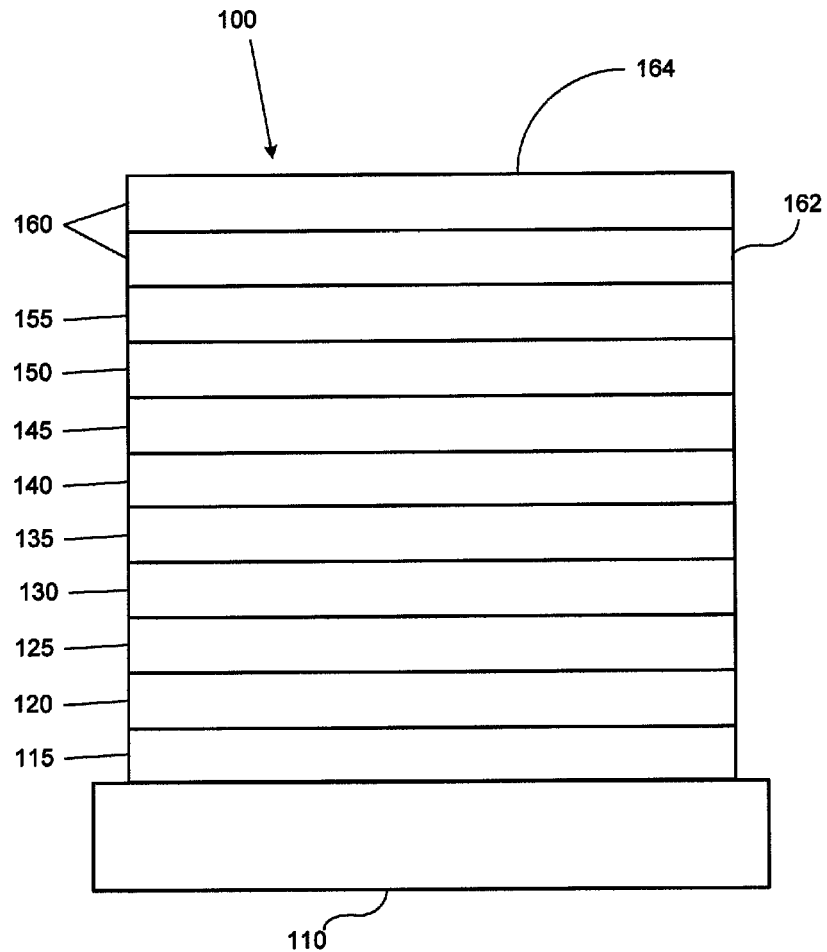
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
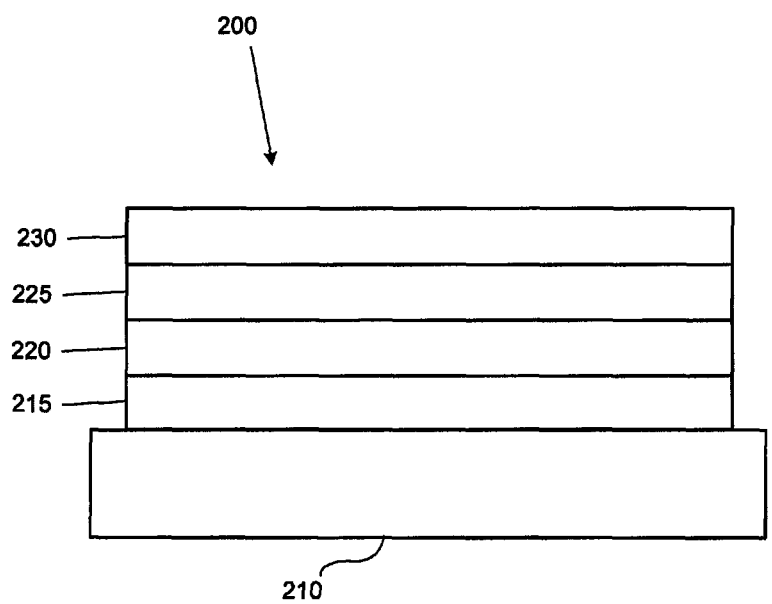
FIG. 2 shows an inverted organic light emitting device that does not have a separate electron transport layer.
Figure 3:
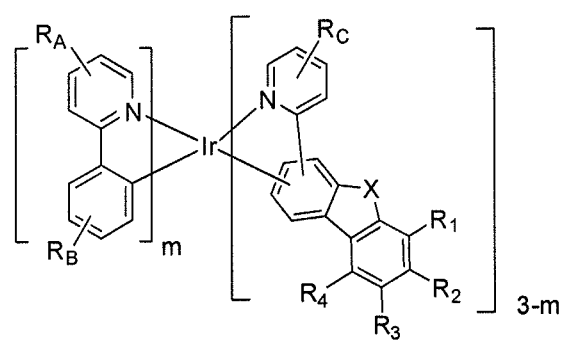
FIG. 3 shows a compound of Formula I.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

A compound having the formula:

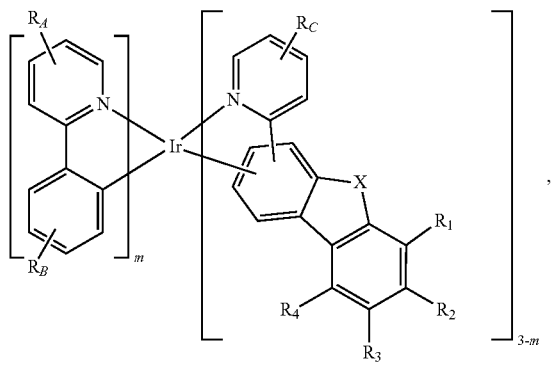

Formula I, is provided. In the compound of Formula I $R_1$, $R_2$, $R_3$, $R_4$, $R_A$, $R_B$, and $R_C$, are independently selected from the group consisting of hydrogen, deuterium, alkyl, cycloalkyl, aryl, heteroaryl, and combinations thereof. $R_A$, $R_B$, and $R_C$ may represent mono, di, tri, or tetra substitutions and at least one of $R_1$, $R_2$, $R_3$, and $R_4$ is not hydrogen or deuterium. Two adjacent substituents $R_1$, $R_2$, $R_3$, $R_4$, $R_A$, $R_B$, and $R_C$ are optionally joined to form a fused ring. X is selected from the group consisting of O, S, and Se, and m is 1 or 2.

It has been unexpectedly discovered that alkyl substitution at one or more of positions $R_1$ through $R_4$ results in compounds of Formula I with desirable properties. These properties enable OLED devices that incorporate compounds of Formula I to have improved properties such as higher efficiency and longer lifetime. Alkyl substitution at one or more of positions $R_1$ through $R_4$ also results in compounds with lowered sublimation temperatures despite the fact that these compounds have higher molecular weights than compounds with all hydrogen substitution at $R_1$ through $R_4$. Without being bound by theory, it is believed that this decrease in sublimation temperature may be the result of decreased or less efficient molecular stacking in the solid state, thereby decreasing the energy required to disrupt the crystal lattice and resulting in decreased sublimation temperatures. Lower sublimation temperatures advantageously allow for easier purification of compounds of Formula I and better thermal stability in manufacturing.

In another embodiment, the compound has a sublimation temperature from about 180° C. to about 240° C. at pressure ranging from $10^{-7}$ to $10^{-8}$ torr.

In one embodiment, $R_1$ is alkyl. In one embodiment, $R_C$ and $R_1$ are alkyl. In one embodiment, $R_1$ and $R_3$ are alkyl. In one embodiment, $R_C$ and $R_3$ are alkyl. In one embodiment, X is O. In one embodiment, $R_A$ and $R_B$ are hydrogen. In one embodiment, m is 2. In another embodiment, $R_C$ represents mono-alkyl substitution and $R_C$ is para to N.

In one embodiment, $R_1$, $R_2$, $R_3$, and $R_4$ are independently selected from the group consisting of methyl, $CH(CH_3)_2$, and phenyl. In one embodiment $R_1$, $R_2$, $R_3$, and $R_4$ are independently selected from the group consisting of alkyl, hydrogen, and deuterium.

In one embodiment, the compound has the formula:

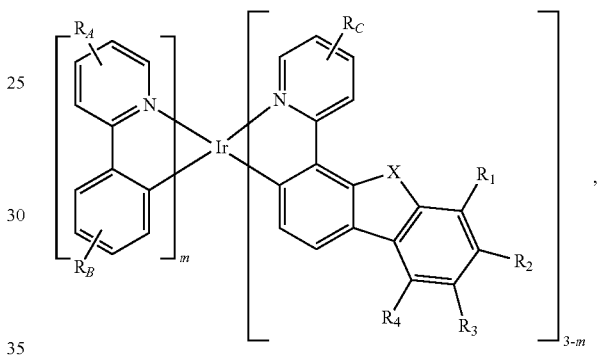

Formula II.

In one embodiment, the compound is selected from the group consisting of:

Compound 1

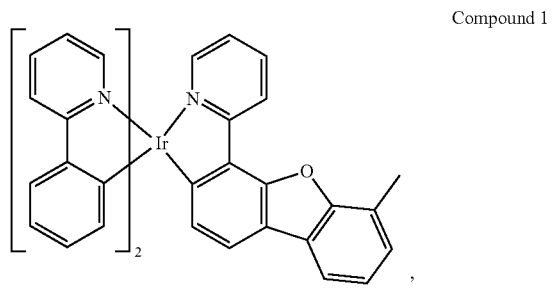

,

Compound 2

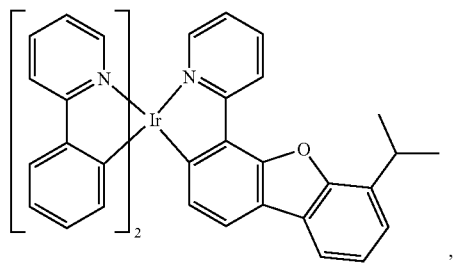

,

Compound 3
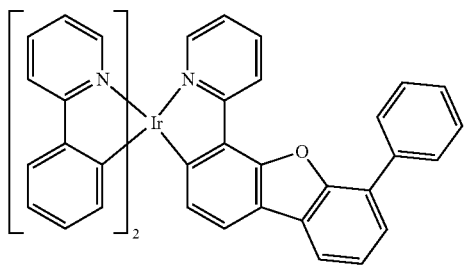
Compound 4
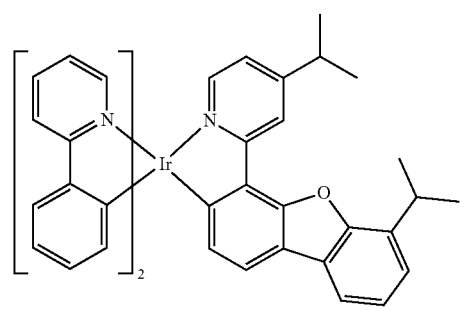
Compound 5
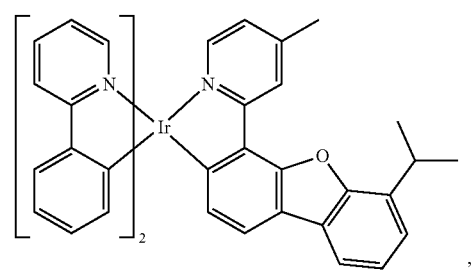
Compound 6
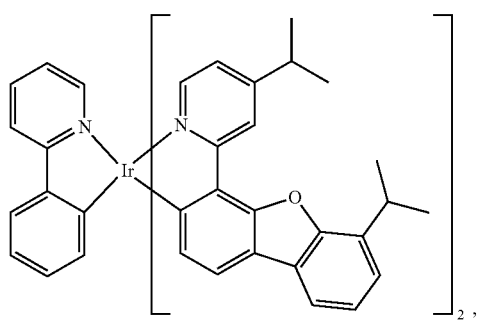
Compound 7
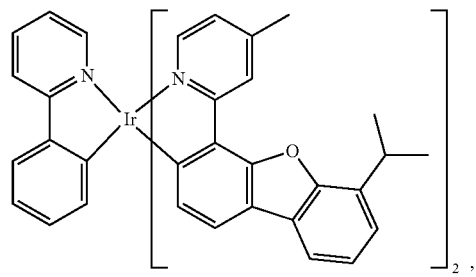
Compound 8
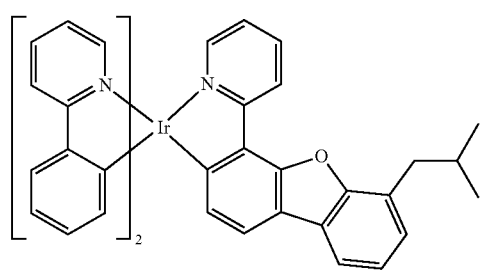
Compound 9
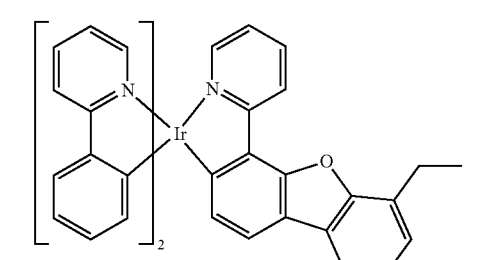
Compound 10
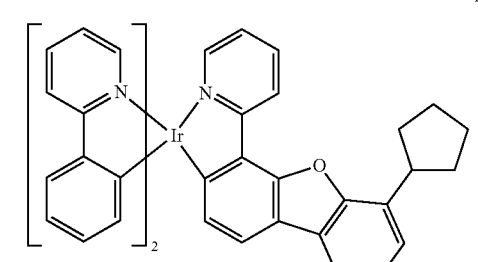
Compound 11
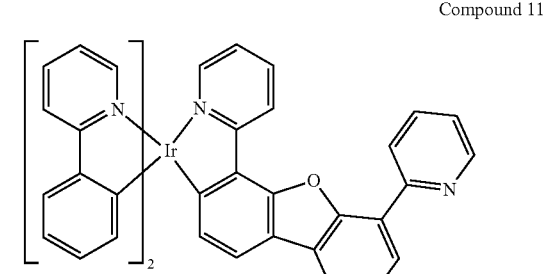
Compound 12
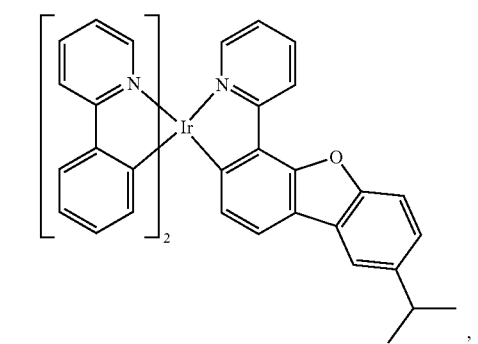

Compound 13
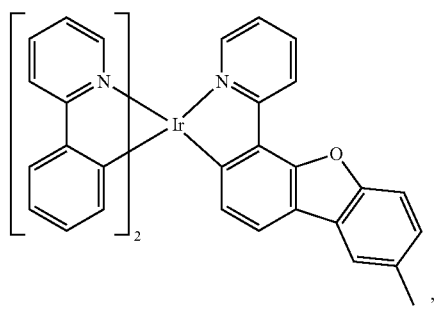
Compound 14
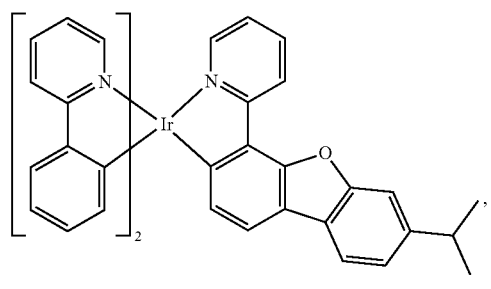
Compound 15
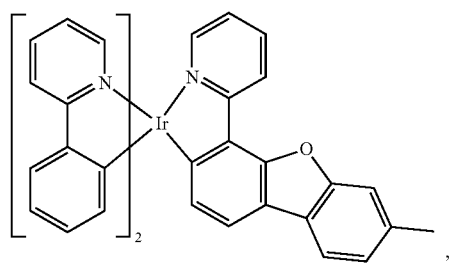
Compound 16
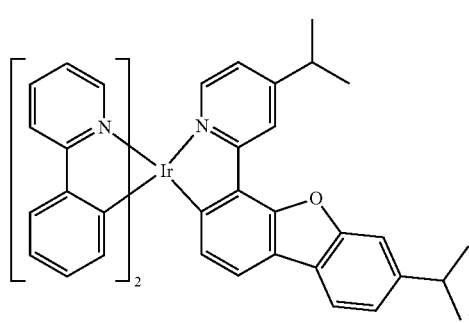
Compound 17
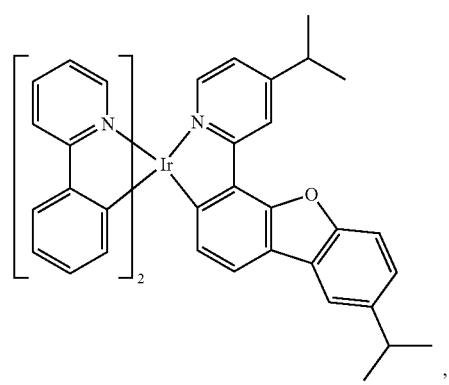
Compound 18
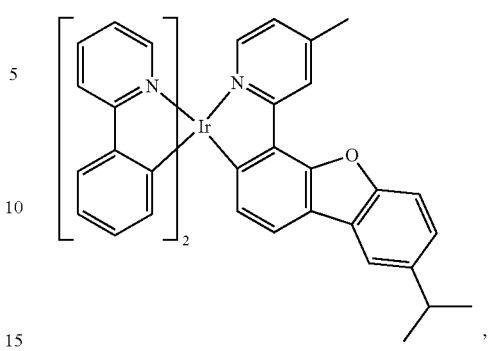
Compound 19
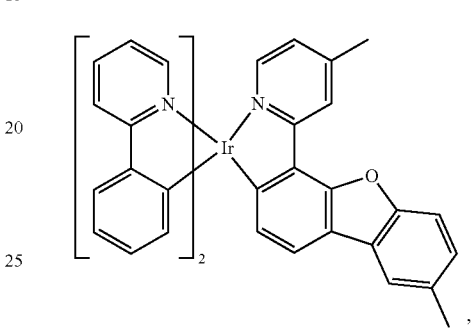
Compound 20
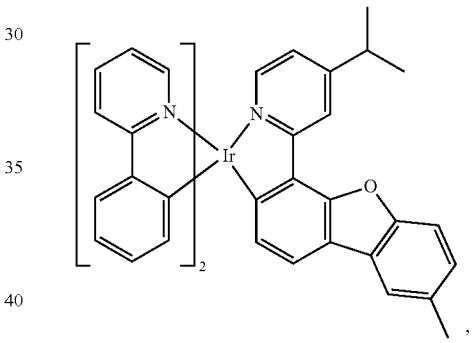
Compound 21
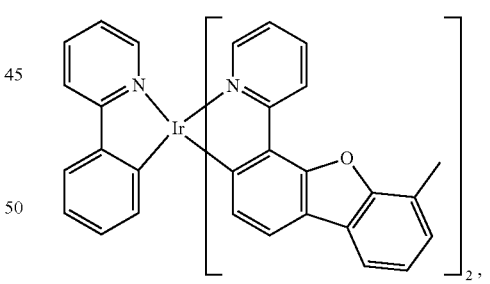
Compound 22
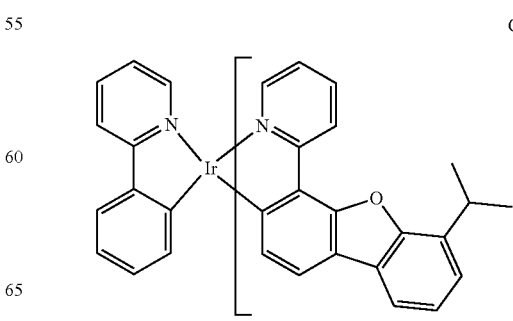

-continued
Compound 23
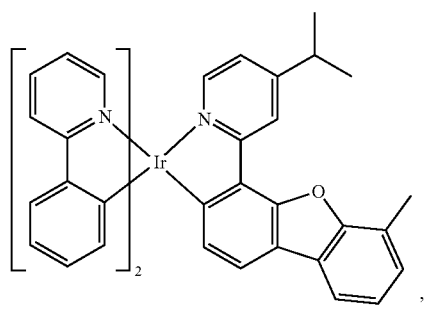
Compound 24
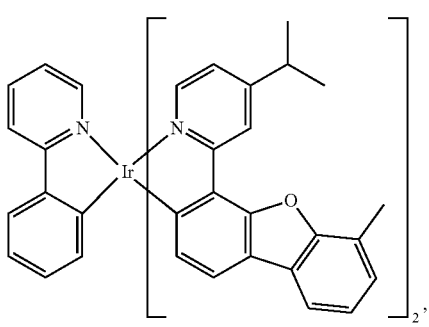
Compound 25
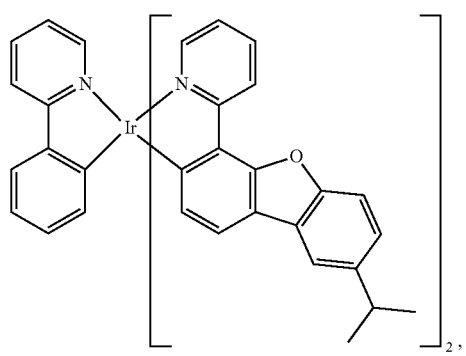
Compound 26
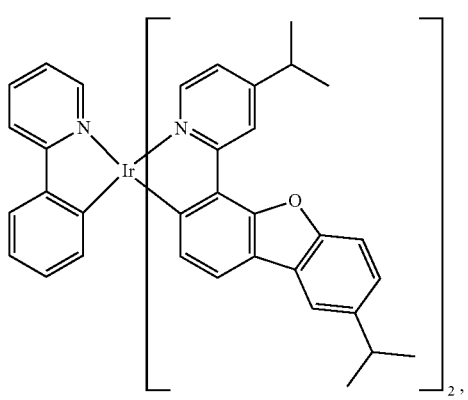
Compound 27
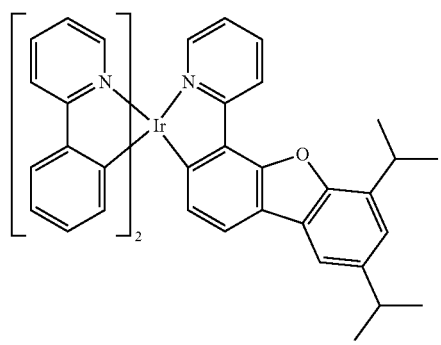
Compound 28
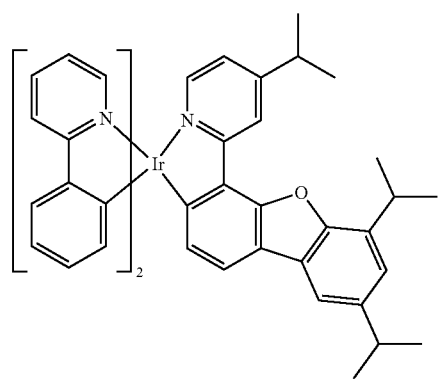
Compound 29
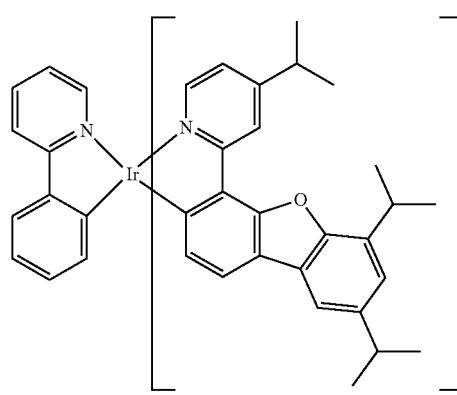
Compound 30
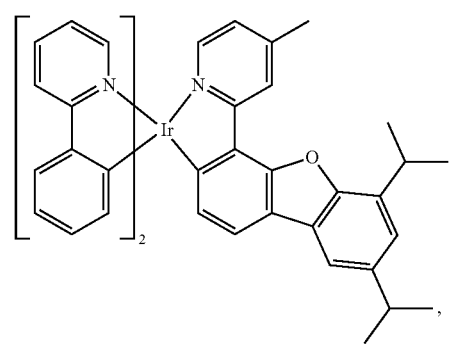

Compound 31
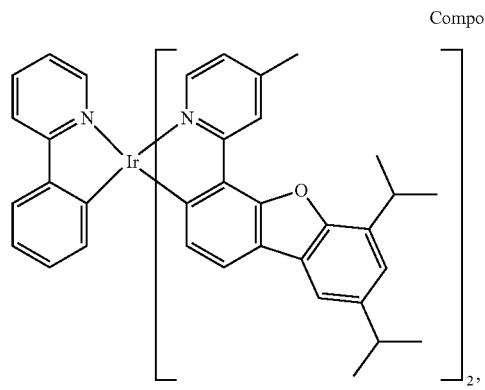
Compound 32
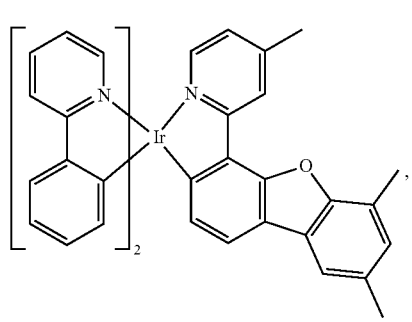
Compound 33
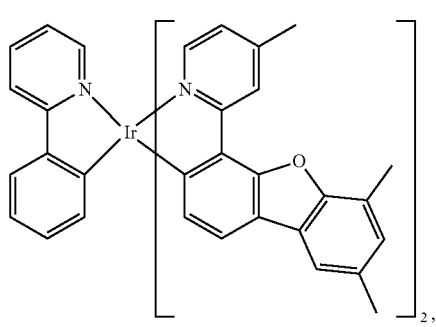
Compound 34
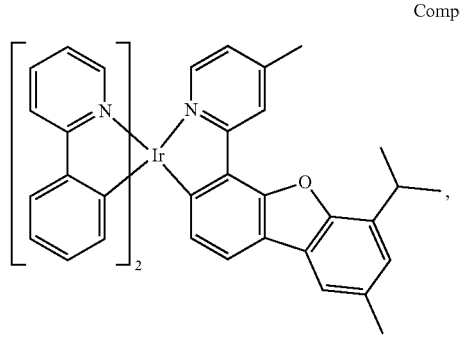
Compound 35
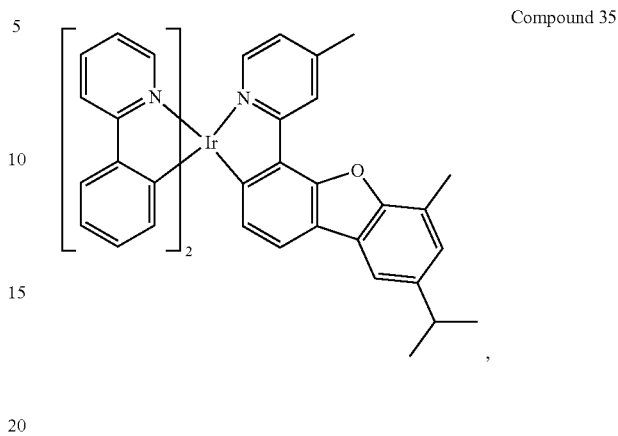
Compound 36
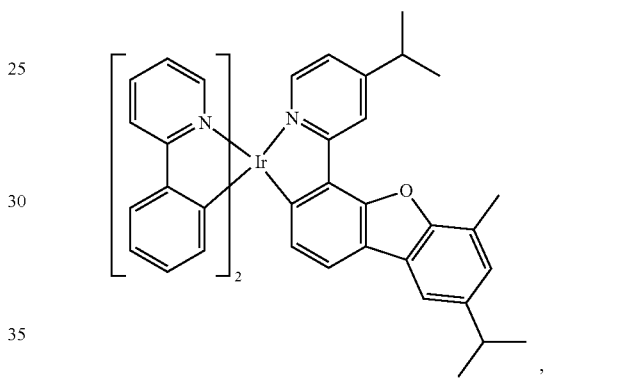
Compound 37
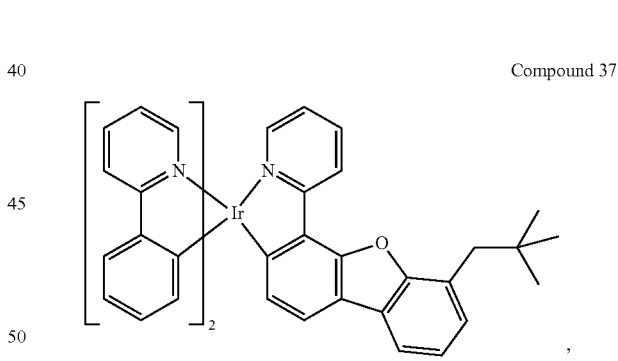
Compound 38
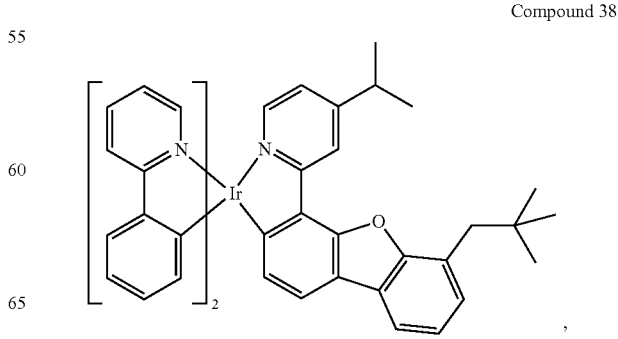

Compound 39
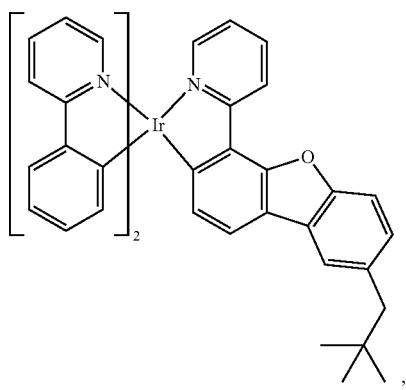
Compound 40
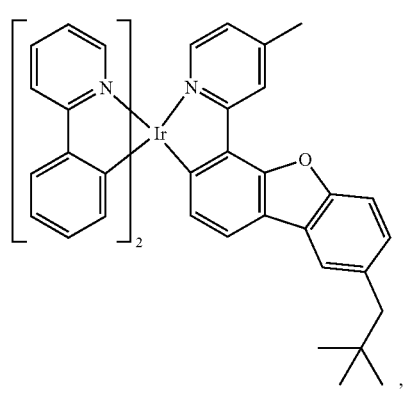
Compound 41
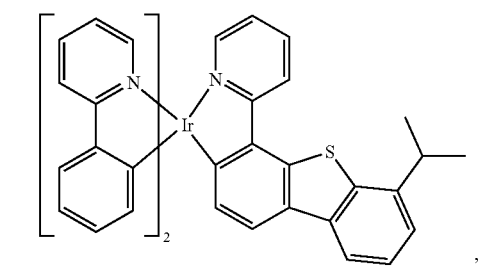
Compound 42
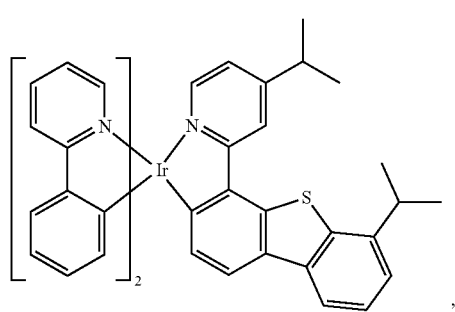
Compound 43
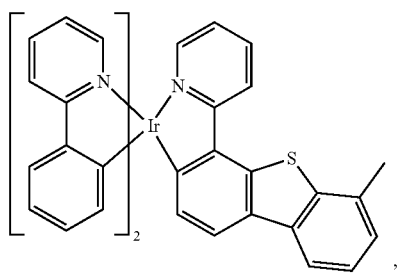
Compound 44
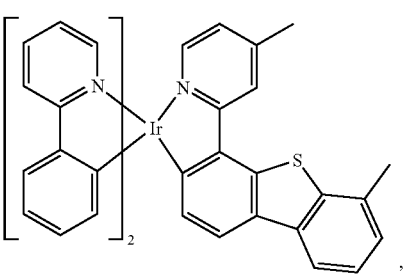
Compound 45
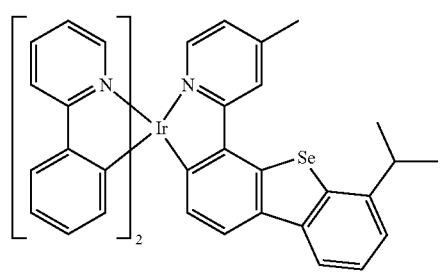
Compound 46
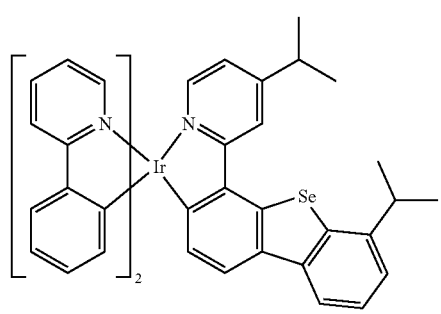
Compound 47
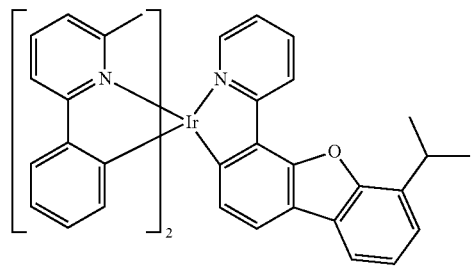

Compound 48
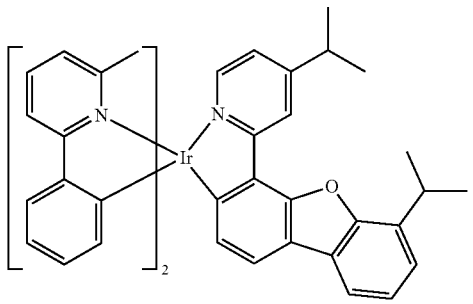
Compound 49
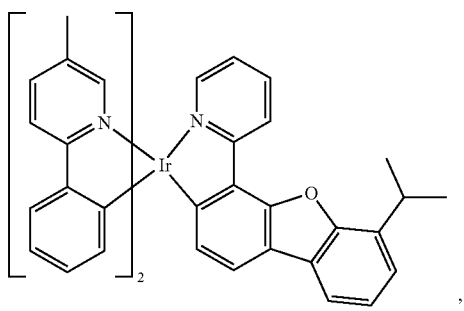
Compound 50
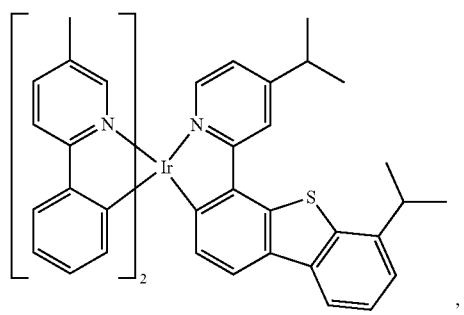
Compound 51
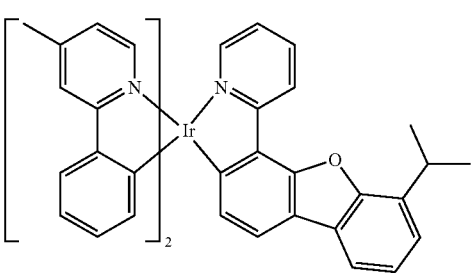
Compound 52
Compound 53
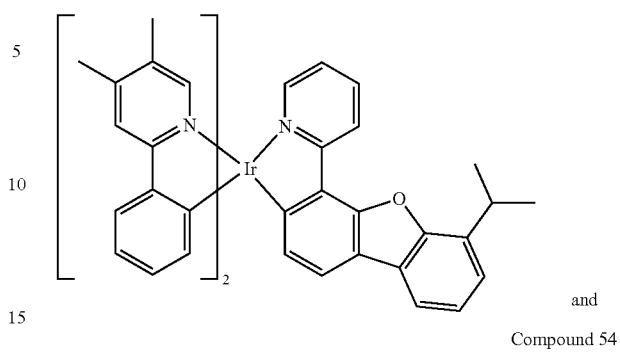
and
Compound 54
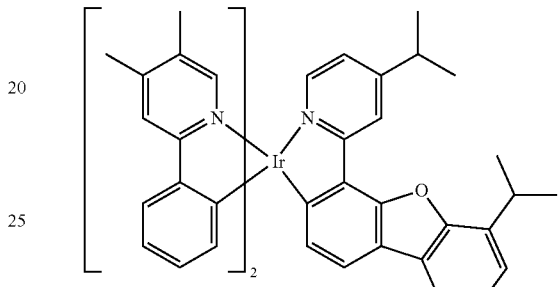
In one embodiment, the compound is selected from the group consisting of:
Compound 55
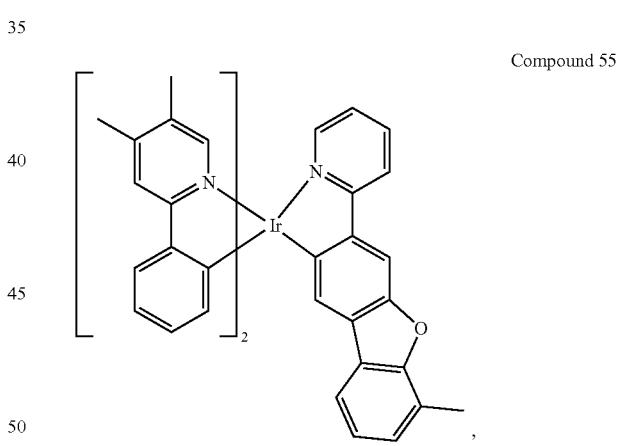
Compound 56
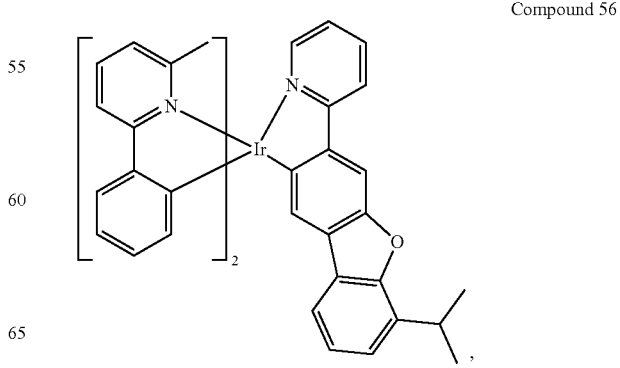

Compound 57
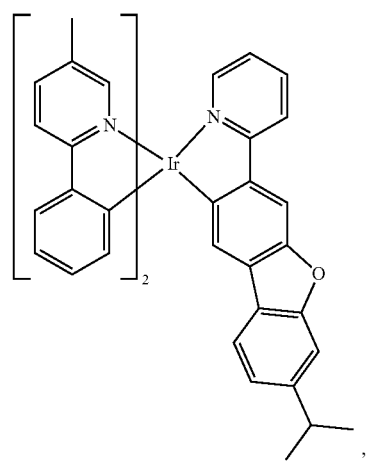
Compound 58
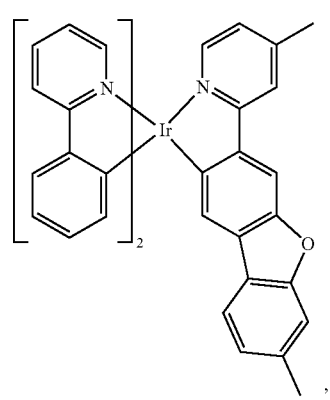
Compound 59
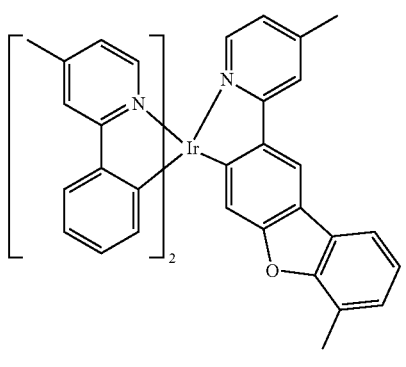
Compound 60
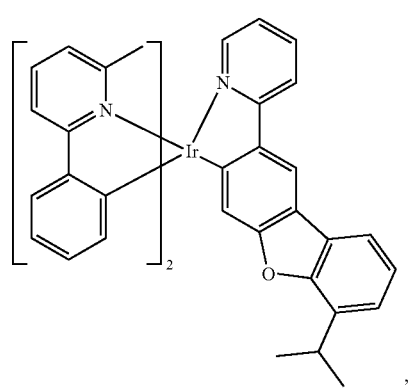
Compound 61
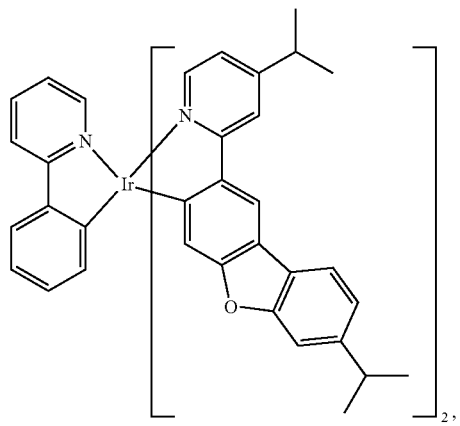
Compound 62
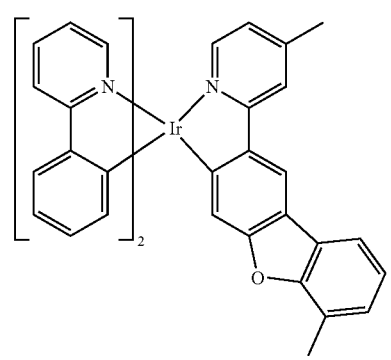
, and
Compound 63
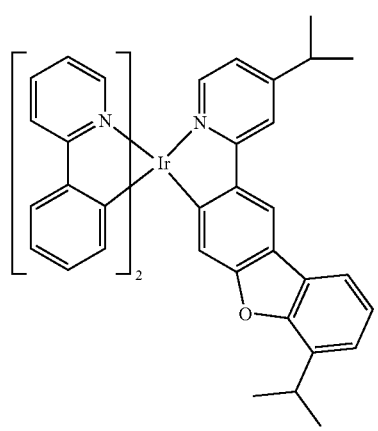
In one embodiment, a first device is provided. The device comprises a first organic light emitting device, further comprising an anode, a cathode, and an organic layer, disposed between the anode and the cathode, comprising a compound having the formula:

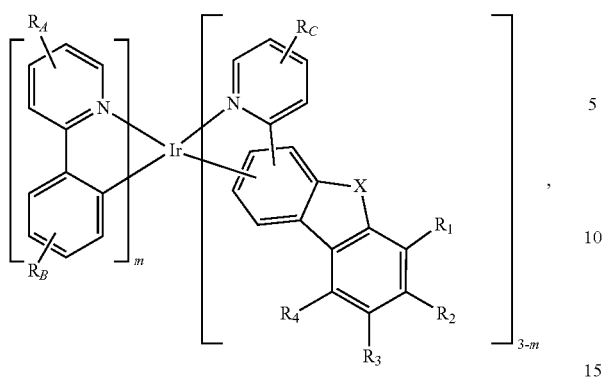

Formula I. In the compound of Formula I $R_1$, $R_2$, $R_3$, $R_4$, $R_A$, $R_B$, and $R_C$, are independently selected from the group consisting of hydrogen, deuterium, alkyl, cycloalkyl, aryl, heteroaryl, and combinations thereof. $R_A$, $R_B$, and $R_C$ may represent mono, di, tri, or tetra substitutions and at least one of $R_1$, $R_2$, $R_3$, and $R_4$ is not hydrogen or deuterium. Two adjacent substituents $R_1$, $R_2$, $R_3$, $R_4$, $R_A$, $R_B$, and $R_C$ are optionally joined to form a fused ring. X is selected from the group consisting of O, S, and Se, and m is 1 or 2.

In one embodiment, the first device is a consumer product. In another embodiment, the first device is an organic light-emitting device. In one aspect, the first device comprises a lighting panel.

In one embodiment, the organic layer is an emissive layer and the compound is a non-emissive dopant. In one embodiment, the organic layer further comprises a host.

In one embodiment, the host comprises a triphenylene containing benzo-fused thiophene or benzo-fused furan, wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CC_nH_{2n+1}$, $Ar_1$, $Ar_1-Ar_2$, $C_nH_{2n}-Ar_1$, or no substitution. $Ar_1$ and $Ar_2$ are independently selected from the group consisting of benzene, biphenyl, naphthalene, triphenylene, carbazole, and heteroaromatic analogs thereof, and n is from 1 to 10.

In one embodiment, the host has the formula:

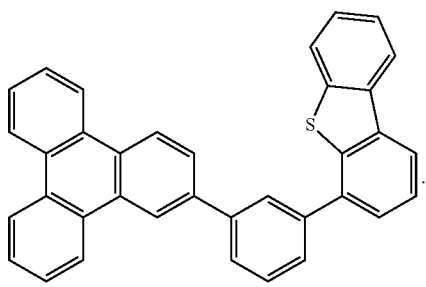 [SMILES: c1cc(-c2ccc3c4ccccc4c4ccccc4c3c2)cc(-c2cccc3c2sc2ccccc23)c1]

In one embodiment, the host is selected from the group consisting of:

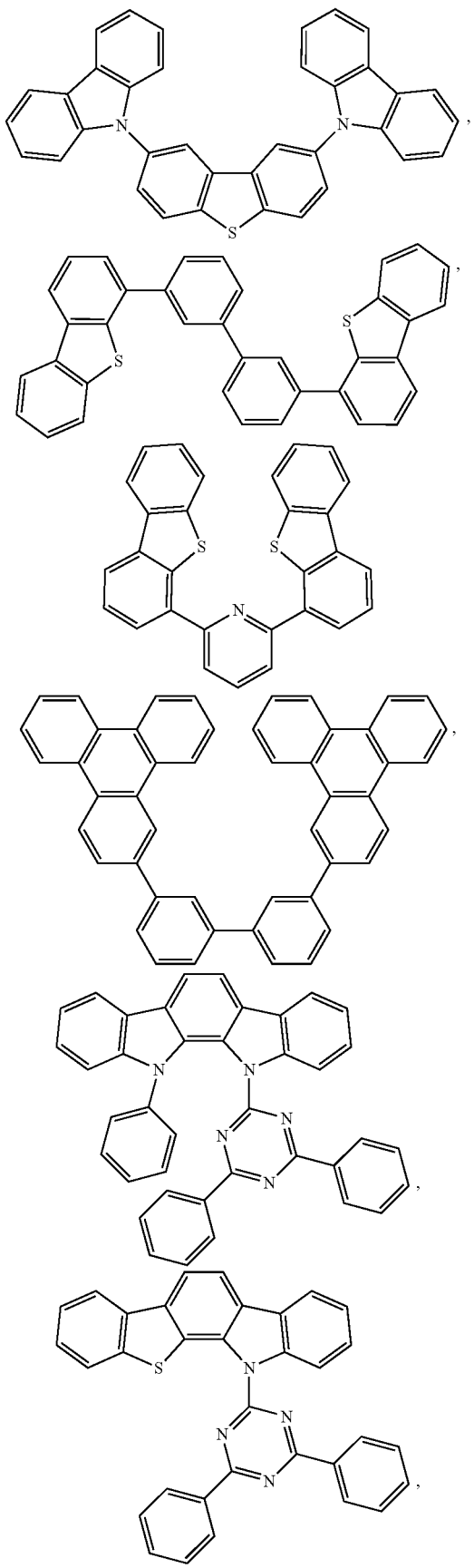

-continued

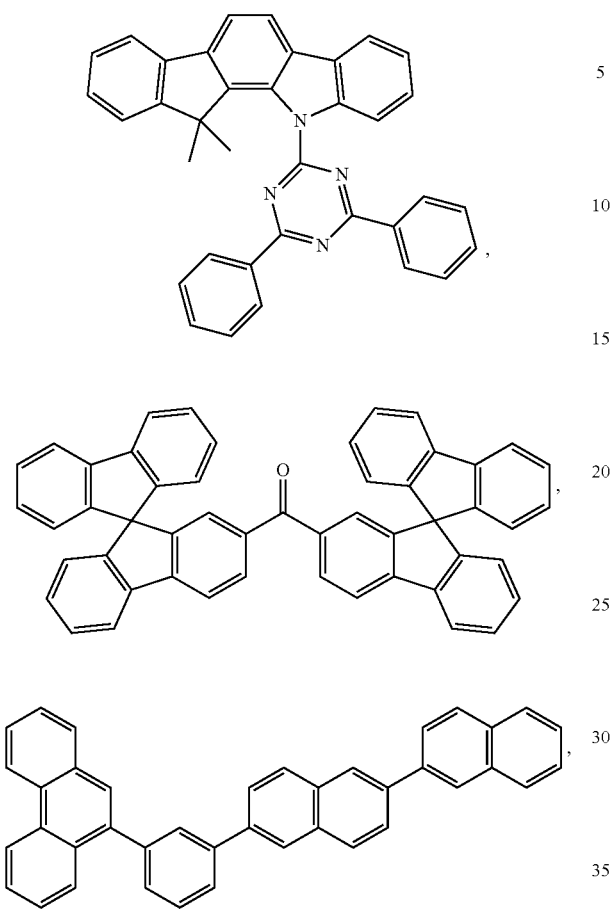

and combinations thereof.

In one aspect, the host is a metal complex.

Device Examples

All example devices were fabricated by high vacuum (<10$^{-7}$ Torr) thermal evaporation. The anode electrode is 1200 Å of indium tin oxide (ITO). The cathode consisted of 10 Å of LiF followed by 1,000 Å of Al. All devices are encapsulated with a glass lid sealed with an epoxy resin in a nitrogen glove box (<1 ppm of H$_2$O and O$_2$) immediately after fabrication, and a moisture getter was incorporated inside the package.

The organic stack of the device examples consisted of sequentially, from the ITO surface, 100 Å of Compound B or C as the hole injection layer (HIL), 300 Å of 4,4'-bis[N-(1-naphthyl)-N-phenylamino]biphenyl (NPD) as the hole transporting layer (HTL), 300 Å of the invention compound doped in compound D as host with 7, 10, 13 wt % of an Ir phosphorescent compound as the emissive layer (EML), 50 Å of the compound D as block layer (BL), 450 Å of Alq$_3$ (tris-8-hydroxyquinoline aluminum) as the ETL. Comparative Examples with compound A and B were fabricated similarly to the Device Examples except that the compound A or B is used as the emitter in the EML.

The device structure and data are summarized in Table 1, Table 2 and Table 3 from those devices. As used herein, Compounds A, B, C, D have the following structures:

Compound A
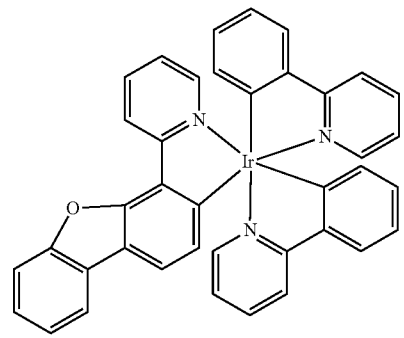

Compound B
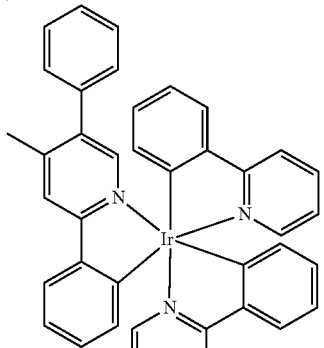

Compound C
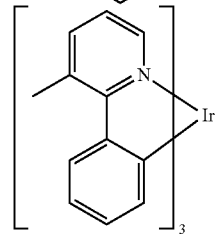

Compound D
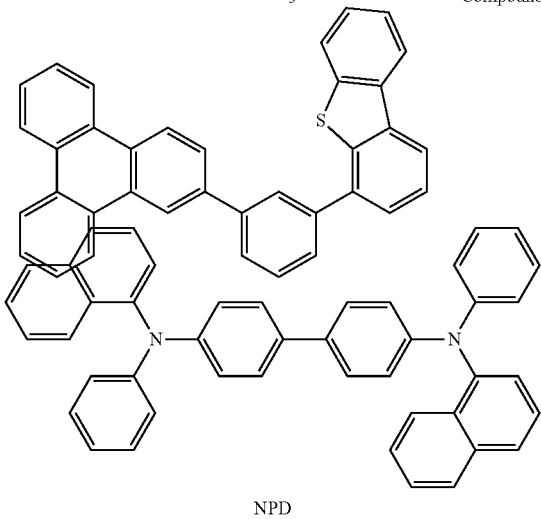

NPD

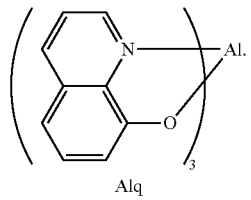

Alq

TABLE 1

Device Structures of Invention Compounds and Comparative Compound A and B

| Example | HIL | HTL | EML (300 Å, doping %) | | BL | ETL |
|---|---|---|---|---|---|---|
| Comparative Example 1 | Compound C 100 Å | NPD 300 Å | Compound D | Compound A 7% | Compound D 50 Å | Alq 450 Å |
| Comparative Example 2 | Compound C 100 Å | NPD 300 Å | Compound D | Compound A 10% | Compound D 50 Å | Alq 450 Å |
| Comparative Example 3 | Compound C 100 Å | NPD 300 Å | Compound D | Compound A 13% | Compound D 50 Å | Alq 450 Å |
| Comparative Example 4 | Compound B 100 Å | NPD 300 Å | Compound D | Compound B 10% | Compound D 50 Å | Alq 450 Å |
| Example 1 | Compound C 100 Å | NPD 300 Å | Compound D | Compound 2 7% | Compound D 50 Å | Alq 450 Å |
| Example 2 | Compound C 100 Å | NPD 300 Å | Compound D | Compound 2 10% | Compound D 50 Å | Alq 450 Å |
| Example 3 | Compound C 100 Å | NPD 300 Å | Compound D | Compound 2 13% | Compound D 50 Å | Alq 450 Å |
| Example 4 | Compound B 100 Å | NPD 300 Å | Compound D | Compound 1 7% | Compound D 50 Å | Alq 450 Å |
| Example 5 | Compound B 100 Å | NPD 300 Å | Compound D | Compound 1 10% | Compound D 50 Å | Alq 450 Å |
| Example 6 | Compound B 100 Å | NPD 300 Å | Compound D | Compound 4 7% | Compound D 50 Å | Alq 450 Å |
| Example 7 | Compound B 100 Å | NPD 300 Å | Compound D | Compound 4 10% | Compound D 50 Å | Alq 450 Å |
| Example 8 | Compound B 100 Å | NPD 300 Å | Compound D | Compound 3 7% | Compound D 50 Å | Alq 450 Å |
| Example 9 | Compound B 100 Å | NPD 300 Å | Compound D | Compound 3 10% | Compound D 50 Å | Alq 450 Å |
| Example 10 | Compound B 100 Å | NPD 300 Å | Compound D | Compound 5 7% | Compound D 50 Å | Alq 450 Å |
| Example 11 | Compound B 100 Å | NPD 300 Å | Compound D | Compound 5 10% | Compound D 50 Å | Alq 450 Å |

TABLE 2

VTE Device Data of Invention Compounds and Comparative Compounds

| | x | y | $\lambda_{max}$ (nm) | FWHM (nm) | Voltage (V) | LE (Cd/A) | EQE (%) | PE (lm/W) | LT80% (h) |
|---|---|---|---|---|---|---|---|---|---|
| Comparative Example 1 Compound A | 0.359 | 0.611 | 530 | 66 | 6.5 | 59.4 | 15.9 | 28.8 | 169 |
| Comparative Example 2 Compound A | 0.363 | 0.609 | 530 | 66 | 6.1 | 57.3 | 15.4 | 29.4 | 177 |
| Comparative Example 3 Compound A | 0.364 | 0.608 | 530 | 66 | 6.1 | 52.6 | 14.1 | 27.0 | 168 |
| Comparative Example 4 Compound B | 0.356 | 0.605 | 528 | 78 | 5.7 | 59.1 | 16.5 | 32.5 | 270 |
| Example 1 Compound 2 | 0.364 | 0.608 | 530 | 66 | 6.0 | 67 | 18 | 35.2 | 292 |
| Example 2 Compound 2 | 0.369 | 0.605 | 532 | 66 | 5.5 | 69.2 | 18.6 | 39.2 | 375 |
| Example 3 Compound 2 | 0.371 | 0.605 | 532 | 66 | 5.3 | 66.7 | 17.9 | 39.5 | 410 |
| Example 4 Compound 1 | 0.368 | 0.604 | 530 | 68 | 6.2 | 63.5 | 17.2 | 32.1 | 289 |
| Example 5 Compound 1 | 0.368 | 0.605 | 530 | 68 | 5.6 | 65.2 | 17.6 | 36.4 | 360 |
| Example 6 Compound 4 | 0.339 | 0.620 | 524 | 66 | 5.5 | 66.2 | 18 | 38.0 | 226 |
| Example 7 Compound 4 | 0.344 | 0.619 | 524 | 68 | 4.8 | 70.5 | 19.1 | 45.9 | 248 |
| Example 8 Compound 3 | 0.369 | 0.602 | 528 | 68 | 5.9 | 65.3 | 17.9 | 35.0 | 148 |
| Example 9 Compound 3 | 0.361 | 0.612 | 530 | 64 | 5.1 | 76.8 | 20.5 | 47.2 | 85 |
| Example 10 Compound 5 | 0.336 | 0.622 | 522 | 66 | 5.4 | 69.6 | 19.0 | 40.3 | 212 |
| Example 11 Compound 5 | 0.341 | 0.621 | 524 | 66 | 5.2 | 72.5 | 19.7 | 43.9 | 277 |

Table 2 is a summary of the device data. The luminous efficiency (LE), external quantum efficiency (EQE) and power efficiency (PE) were measured at 1000 nits, while the lifetime ($LT_{80}$%) was defined as the time required for the device to decay to 80% of its initial luminance under a constant current density of 40 mA/cm$^2$.

From Table 2 of the device results, it can be seen that the external quantum efficiency (EQE) of Compound 2 in three different doping concentrations 7%, 10%, 13% are 18%, 18.6% 17.9%, which are all more efficient than their corresponding Comparative Compound A EQE at same doping concentrations 15.9%, 15.4% and 14.1%, respectively. Comparative Compound A lacks the alkyl group at position $R_1$. This is also true for their luminous efficiency (LE). Similarly higher EQE and LE results were found for Compounds 1, 3, 4 and 5 when compared to Comparative Compound A and B. Additionally, the lifetime at $LT_{80\%}$ of Compound 2 and 1 are significantly longer than comparative Compound A and B at different doping concentrations.

TABLE 3

Sublimation Temperature of Alkyl Substituted Compound A

| Compounds | Sublimation Temperature (° C.) | Sublimation Temperature Difference with Respect to Compound A |
|---|---|---|
| 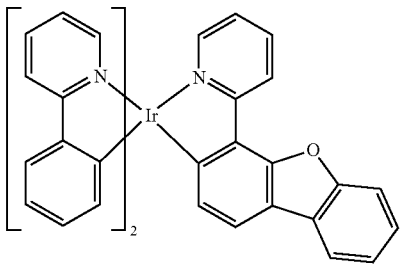<br>Comparative Compound A | 247 | N/A |
| 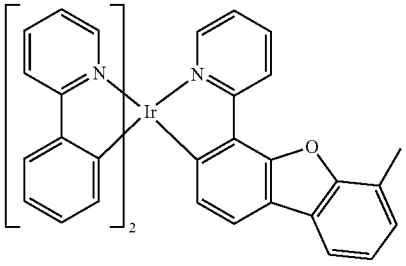<br>Compound 1 | 214 | 33 |
| 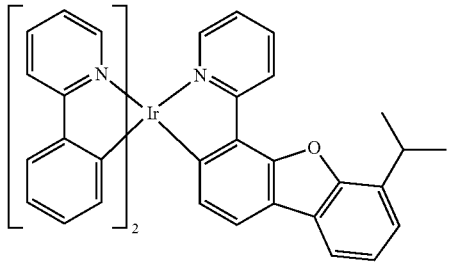<br>Compound 2 | 194 | 53 |
| 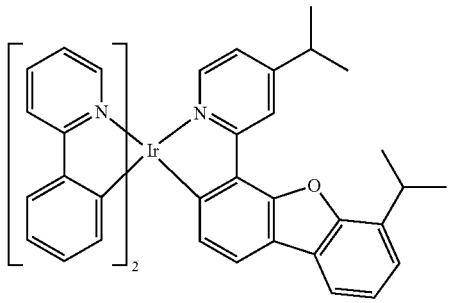<br>Compound 4 | 232 | 15 |

TABLE 3-continued

Sublimation Temperature of Alkyl Substituted Compound A

| Compounds | Sublimation Temperature (° C.) | Sublimation Temperature Difference with Respect to Compound A |
|---|---|---|
| Compound 5 | 208 | 39 |

Table 3 illustrates the effect of alkylation at one of positions $R_1$ through $R_4$ on the sublimation temperature of compounds of Formula I. Compounds of Formula I, such as Compounds 1, 2, 4, and 5, are alkylated analogs of Comparative Compound A. The sublimation temperatures of Compound 1, 2, 4 and 5 are significantly lower than that of Comparative Compound A. As discussed above, the lower sublimation temperature of these compounds may be due to the alkylation which may prevent the molecular stacking in solid state and therefore reduce the intermolecular interaction and lower the sublimation temperature. These desired device results indicate that the alkyl substitution on the dibenzofuran fragment of Comparative Compound A will improve device performance significantly in terms of device lifetime, efficiency, and sublimation temperature.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

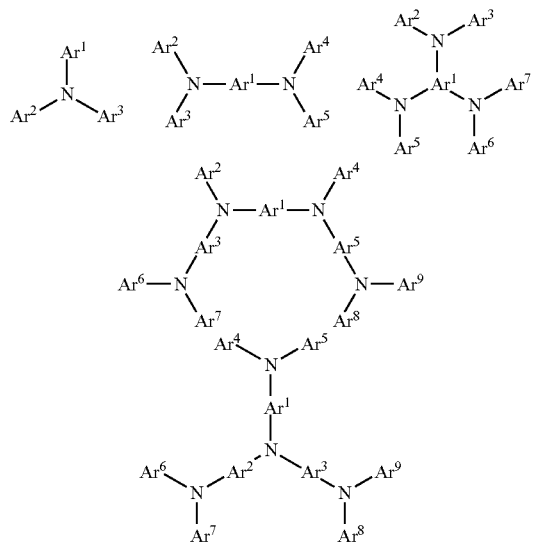

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

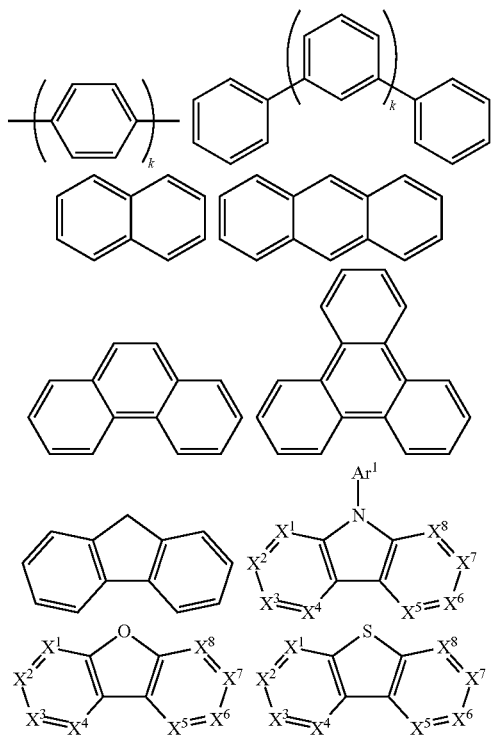

k is an integer from 1 to 20; $X^1$ to $X^8$ is C (including CH) or N; $Ar^1$ has the same group defined above.

Examples of metal complexes used in HIL or HTL include, but not limit to the following general formula:

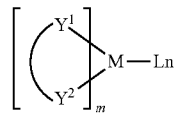

M is a metal, having an atomic weight greater than 40; $(Y^1—Y^2)$ is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1—Y^2)$ is a 2-phenylpyridine derivative.
In another aspect, $(Y^1—Y^2)$ is a carbene ligand.
In another aspect, M is selected from Ir, Pt, Os, and Zn.
In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

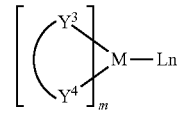

M is a metal; $(Y^3—Y^4)$ is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

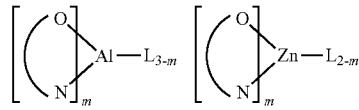

(O—N) is a bidentate ligand, having metal coordinated to atoms O and N.

In another aspect, M is selected from Ir and Pt.
In a further aspect, $(Y^3—Y^4)$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atoms, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

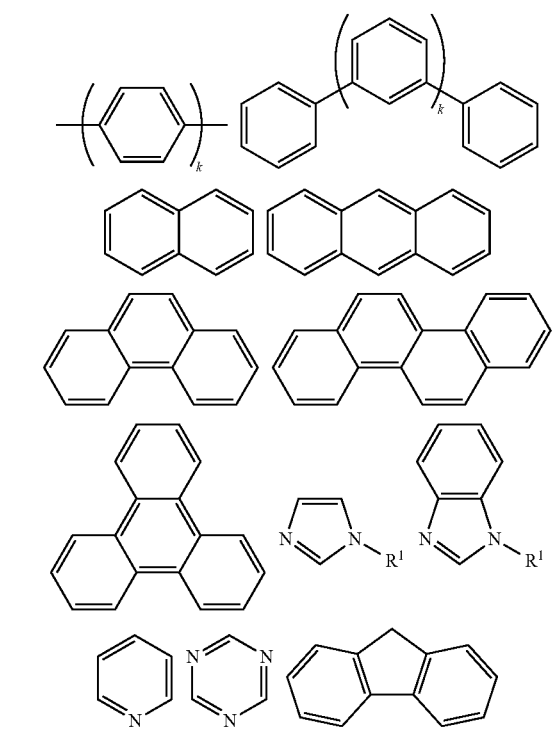

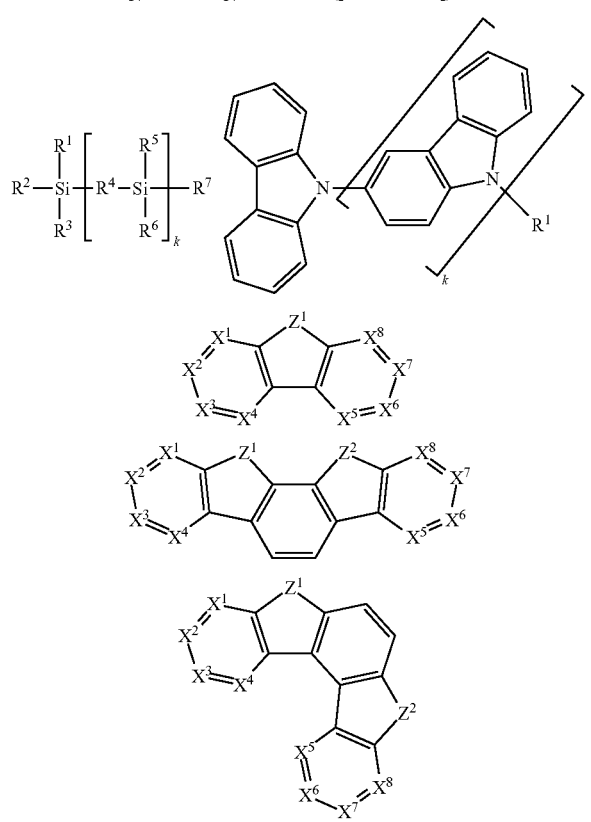

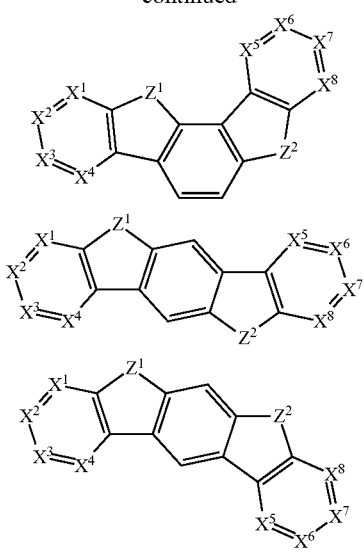

R$^1$ to R$^7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 0 to 20.

X$^1$ to X$^8$ is selected from C (including CH) or N.

Z$^1$ and Z$^2$ is selected from NR$^1$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

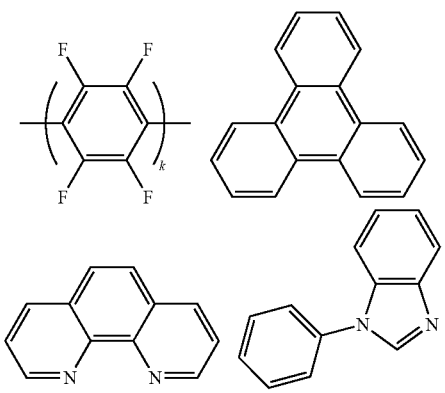

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

$R^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from C (including CH) or N.

In another aspect, the metal complexes used in ETL contains, but not limit to the following general formula:

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of the OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 4 below. Table 4 lists non-limiting classes of materials, non-limiting examples of compounds for each class, and references that disclose the materials.

TABLE 4

| MATERIAL | EXAMPLES OF MATERIAL | PUBLICATIONS |
| --- | --- | --- |
| Hole injection materials | | |
| Phthalocyanine and porphryin compounds | | Appl. Phys. Lett. 69, 2160 (1996) |
| Starburst triarylamines | | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT: PSS, polyaniline, polypthiophene) | | Synth. Met. 87, 171 (1997) WO2007002683 |
| Phosphonic acid and sliane SAMs | | US20030162053 |
| Triarylamine or polythiophene polymers with conductivity dopants | | EP1725079A1 |

TABLE 4-continued
| MATERIAL | EXAMPLES OF MATERIAL | PUBLICATIONS |
|---|---|---|
| | 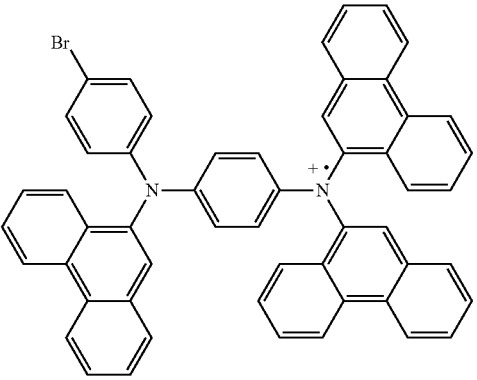 [SMILES: Brc1ccc(N(c2ccc(N(c3cc4ccccc4c4ccccc34)c3cc4ccccc4c4ccccc34)cc2)c2cc3ccccc3c3ccccc23)cc1] | |
| | 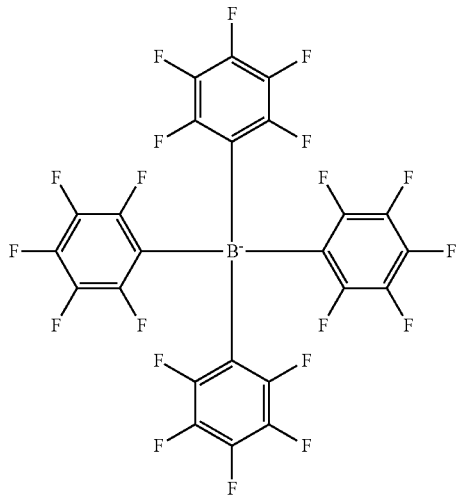 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | |
| Organic compounds with conductive inorganic compounds, such as molybdenum and tungsten oxides | 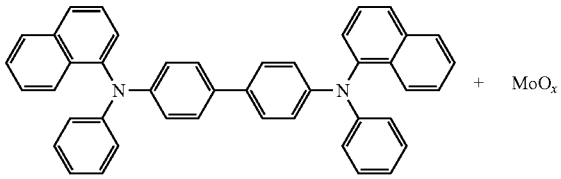 + $MoO_x$ | US20050123751<br>SID Symposium Digest, 37, 923 (2006)<br>WO2009018009 |
| n-type semiconducting organic complexes | 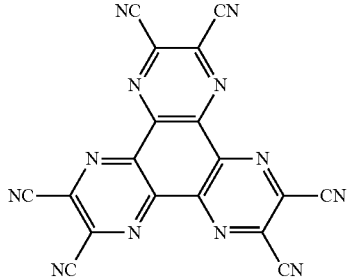 [SMILES: N#Cc1nc2c3nc(C#N)c(C#N)nc3c3nc(C#N)c(C#N)nc3c2nc1C#N] | US20020158242 |
| Metal organometallic complexes | 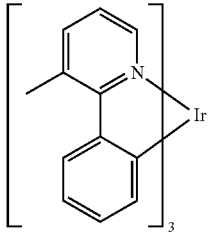 | US20060240279 |

TABLE 4-continued

| MATERIAL | EXAMPLES OF MATERIAL | PUBLICATIONS |
| --- | --- | --- |
| Cross-linkable compounds | | US20080220265 |
| Polythiophene based polymers and copolymers | | WO2011075644<br>EP2350216 |

Hole transporting materials

| | | |
| --- | --- | --- |
| Triarylamines<br>(e.g., TPD, α-NPD) | | Appl. Phys. Lett. 51, 913 (1987) |
| | | US5061569 |

47
TABLE 4-continued
| MATERIAL | EXAMPLES OF MATERIAL | PUBLICATIONS |
|---|---|---|
| | 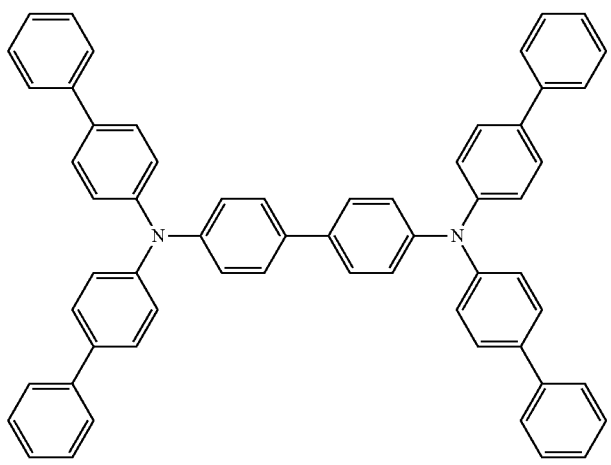 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 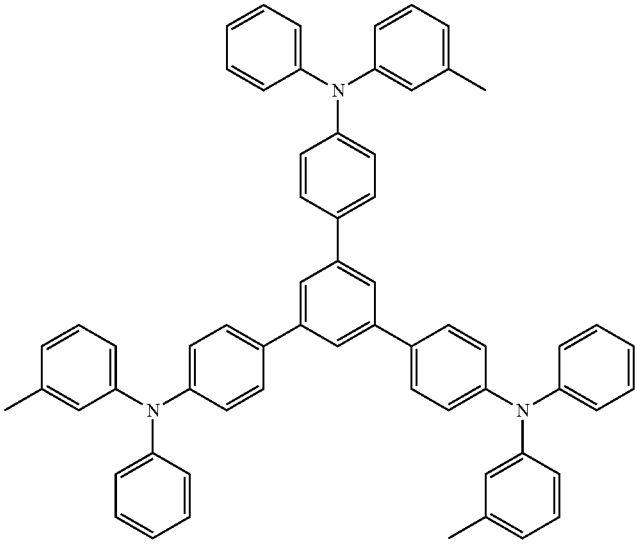 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 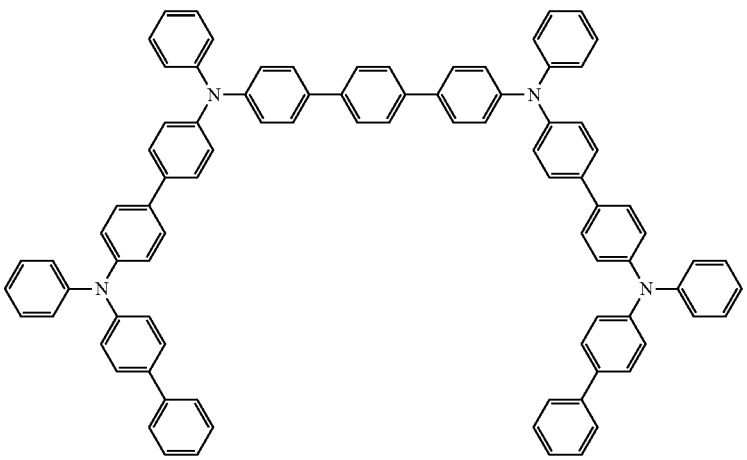 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE 4-continued

| MATERIAL | EXAMPLES OF MATERIAL | PUBLICATIONS |
|---|---|---|
| | | Appl. Phys. Lett. 90, 183503 (2007) |
| Triaylamine on spirofluorene core | | Synth. Met. 91, 209 (1997) |
| Arylamine carbazole compounds | | Adv. Mater. 6, 677 (1994), US20080124572 |
| Triarylamine with (di)benzothiophene/ (di)benzofuran | | US20070278938, US20080106190 US20110163302 |

TABLE 4-continued
| MATERIAL | EXAMPLES OF MATERIAL | PUBLICATIONS |
|---|---|---|
| Indolocarbazoles | 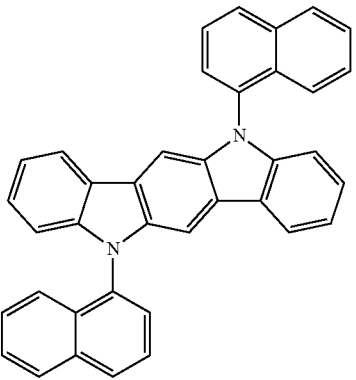 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 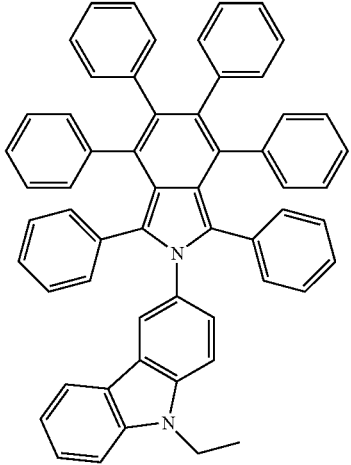 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 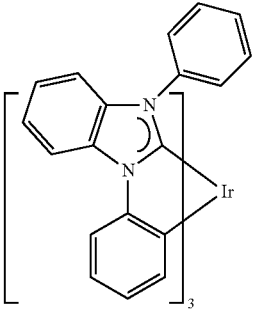 | US20080018221 |
Phosphorescent OLED host materials
Red hosts
| Arylcarbazoles | 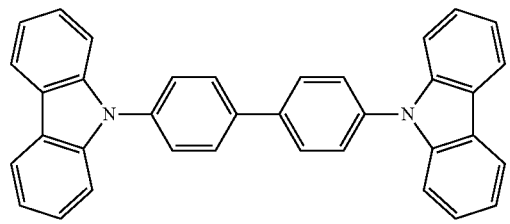 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |

TABLE 4-continued

| MATERIAL | EXAMPLES OF MATERIAL | PUBLICATIONS |
| --- | --- | --- |
| Metal 8-hydroxyquinolates (e.g., Alq₃, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |

TABLE 4-continued

| MATERIAL | EXAMPLES OF MATERIAL | PUBLICATIONS |
|---|---|---|
| Zinc complexes | | WO2010056066 |
| Chrysene based compounds | | WO2011086863 |
| Green hosts | | |
| Arylcarbazoles | | Appl. Phys. Lett. 78, 1622 (2001) |
| | | US20030175553 |
| | | WO2001039234 |
| Aryltriphenylene compounds | | US20060280965 |

TABLE 4-continued
| MATERIAL | EXAMPLES OF MATERIAL | PUBLICATIONS |
|---|---|---|
| | 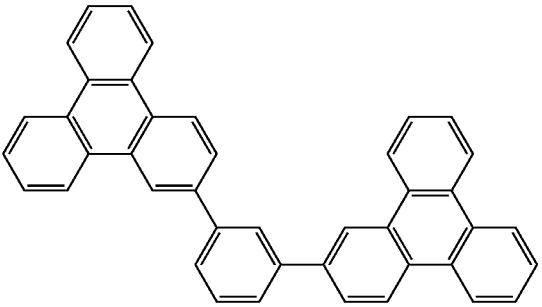 [SMILES: c1cc(-c2ccc3c4ccccc4c4ccccc4c3c2)cc(-c2ccc3c4ccccc4c4ccccc4c3c2)c1] | US20060280965 |
| | 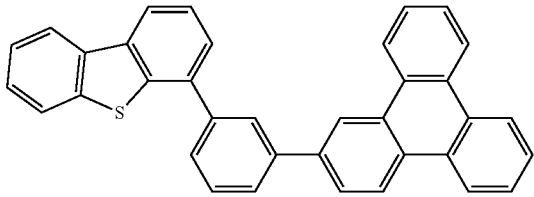 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 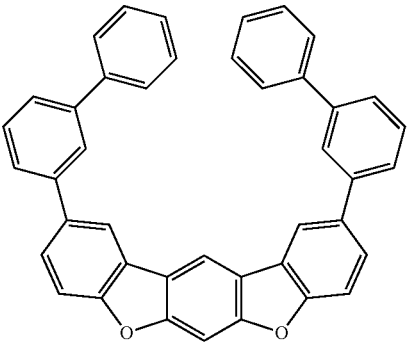 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 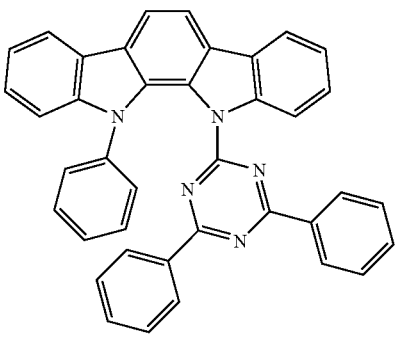 [SMILES: c1ccc(-c2nc(-c3ccccc3)nc(-n3c4ccccc4c4ccc5c6ccccc6n(-c6ccccc6)c5c43)n2)cc1] | WO2008056746 |
| | 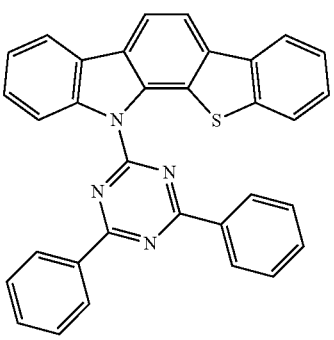 [SMILES: c1ccc(-c2nc(-c3ccccc3)nc(-n3c4ccccc4c4ccc5c6ccccc6sc5c43)n2)cc1] | WO2010107244 |

TABLE 4-continued

| MATERIAL | EXAMPLES OF MATERIAL | PUBLICATIONS |
|---|---|---|
| Aza-carbazole/DBT/DBF | | JP2008074939 |
| | | US20100187984 |
| Polymers (e.g., PVK) | | Appl. Phys. Lett. 77, 2280 (2000) |
| Spirofluorene compounds | | WO2004093207 |
| Metal phenoxybenzooxazole compounds | | WO2005089025 |

TABLE 4-continued
| MATERIAL | EXAMPLES OF MATERIAL | PUBLICATIONS |
|---|---|---|
| | 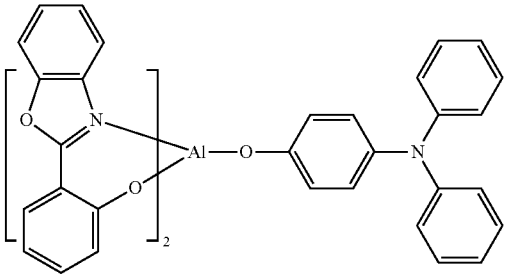 | WO2006132173 |
| | 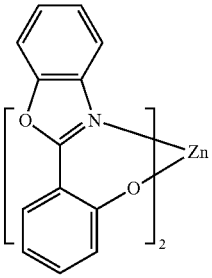 | JP200511610 |
| Spirofluorene-carbazole compounds | 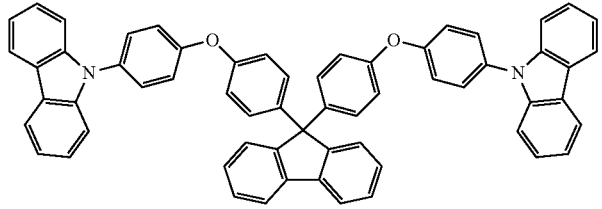 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |
| | 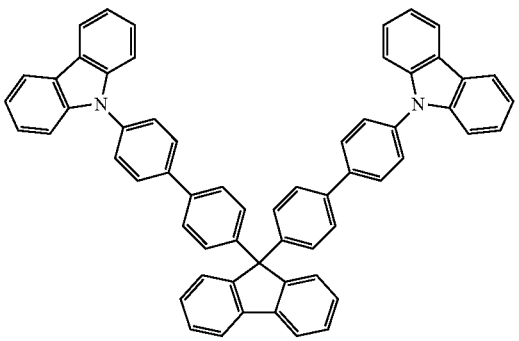 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocabazoles | 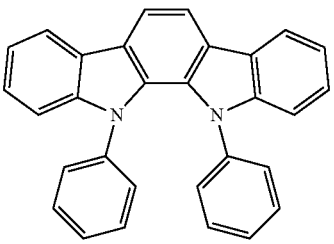 [SMILES: c1ccc(-n2c3ccccc3c3ccc4c5ccccc5n(-c5ccccc5)c4c32)cc1] | WO2007063796 |

TABLE 4-continued
| MATERIAL | EXAMPLES OF MATERIAL | PUBLICATIONS |
|---|---|---|
| | 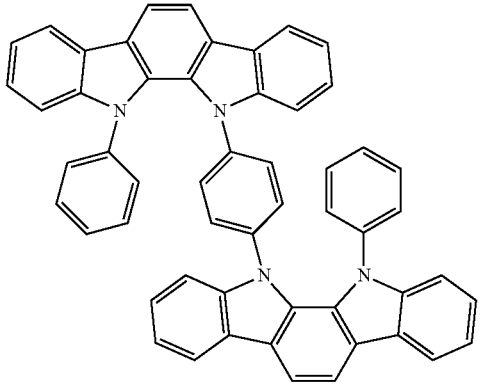 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 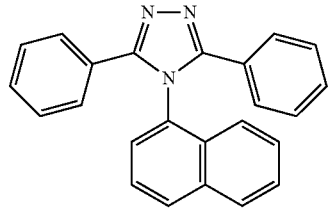 [SMILES: c1ccc(-c2nnc(-c3ccccc3)n2-c2cccc3ccccc23)cc1] | J. Appl. Phys. 90, 5048 (2001) |
| | 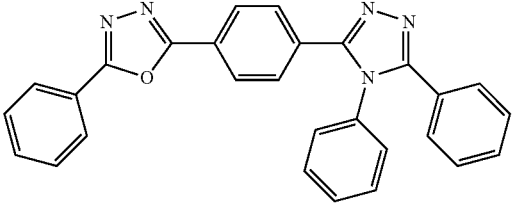 [SMILES: c1ccc(-c2nnc(-c3ccc(-c4nnc(-c5ccccc5)n4-c4ccccc4)cc3)o2)cc1] | WO2004107822 |
| Tetraphenylene complexes | 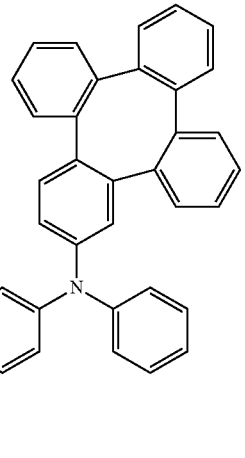 | US20050112407 |
| Metal phenoxypyridine compounds | 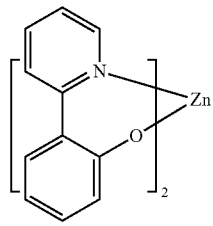 | WO2005030900 |

TABLE 4-continued

| MATERIAL | EXAMPLES OF MATERIAL | PUBLICATIONS |
| --- | --- | --- |
| Metal coordination complexes (e.g., Zn, Al with N^N ligands) | | US20040137268, US20040137267 |
| Blue hosts | | |
| Arylcarbazoles | | Appl. Phys. Lett. 82, 2422 (2003) |
| | | US20070190359 |
| Dibenzothiophene/ Dibenzofuran-carbazole compounds | | WO2006114966, US20090167162 |
| | | US20090167162 |
| | | WO2009086028 |

TABLE 4-continued
| MATERIAL | EXAMPLES OF MATERIAL | PUBLICATIONS |
|---|---|---|
| | 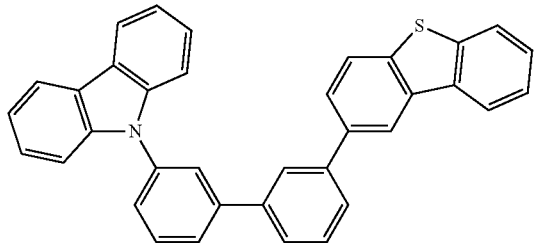 [SMILES: c1cc(-c2cccc(-n3c4ccccc4c4ccccc43)c2)cc(-c2ccc3sc4ccccc4c3c2)c1] | US20090030202, US20090017330 |
| | 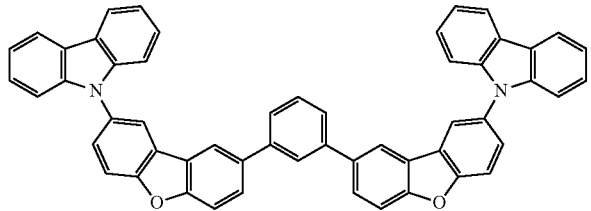 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 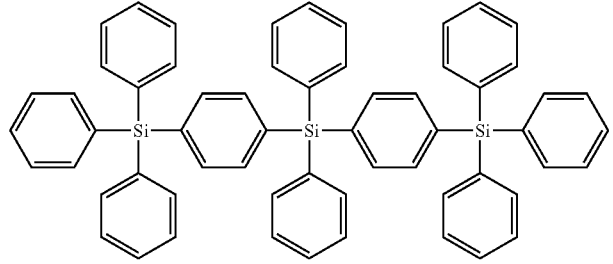 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 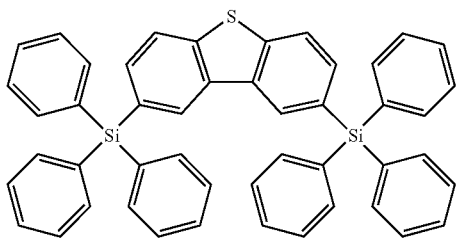 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 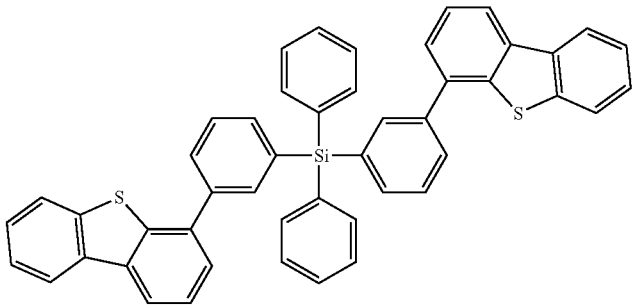 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 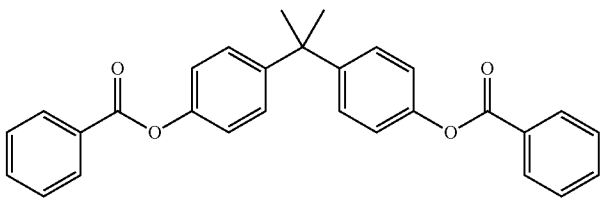 [SMILES: CC(C)(c1ccc(OC(=O)c2ccccc2)cc1)c1ccc(OC(=O)c2ccccc2)cc1] | WO2006100298 |

TABLE 4-continued
| MATERIAL | EXAMPLES OF MATERIAL | PUBLICATIONS |
|---|---|---|
| Carbazole linked by non-conjugated groups | 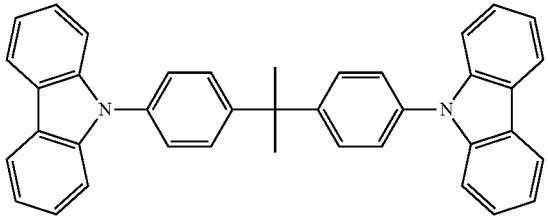 [SMILES: CC(C)(c1ccc(-n2c3ccccc3c3ccccc32)cc1)c1ccc(-n2c3ccccc3c3ccccc32)cc1] | US20040115476 |
| Aza-carbazoles | 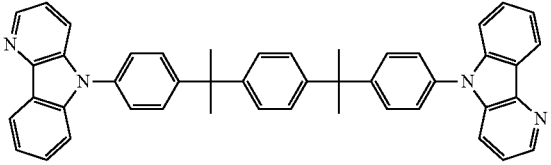 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| High triplet metal organometallic complex | 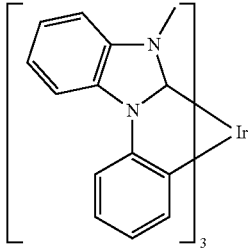 | US7154114 |
Phosphorescent dopants
Red dopants
| MATERIAL | EXAMPLES OF MATERIAL | PUBLICATIONS |
|---|---|---|
| Heavy metal porphyrins (e.g., PtOEP) | 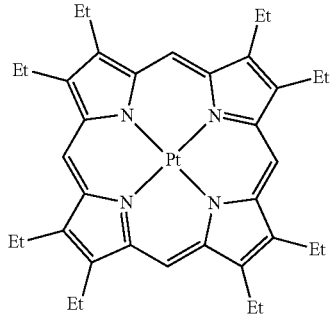 | Nature 395, 151 (1998) |
| Iridium(III) organometallic complexes | 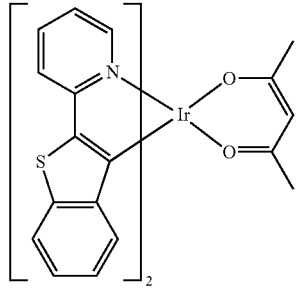 | Appl. Phys. Lett. 78, 1622 (2001) |
| | 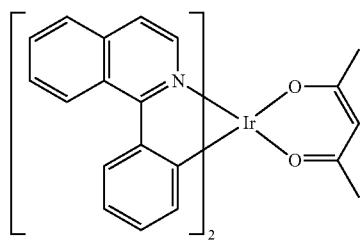 | US2006835469 |

TABLE 4-continued
| MATERIAL | EXAMPLES OF MATERIAL | PUBLICATIONS |
|---|---|---|
| | 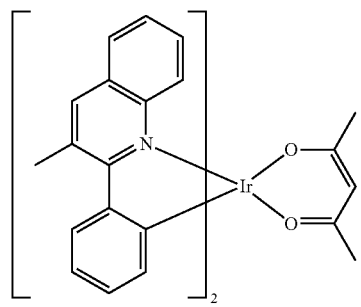 | US2006835469 |
| | 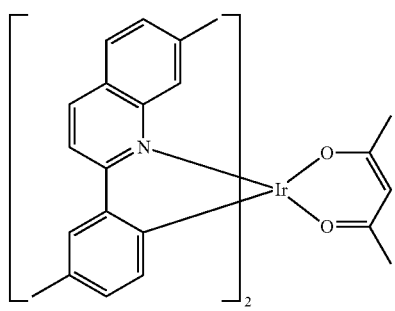 | US20060202194 |
| | 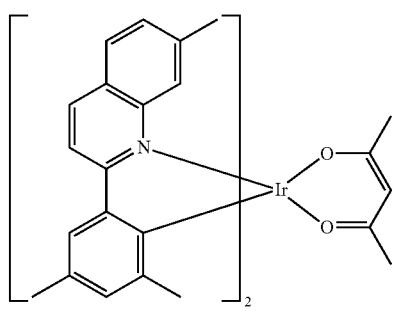 | US20060202194 |
| | 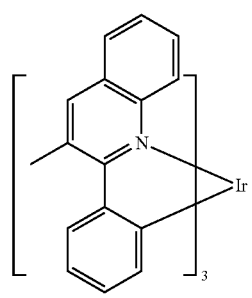 | US20070087321 |
| | 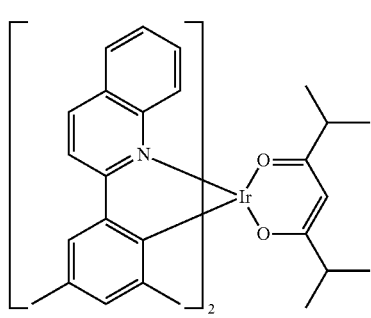 | US20080261076<br>US20100090591 |

TABLE 4-continued

| MATERIAL | EXAMPLES OF MATERIAL | PUBLICATIONS |
|---|---|---|
| | | US20070087321 |
| | | Adv. Mater. 19, 739 (2007) |
| | | WO2009100991 |
| | | WO2008101842 |
| | | US7232618 |

TABLE 4-continued
| MATERIAL | EXAMPLES OF MATERIAL | PUBLICATIONS |
|---|---|---|
| Platinum(II) organometallic complexes | 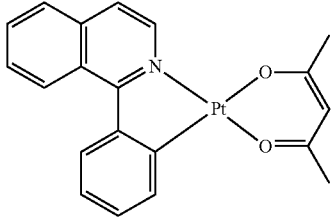 | WO2003040257 |
| | 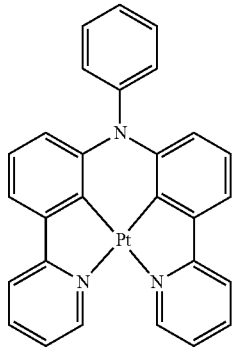 | US20070103060 |
| Osminum(III) complexes | 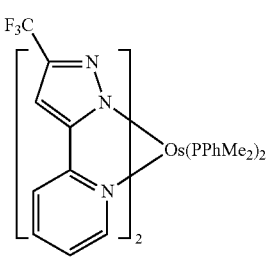 | Chem. Mater. 17, 3532 (2005) |
| Ruthenium(II) complexes | 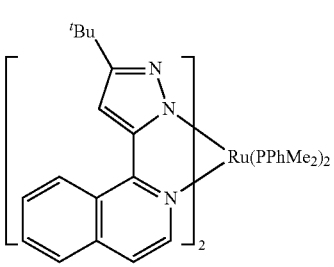 | Adv. Mater. 17, 1059 (2005) |
| Rhenium (I), (II), and (III) complexes | 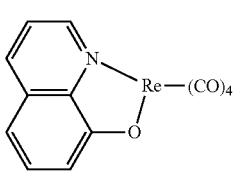 | US20050244673 |

TABLE 4-continued
| MATERIAL | EXAMPLES OF MATERIAL | PUBLICATIONS |
|---|---|---|
| | Green dopants | |
| Iridium(III) organometallic complexes | 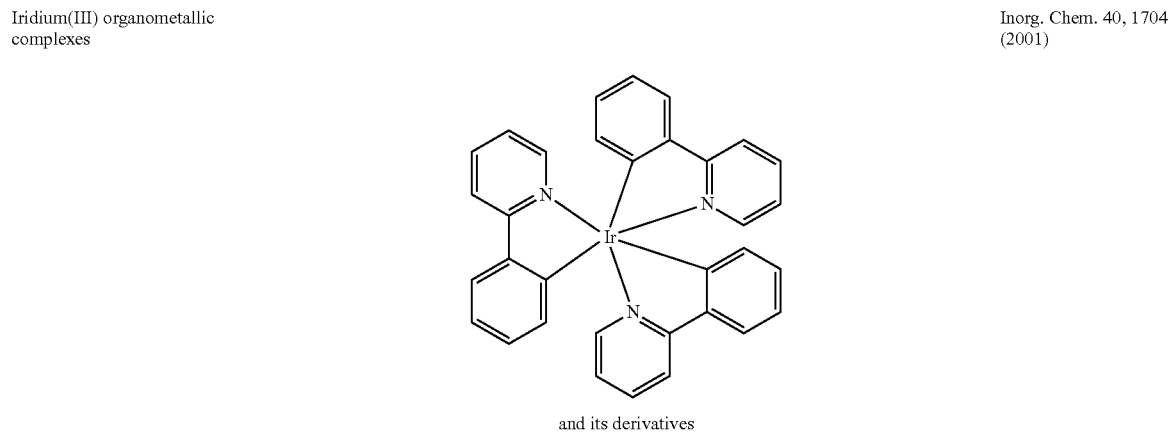<br>and its derivatives | Inorg. Chem. 40, 1704 (2001) |
| | 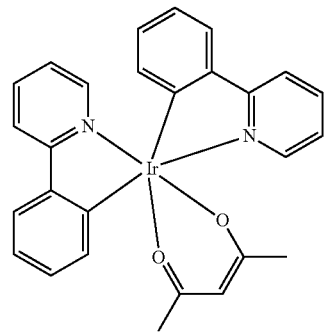 | US20020034656 |
| | 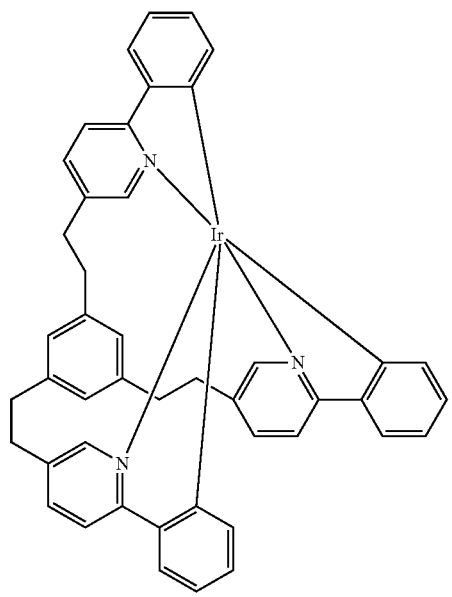 | US7332232 |

TABLE 4-continued

| MATERIAL | EXAMPLES OF MATERIAL | PUBLICATIONS |
|---|---|---|
| | | US20090108737 |
| | | WO2010028151 |
| | | EP1841834B |
| | | US20060127696 |
| | | US20090039776 |

TABLE 4-continued

| MATERIAL | EXAMPLES OF MATERIAL | PUBLICATIONS |
|---|---|---|
| | | US6921915 |
| | | US20100244004 |
| | | US6687266 |
| | | Chem. Mater. 16, 2480 (2004) |
| | | US20070190359 |

TABLE 4-continued

| MATERIAL | EXAMPLES OF MATERIAL | PUBLICATIONS |
|---|---|---|
| | | US20060008670<br>JP2007123392 |
| | | WO2010086089,<br>WO2011044988 |
| | | Adv. Mater. 16, 2003<br>(2004) |
| | | Angew. Chem. Int. Ed.<br>2006, 45, 7800 |
| | | WO2009050290 |
| | | US20090165846 |

TABLE 4-continued
| MATERIAL | EXAMPLES OF MATERIAL | PUBLICATIONS |
|---|---|---|
| | 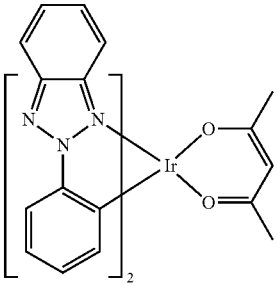 | US20080015355 |
| | 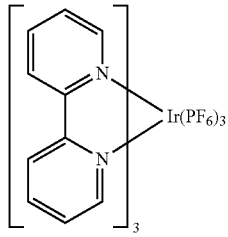 | US20010015432 |
| | 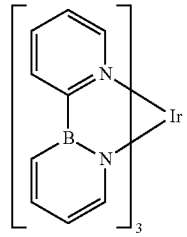 | US20100295032 |
| Monomer for polymeric metal organometallic compounds | 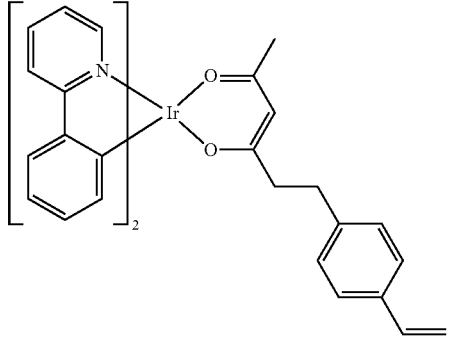 | US7250226, US7396598 |
| Pt(II) organometallic complexes, including polydentated ligands | 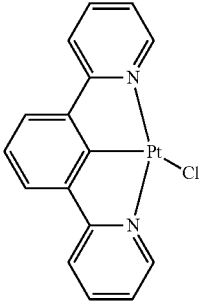 | Appl. Phys. Lett. 86, 153505 (2005) |

TABLE 4-continued
| MATERIAL | EXAMPLES OF MATERIAL | PUBLICATIONS |
|---|---|---|
| | 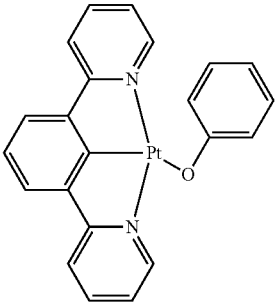 | Appl. Phys. Lett. 86, 153505 (2005) |
| | 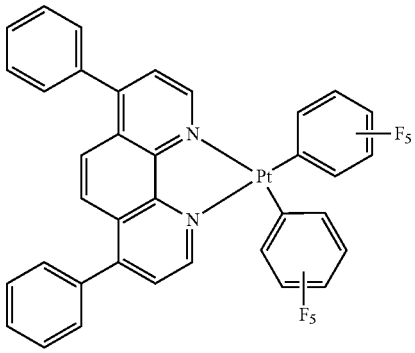 | Chem. Lett. 34, 592 (2005) |
| | 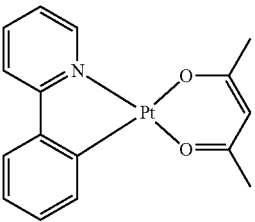 | WO2002015645 |
| | 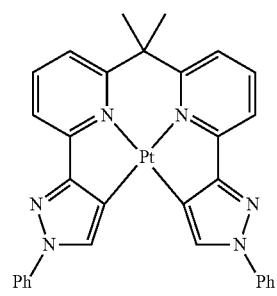 | US20060263635 |
| | 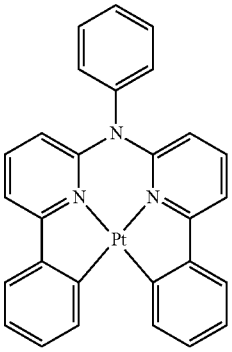 | US20060182992<br>US20070103060 |

TABLE 4-continued
| MATERIAL | EXAMPLES OF MATERIAL | PUBLICATIONS |
|---|---|---|
| Cu complexes | 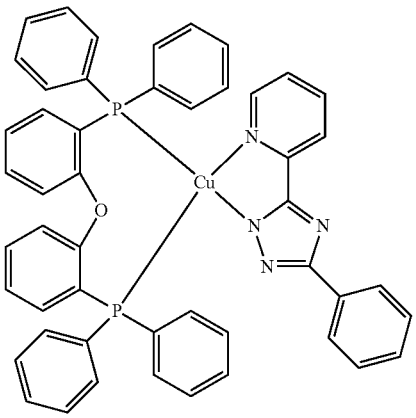 | WO2009000673 |
| | 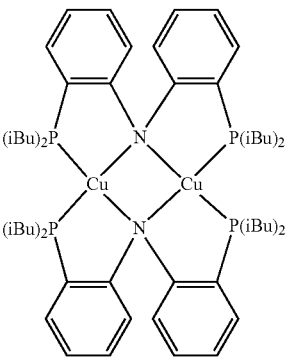 | US20070111026 |
| Gold complexes | 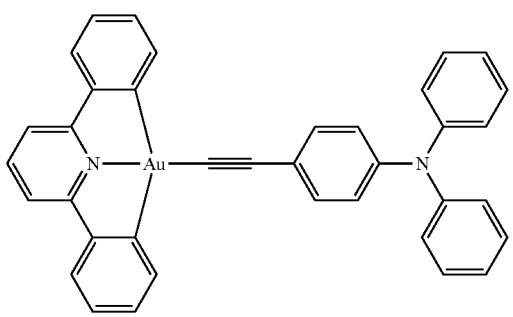 | Chem. Commun. 2906 (2005) |
| Rhenium(III) complexes | 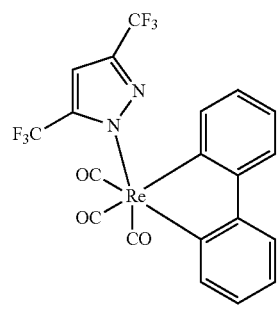 | Inorg. Chem. 42, 1248 (2003) |

TABLE 4-continued

| MATERIAL | EXAMPLES OF MATERIAL | PUBLICATIONS |
| --- | --- | --- |
| Osmium(II) complexes | | US7279704 |
| Deuterated organometallic complexes | | US20030138657 |
| Organometallic complexes with two or more metal centers | | US20030152802 |
| | | US7090928 |

TABLE 4-continued
| MATERIAL | EXAMPLES OF MATERIAL | PUBLICATIONS |
|---|---|---|
| | Blue dopants | |
| Iridium(III) organometallic complexes | 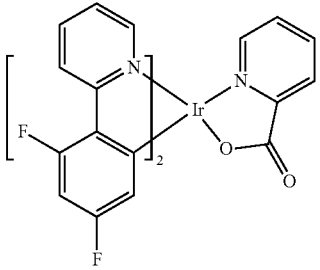 | WO2002002714 |
| | 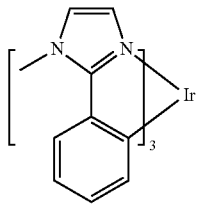 | WO2006009024 |
| | 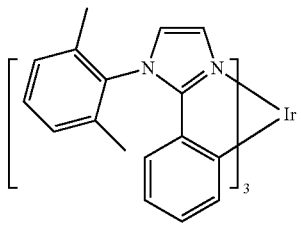 | US20060251923<br>US20110057559<br>US20110204333 |
| | 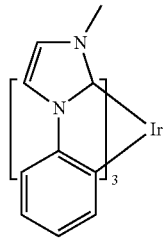 | US7393599,<br>WO2006056418,<br>US20050260441,<br>WO2005019373 |
| | 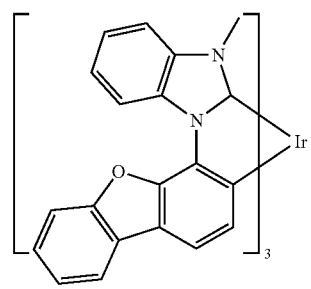 | US7534505 |

TABLE 4-continued
| MATERIAL | EXAMPLES OF MATERIAL | PUBLICATIONS |
|---|---|---|
| | 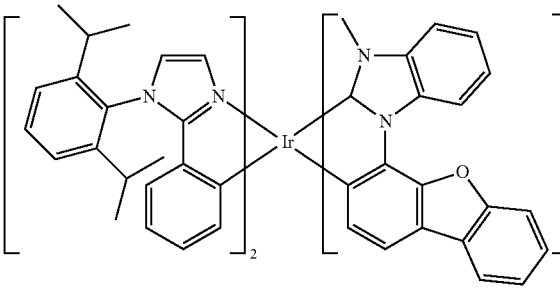 | WO2011051404 |
| | 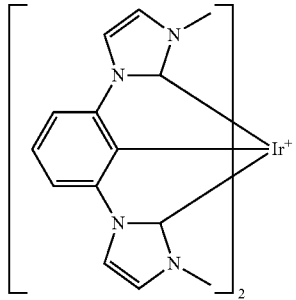 | US7445855 |
| | 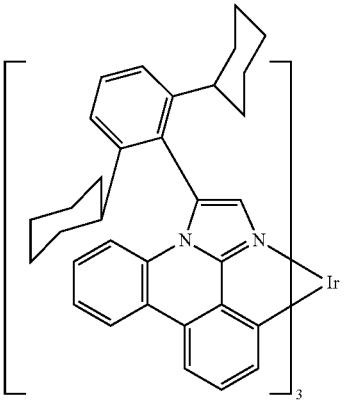 | US20070190359, US20080297033 US20100148663 |
| | 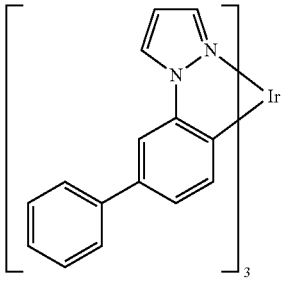 | US7338722 |
| | 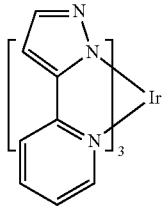 | US20020134984 |

TABLE 4-continued

| MATERIAL | EXAMPLES OF MATERIAL | PUBLICATIONS |
|---|---|---|
| | | Angew. Chem. Int. Ed. 47, 1 (2008) |
| | | Chem. Mater. 18, 5119 (2006) |
| | | Inorg. Chem. 46, 4308 (2007) |
| | | WO2005123873 |
| | | WO2005123873 |
| | | WO2007004380 |

TABLE 4-continued
| MATERIAL | EXAMPLES OF MATERIAL | PUBLICATIONS |
| --- | --- | --- |
|  | 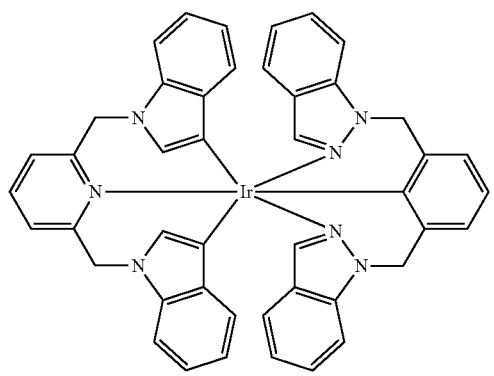 | WO2006082742 |
| Osmium(II) complexes | 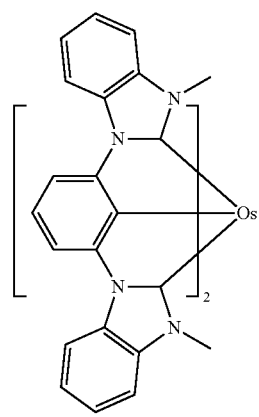 | US7279704 |
|  | 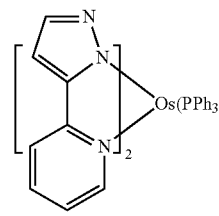 | Organometallics 23, 3745 (2004) |
| Gold complexes | 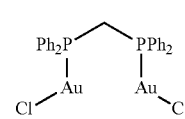 | Appl. Phys. Lett. 74, 1361 (1999) |
| Platinum(II) complexes | 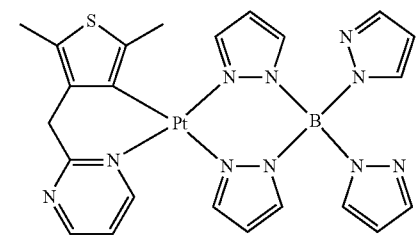 | WO2006098120, WO2006103874 |

TABLE 4-continued

| MATERIAL | EXAMPLES OF MATERIAL | PUBLICATIONS |
|---|---|---|
| Pt tetradentate complexes with at least one metal-carbene bond | 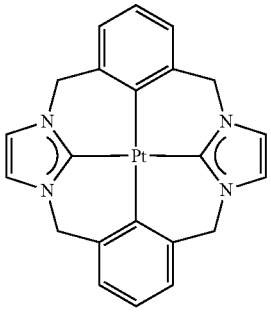 | US7655323 |
| Exciton/hole blocking layer materials | | |
| Bathocuprine compounds (e.g., BCP, BPhen) | 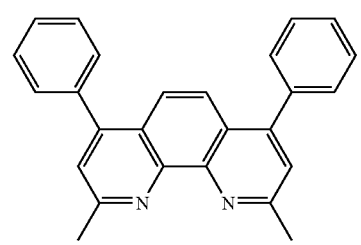 [SMILES: Cc1cc(-c2ccccc2)c2ccc3c(-c4ccccc4)cc(C)nc3c2n1] | Appl. Phys. Lett. 75, 4 (1999) |
| | 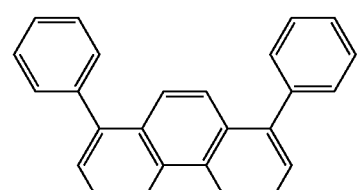 | Appl. Phys. Lett. 79, 449 (2001) |
| Metal 8-hydroxyquinolates (e.g., BAlq) | 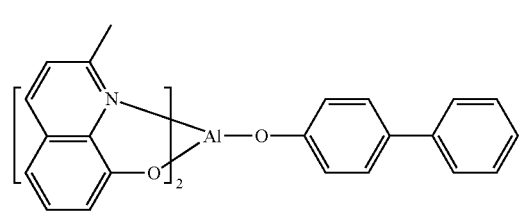 | Appl. Phys. Lett. 81, 162 (2002) |
| 5-member ring electron deficient heterocycles such as triazole, oxadiazole, imidazole, benzoimidazole | 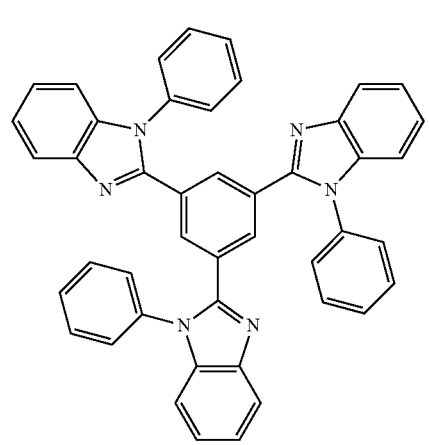 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE 4-continued
| MATERIAL | EXAMPLES OF MATERIAL | PUBLICATIONS |
|---|---|---|
| Triphenylene compounds | 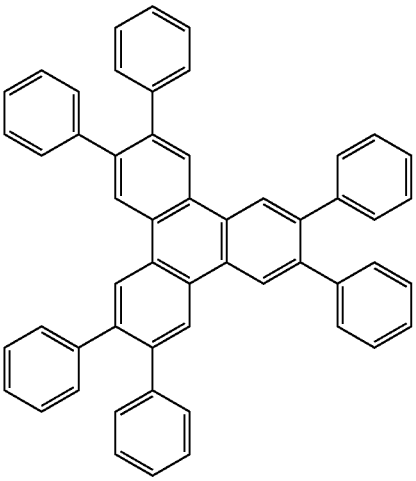 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 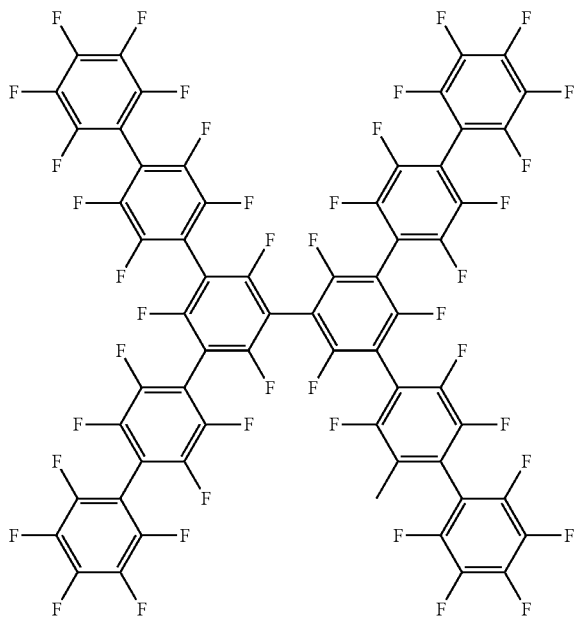 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 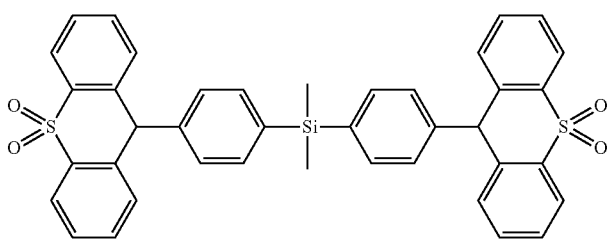 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 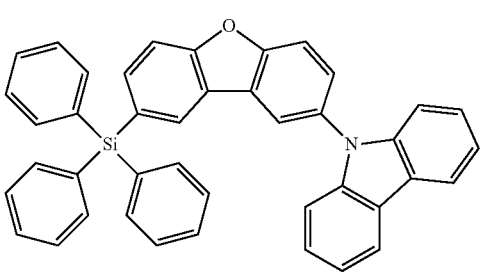 [SMILES: c1ccc([Si](c2ccccc2)(c2ccccc2)c2ccc3oc4ccc(-n5c6ccccc6c6ccccc65)cc4c3c2)cc1] | WO2010079051 |

| MATERIAL | EXAMPLES OF MATERIAL | PUBLICATIONS |
|---|---|---|
| Aza-carbazoles | 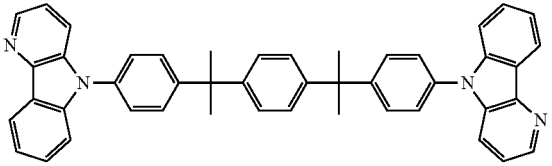 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| Electron transporting materials | | |
| Anthracene-benzoimidazole compounds | 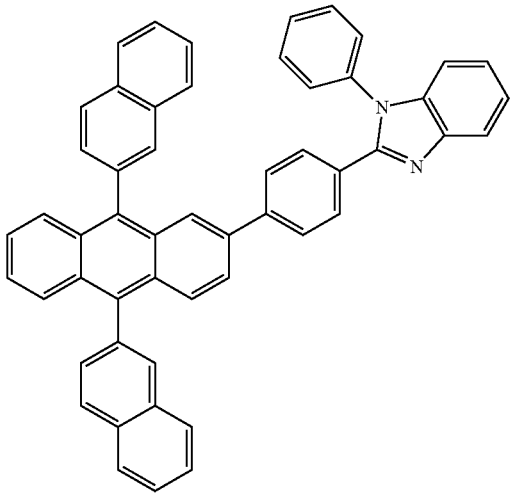 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 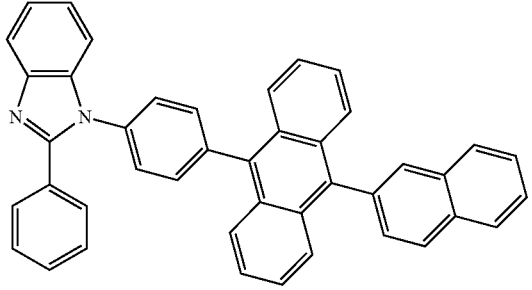 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 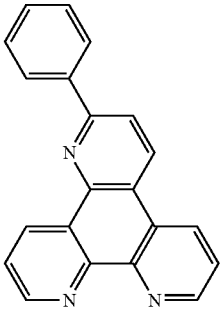 [SMILES: c1ccc(-c2ccc3c4cccnc4c4ncccc4c3n2)cc1] | US20090115316 |
| Anthracene-benzothiazole compounds | 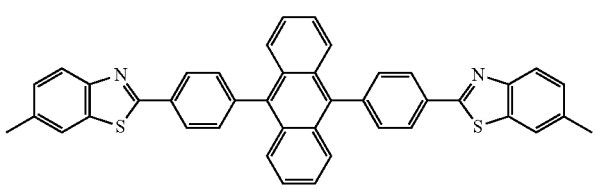 | Appl. Phys. Lett. 89, 063504 (2006) |

TABLE 4-continued

| MATERIAL | EXAMPLES OF MATERIAL | PUBLICATIONS |
|---|---|---|
| Metal 8-hydroxyquinolates (e.g., Alq$_3$, Zrq$_4$) | | Appl. Phys. Lett. 51, 913 (1987)<br>US7230107 |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |

TABLE 4-continued

| MATERIAL | EXAMPLES OF MATERIAL | PUBLICATIONS |
|---|---|---|
| | | Jpn. J. Apply. Phys. 32, L917 (1993) |
| Silole compounds | | Org. Electron. 4, 113 (2003) |
| Arylborane compounds | | J. Am. Chem. Soc. 120, 9714 (1998) |
| Fluorinated aromatic compounds | | J. Am. Chem. Soc. 122, 1832 (2000) |
| Fullerene (e.g., C60) | | US20090101870 |
| Triazine complexes | | US20040036077 |

TABLE 4-continued

| MATERIAL | EXAMPLES OF MATERIAL | PUBLICATIONS |
| --- | --- | --- |
| Zn (N^N) complexes | 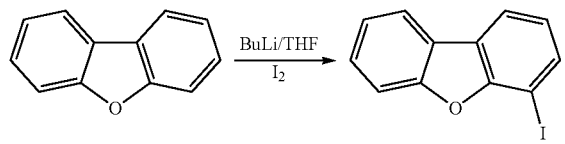 | US6528187 |

EXPERIMENTAL

Chemical abbreviations used throughout this document are as follows: Cy is cyclohexyl, dba is dibenzylideneacetone, EtOAc is ethyl acetate, DME is dimethoxyethane, dppe is 1,2-bis(diphenylphosphino)ethane, THF is tetrahydrofuran, DCM is dichloromethane, S-Phos is dicyclohexyl(2',6'-dimethoxy-[1,1'-biphenyl]-2-yl)phosphine.

Synthesis of Compound 1

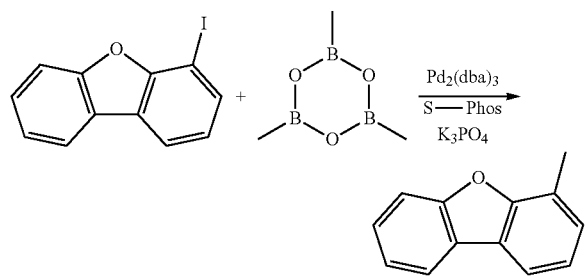

Synthesis of 4-iodobenzo[b,d]furan: A 1 L round bottom flask was charged with 2,4-dibenzo[b,d]furan (25 g, 149 mmol) in 300 mL THF, cooled to −78° C. n-Butyl lithium (102 mL, 164 mmol) was added very slowly to the flask. The reaction was warmed up to room temperature and allowed to stir for five hours. Subsequently, the reaction was cooled back to −78° C. A solution of iodine (37.7 g, 149 mmol) dissolved in 50 mL THF was added very slowly to the reaction. The reaction was warmed up to room temperature overnight. Aqueous sodium bicarbonate (300 mL) was added to the reaction. After separation of the layers, the aqueous layer was extracted with ethyl acetate (2×100 mL). After removal of the solvent under vacuum, the crude product was subjected to column chromatography (SiO$_2$, 3% ethyl acetate in hexane, v/v), then crystallized from hexane to yield 30 g (68.6%) of pure product.

Synthesis of 4-methyldibenzo[b,d]furan: 4-Iododibenzo[b,d]furan (10 g, 34.0 mmol) and potassium phosphate (23.49 g, 102 mmol) were dissolved in 200 mL of toluene and 20 mL of water. The reaction was purged with nitrogen for 20 minutes and then 2,4,6-trimethyl-1,3,5,2,4,6-trioxatriborinane (5.34 mL, 5.94 mmol), Pd$_2$(dba)$_3$ (0.311 g, 0.34 mmol) and S-Phos (0.558 g, 1.36 mmol) were added. The reaction was refluxed for 18 hours. After allowing the reaction to cool to room temperature, 100 mL of water was added, the organic and aqueous layers were separated, and the aqueous layer extracted twice with 100 mL of toluene. The organic layers were passed through a plug of silica gel, eluting with DCM. After evaporation of the solvent, the crude product was subjected to column chromatography (SiO$_2$, 3% ethyl acetate in hexane to 5% ethyl acetate in hexane, v/v) to yield 6 g (96.7%) pure product which was confirmed GC.

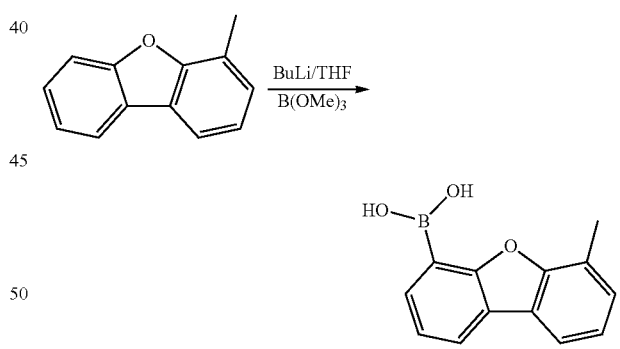

Synthesis of (6-methyldibenzo[b,d]furan-4-yl)boronic acid: n-Butyl lithium (51.4 mL, 82 mmol) was added slowly to a solution of 4-methylldibenzo[b,d]furan (6 g, 32.9 mmol) in 100 mL dry THF at −78° C. The reaction was stirred at room temperature for 5 hours and then cooled back to −78° C. Trimethyl borate (12.85 mL, 115 mmol) was added very slowly to the reaction mixture. The reaction was allowed to warm up to room temperature overnight, then poured into 100 mL of NH$_4$OH solution with ice. The mixture was extracted with 3×100 mL ethyl acetate and dried over sodium sulfate. The product was crystallized from DCM/hexane to yield 6.5 g (87%), which was confirmed by NMR.

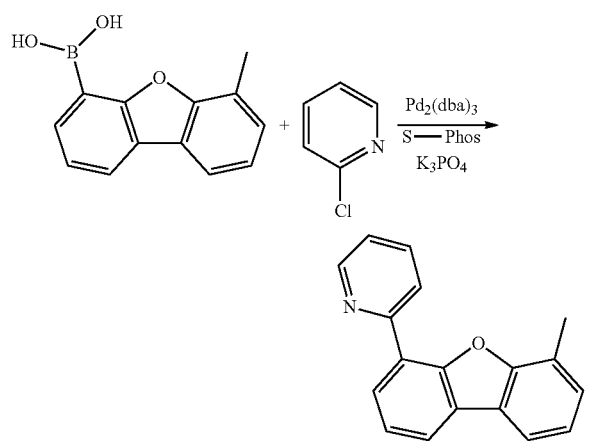

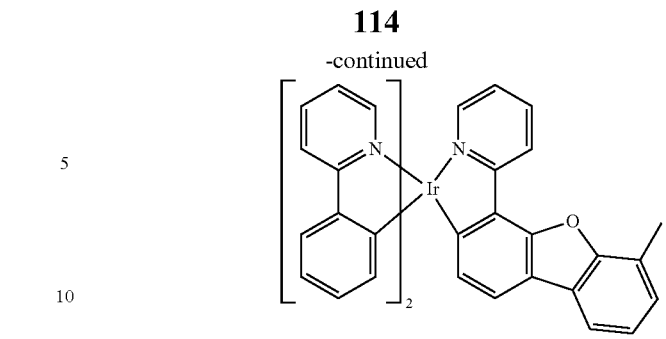

Synthesis of Compound 1: A mixture of iridium trifluoromethanesulfonate complex (2.8 g, 3.85 mmol) and 2-(6-isopropyldibenzo[b,d]furan-4-yl)pyridine (2.99 g, 11.54 mmol) in EtOH (25 mL) and MeOH (25 mL) was refluxed for 20 hours under nitrogen atmosphere. The reaction mixture was cooled back to room temperature, diluted with ethanol, and Celite® was added. The mixture was stirred for 10 minutes and filtered on a small silica gel plug and washed with ethanol (3-4 times) and hexane (3-4 times). The filtrate was discarded. The Celite®/silica plug was then washed with dichloromethane to elute the product. The crude product was chromatographed on silica gel (pre-treated with 20% triethylamine in hexane) with 30% DCM in hexane. The product was crystallized from hexane, and further purified by sublimation to yield 0.6 g (20.5%) of Compound 1, which was confirmed by LC/MS.

Synthesis of 2-(6-methyldibenzo[b,d]furan-4-yl)pyridine: (6-methyldibenzo[b,d]furan-4-yl)boronic acid (6.4 g, 28.3 mmol) and potassium phosphate (19.56 g, 85 mmol) were dissolved in 200 mL of toluene and 20 mL of water in a flask. The reaction was purged with nitrogen for 20 minutes and then 2-chloropyridine (2.66 mL, 28.3 mmol), Pd$_2$(dba)$_3$ (0.778 g, 0.849 mmol) and S-Phos (1.046 g, 2.55 mmol) were added. The reaction was refluxed for 18 hours. After cooling the reaction to room temperature, 50 mL of water was added to the mixture and the organic and aqueous layers were separated. The aqueous layer was extracted twice with 100 mL of DCM. The organic layers were passed through a plug of silica gel, eluting with DCM. After evaporation of the solvent, the crude product was subjected to column chromatography (SiO$_2$, 5% ethyl acetate in hexane to 10% ethyl acetate in hexane, v/v). The product was subjected to second column chromatography (SiO$_2$, 50 to 100% DCM in hexane, v/v) to yield 3 g (40.9%) of pure product.

Synthesis of Compound 2

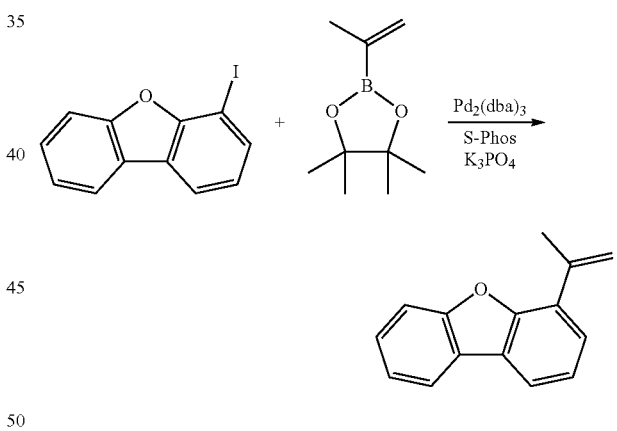

Synthesis of 4-(prop-1-en-2-yl)dibenzo[b,d]furan: 4-Iododibenzo[b,d]furan (25 g, 85.0 mmol) and potassium phosphate (58.7 g, 255 mmol) were dissolved in 500 mL of toluene and 50 mL of water. The reaction was purged with nitrogen for 20 minutes and then 4,4,5,5-tetramethyl-2-(prop-1-en-2-yl)-1,3,2-dioxaborolane (15.98 mL, 85 mmol), Pd$_2$(dba)$_3$ (1.55 g, 1.7 mmol) and S-Phos (2.79 g, 6.8 mmol) were added. The reaction was refluxed for 18 hours. After cooling the reaction to room temperature, 100 mL of water was added, the organic and aqueous layers were separated, and the aqueous layer was extracted twice with 100 mL of ethyl acetate. The organic layers were passed through a plug of silica gel, eluting with DCM. After evaporation of the solvent, the crude product was subjected to column chromatography (SiO$_2$, 3% ethyl acetate in hexane to 5% ethyl acetate in hexane, v/v) to yield 14.5 g (82%) of pure product.

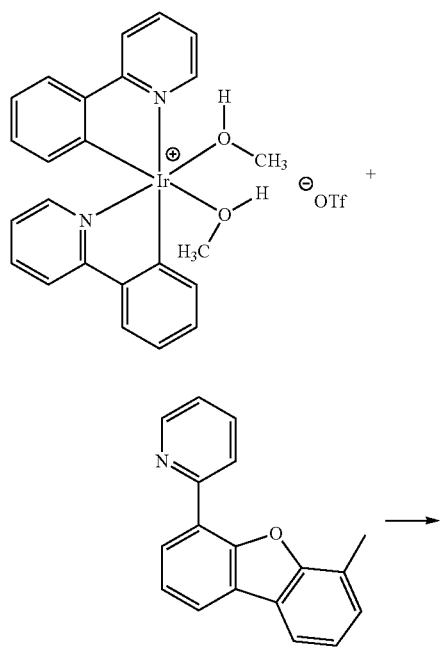

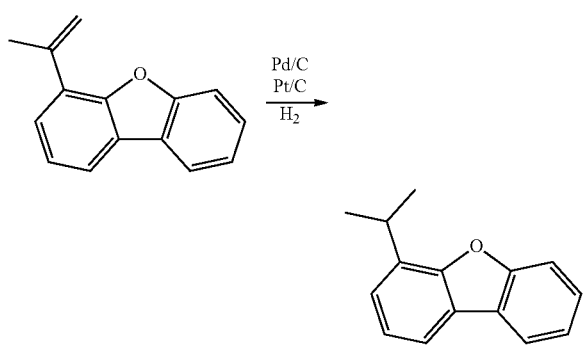

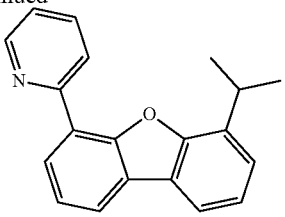

Synthesis of 2-(6-isopropyldibenzo[b,d]furan-4-yl)pyridine: (6-Isopropyldibenzo[b,d]furan-4-yl)boronic acid (4 g, 15.74 mmol) and potassium phosphate (10.88 g, 47.2 mmol) were dissolved in 200 mL of toluene and 20 mL of water. The reaction was purged with nitrogen for 20 minutes and then 2-chloropyridine (1.481 mL, 15.74 mmol), $Pd_2(dba)_3$ (0.432 g, 0.472 mmol) and S-Phos (0.582 g, 1.417 mmol) were added. The reaction was refluxed for 18 h. After cooling the reaction to room temperature, 50 mL of water was added, the organic and aqueous layers were separated, and the aqueous layer was extracted twice with 100 mL of ethyl acetate. The organic layers were passed through a plug of silica gel, eluting with DCM. After evaporation of the solvent, the crude product was subjected to column chromatography ($SiO_2$, 5% ethyl acetate in hexane to 10% ethyl acetate in hexane, v/v) to yield 2.3 g (50.8%) pure product.

Synthesis of 4-isopropyldibenzo[b,d]furan: 4-(Prop-1-en-2-yl)dibenzo[b,d]furan (14.5 g, 69.6 mmol) was added to a hydrogenator bottle with EtOH (100 mL). The reaction mixture was degassed by bubbling $N_2$ for 10 minutes. Pd/C (1.14 g, 1.39 mmol) and PVC (2.72 g, 0.7 mmol) was added. The reaction mixture was placed on a Parr hydrogenator for 2 hours ($H_2$~72 psi, based on calculations). The reaction mixture was filtered on a tightly packed Celite® bed and washed with dichloromethane. GC/MS confirmed complete conversion. The crude product was chromatographed on silica gel with 2% DCM in hexane (v/v) to yield 10.9 g (74%) of the desired product. The product was confirmed by GC/MS.

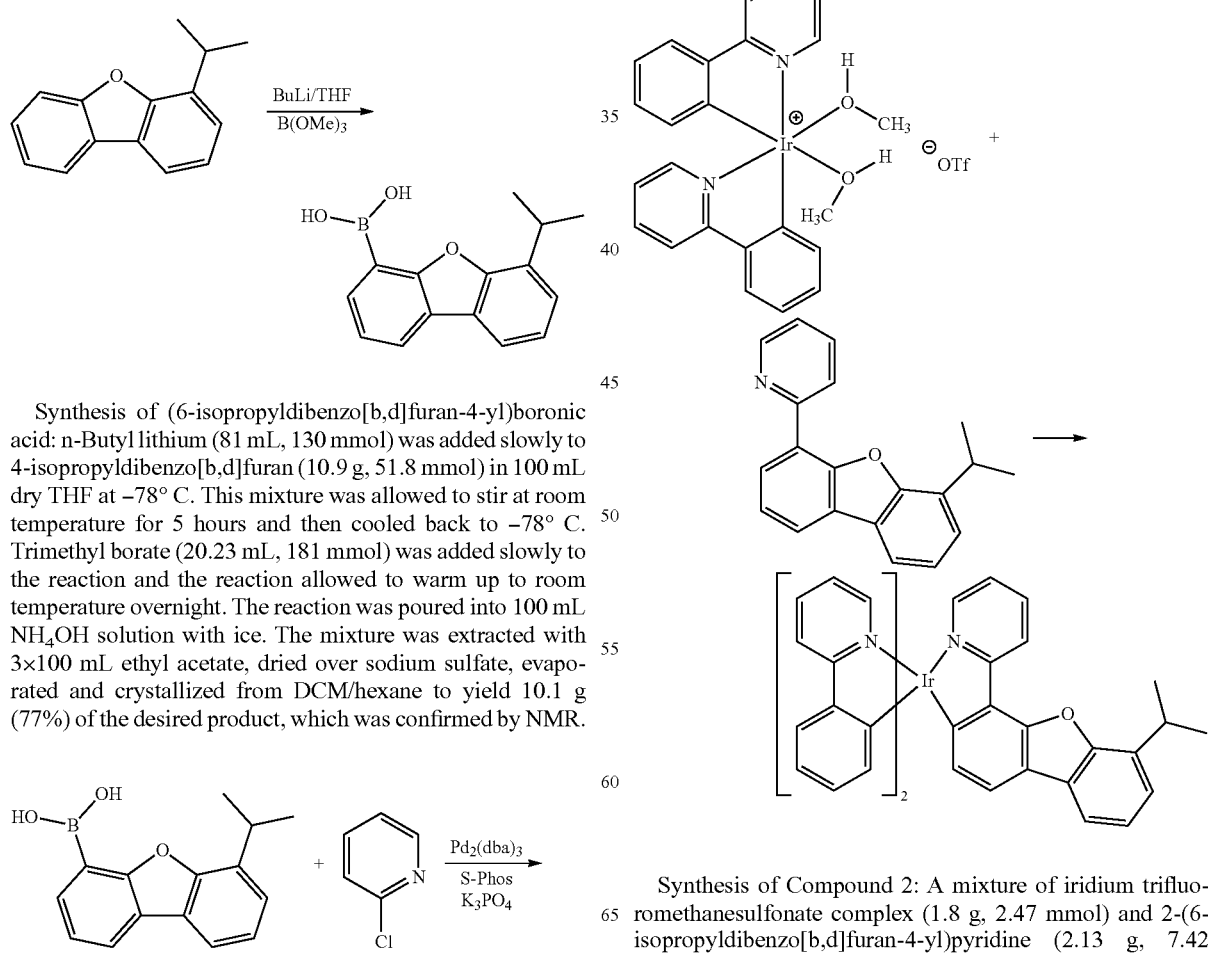

Synthesis of (6-isopropyldibenzo[b,d]furan-4-yl)boronic acid: n-Butyl lithium (81 mL, 130 mmol) was added slowly to 4-isopropyldibenzo[b,d]furan (10.9 g, 51.8 mmol) in 100 mL dry THF at −78° C. This mixture was allowed to stir at room temperature for 5 hours and then cooled back to −78° C. Trimethyl borate (20.23 mL, 181 mmol) was added slowly to the reaction and the reaction allowed to warm up to room temperature overnight. The reaction was poured into 100 mL $NH_4OH$ solution with ice. The mixture was extracted with 3×100 mL ethyl acetate, dried over sodium sulfate, evaporated and crystallized from DCM/hexane to yield 10.1 g (77%) of the desired product, which was confirmed by NMR.

Synthesis of Compound 2: A mixture of iridium trifluoromethanesulfonate complex (1.8 g, 2.47 mmol) and 2-(6-isopropyldibenzo[b,d]furan-4-yl)pyridine (2.13 g, 7.42 mmol) in EtOH (25 mL) and MeOH (25 mL) was refluxed for 20 hours under a nitrogen atmosphere. The reaction mixture was cooled back to room temperature and diluted with ethanol. Celite® was added and the mixture was stirred for 10 min. The mixture was filtered on a small silica gel plug and washed with ethanol (3-4 times) and with hexane (3-4 times). The filtrate was discarded. The Celite®/silica plug was then washed with dichloromethane to elute the product. The crude product was chromatographed on silica gel with 33% DCM in hexane (v/v). The product was crystallized from hexane/ethyl acetate, and sublimed to yield 0.6 g (30.8%) of Compound 2, which was confirmed by LC/MS.

Synthesis of Compound 3

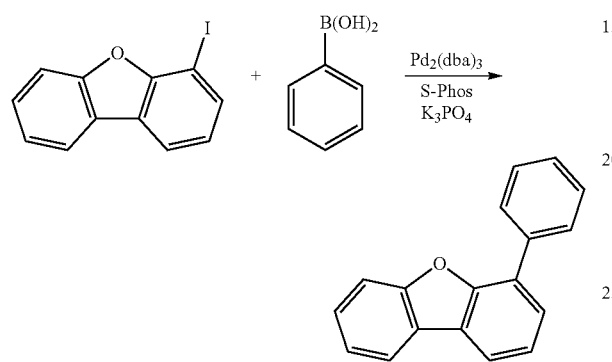

Synthesis of 4-phenyldibenzo[b,d]furan: 4-iododibenzo[b,d]furan (4 g, 13.60 mmol), phenylboronic acid (1.99 g, 16.32 mmol), dicyclohexyl(2',6'-dimethoxy-[1,1'-biphenyl]-2-yl)phosphine (0.447 g, 1.08 mmol), Pd$_2$(dba)$_2$ (0.250 g, 0.272 mmol), K$_3$PO$_4$ (10.1 g, 47.6 mmol), 150 mL toluene and 15 mL water were charged in a 250 mL flask. The reaction mixture was degassed by bubbling N$_2$ for 30 minutes and then heated to reflux under N$_2$ overnight. The reaction was cooled to room temperature and the crude product was purified by silica gel column to yield 3.3 g (99%), which was confirmed by GC-MS.

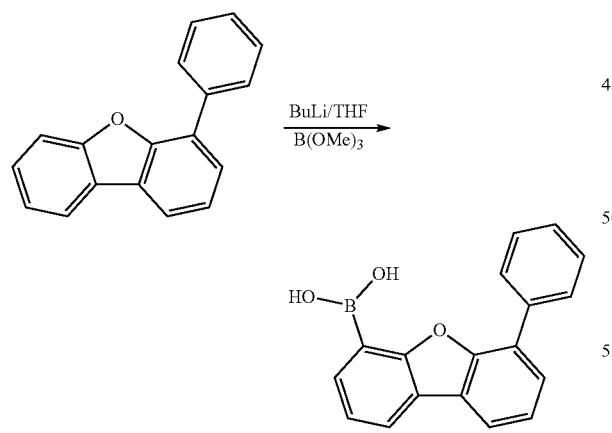

Synthesis of (6-phenyldibenzo[b,d]furan-4-yl)boronic acid: n-Butyllithium (13.51 mL, 33.8 mmol) was added dropwise to 4-phenyldibenzo[b,d]furan (3.3 g, 13.51 mmol) in 80 mL dry THF at −78° C. This reaction mixture was allowed to stir at room temperature for 5 hours and then cooled to −78° C. again. Trimethyl borate (4.52 mL, 40.5 mmol) was added slowly to the reaction. The reaction mixture was allowed to warm up to room temperature gradually over night with stirring. The mixture was poured into 50 mL of NH$_4$OH solution with ice. The aqueous mixture was extracted with 3×80 mL ethyl acetate and dried over sodium sulfate, and the organic layer was evaporated to get yield 3.3 g (85%) product, which was used without purification and was confirmed by NMR.

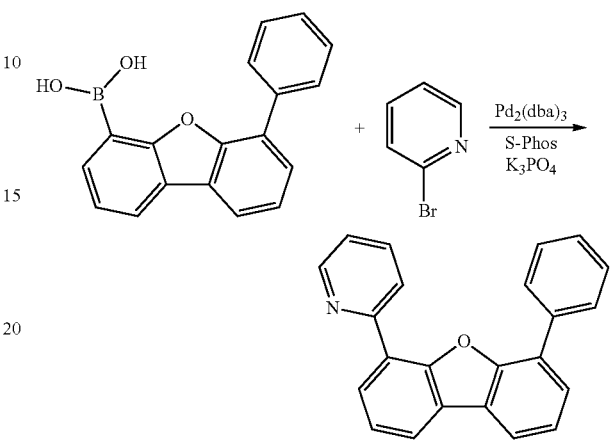

Synthesis of 2-(6-phenyldibenzo[b,d]furan-4-yl)pyridine: (6-phenyldibenzo[b,d]furan-4-yl)boronic acid (3.3 g, 11.45 mmol) and potassium phosphate (6.63 g, 31.2 mmol) were dissolved in 150 mL of toluene and 15 ml of water. The reaction was purged with nitrogen for 20 minutes and then 2-bromopyridine (1.64 g, 10.4 mmol), Pd$_2$(dba)$_3$ (0.2 g, 0.208 mmol) and S-Phos (0.342 g, 0.833 mmol) were added. The reaction was refluxed for 18 h. After cooling, 50 mL of water was added, the organic and aqueous layers were separated, and the aqueous layer was extracted twice with 100 mL of ethyl acetate. The organic layers were passed through a plug of silica gel. After evaporation of the solvent, the crude product was subjected to column chromatography to get 2.5 g (75%) pure product.

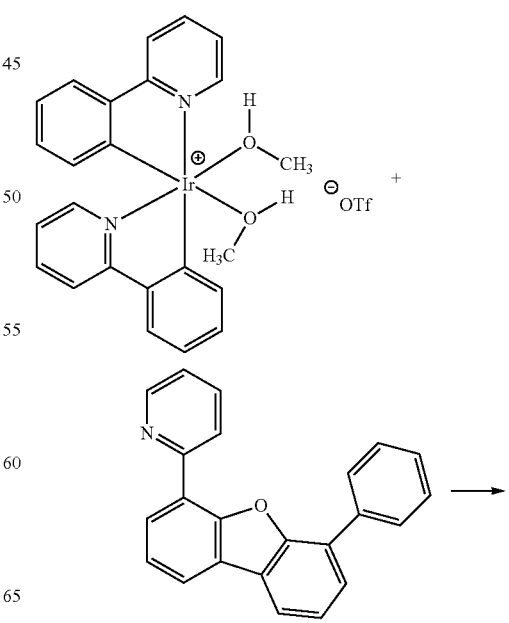

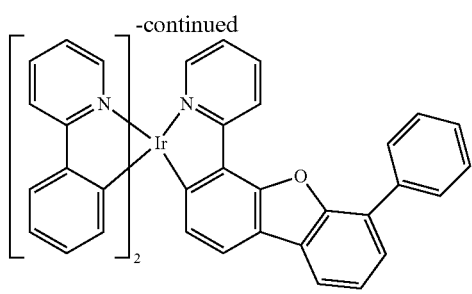

Synthesis of Compound 3: A mixture of iridium trifluoromethanesulfonate complex (1.5 g, 2.0 mmol) and 2-(6-phenyldibenzo[b,d]furan-4-yl)pyridine (2.0 g, 6.22 mmol) in EtOH 50 mL was refluxed for 48 hours under nitrogen atmosphere. The reaction mixture was cooled to room temperature and diluted with ethanol. Celite® was added and the mixture was stirred for 10 minutes. The mixture was filtered on a small silica gel plug and washed with ethanol (3-4 times) and with hexane (3-4 times). The filtrate was discarded. The Celite®/silica plug was then washed with dichloromethane to elute the product. The crude product was chromatographed on silica gel with 60% DCM in hexane (v/v) to yield 1.5 g (88%) of Compound 3, which was confirmed by LC/MS.

Synthesis of Compound 4

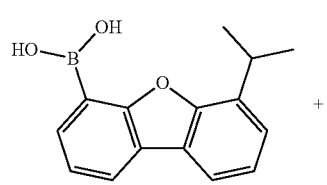

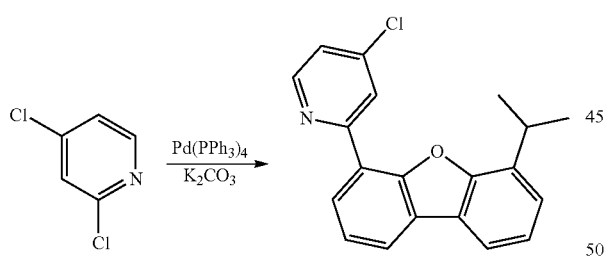

Synthesis of 2-(6-isopropyldibenzo[b,d]furan-4-yl)-4-chloropyridine: (6-isopropylldibenzo[b,d]furan-4-yl)boronic acid (12 g, 47.2 mmol) and potassium carbonate (19.58 g, 142 mmol) were dissolved in 100 mL DME and 100 mL of water. The reaction was purged with nitrogen for 20 minutes and then 2,4-dichloropyridine (5.61 mL, 52 mmol), Pd(PPh$_3$)$_4$ (1.637 g, 1.417 mmol) were added. The reaction was refluxed for 5 hours. After cooling the reaction back to room temperature, the organic and aqueous layers were separated, and the aqueous layer was extracted twice with 100 mL of ethyl acetate. After evaporation of the solvent, the crude product was subjected to column chromatography (SiO$_2$, 30-60% DCM in hexane, v/v) to yield 10.5 g (70%) pure product.

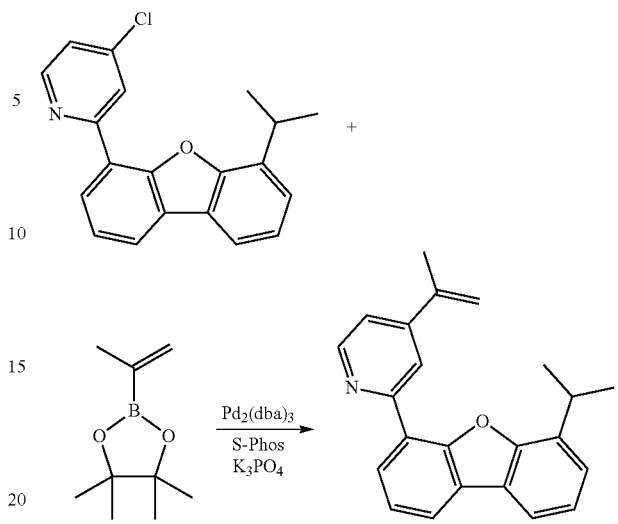

Synthesis of 2-(6-isopropyldibenzo[b,d]furan-4-yl)-4-(prop-1-en-2-yl)pyridine: 4-chloro-2-(6-isopropyldibenzo[b,d]furan-4-yl)pyridine (10.5 g, 32.6 mmol) and potassium phosphate (22.54 g, 98 mmol) were dissolved in 500 mL of toluene and 50 mL of water. The reaction was purged with nitrogen for 20 minutes and then 4,4,5,5-tetramethyl-2-(prop-1-en-2-yl)-1,3,2-dioxaborolane (6.13 mL, 32.6 mmol), Pd$_2$(dba)$_3$ (0.598 g, 0.653 mmol) and dicyclohexyl(2',6'-dimethoxy-[1,1'-biphenyl]-2-yl)phosphine (1.072 g, 2.61 mmol) were added. The reaction was refluxed for 18 hours. After cooling the reaction to room temperature, 100 mL of water was added to the reaction mixture. The aqueous layer was extracted twice with 100 mL of ethyl acetate. The organic layer was passed through a plug of silica gel, eluting with DCM. After evaporation of the solvent, the crude product was subjected to column chromatography (SiO$_2$, 3% ethyl acetate in hexane to 5% ethyl acetate in hexane, v/v) to yield 6.3 g (60.1%) of pure product.

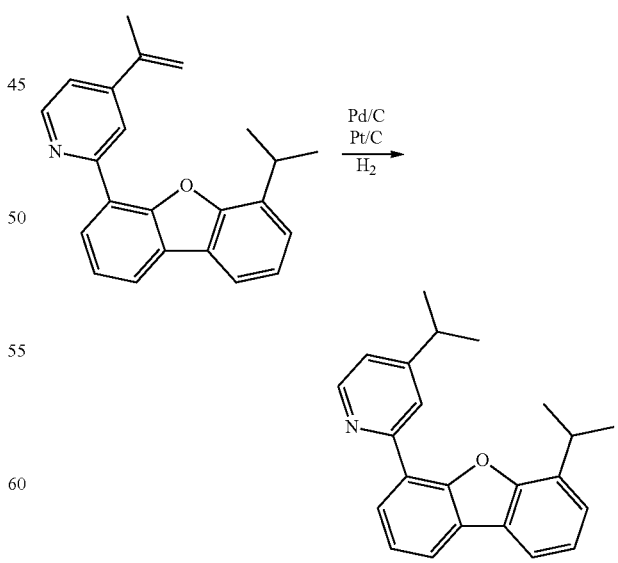

Synthesis of 4-isopropyl-2-(6-isopropyldibenzo[b,d]furan-4-yl)pyridine: 2-(6-isopropyldibenzo[b,d]furan-4-yl)-4-(prop-1-en-2-yl)pyridine (8.33 g, 25.4 mmol) was added to a hydrogenator bottle with EtOH (100 mL). The reaction mixture was degassed by bubbling $N_2$ for 10 minutes. Pd/C (0.812 g, 0.763 mmol) and Pt/C (1.489 g, 0.382 mmol) were added. The reaction mixture was placed on the Parr hydrogenator for 2 hours. The reaction mixture was filtered on a tightly packed Celite® bed and washed with dichloromethane. The crude product was chromatographed on silica gel with 2% DCM in hexane (v/v) and yielded 7.2 g (87%) of the desired pure product, which was confirmed by GC/MS.

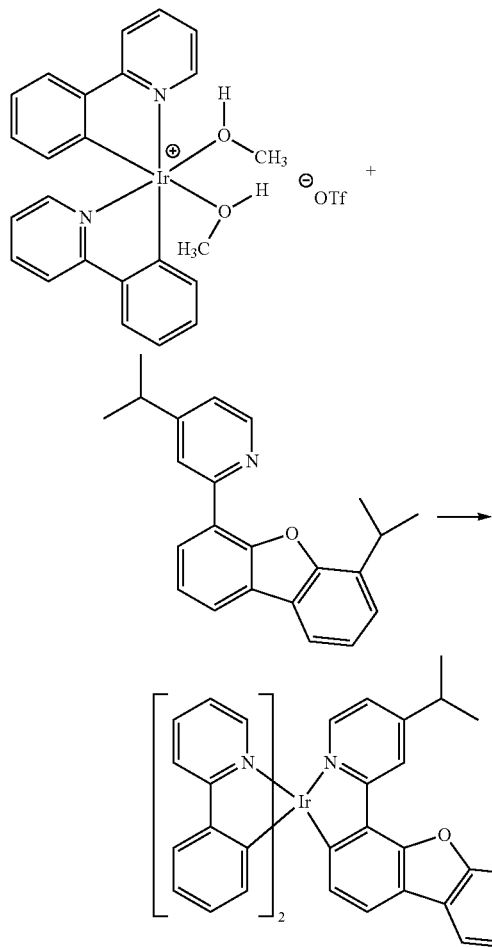

Synthesis of Compound 4: A mixture of iridium trifluoromethanesulfonate complex (2.5 g, 3.44 mmol) and 4-isopropyl-2-(6-isopropyldibenzo[b,d]furan-4-yl)pyridine (3.39 g, 10.31 mmol) in EtOH (25 mL) and MeOH (25 mL) was refluxed for 20 hours under nitrogen atmosphere. The reaction mixture was cooled back to room temperature, diluted with ethanol. Celite® was added to the mixture with stirring for 10 minutes. The mixture was filtered on a small silica gel plug and washed with ethanol (3-4 times) and with hexane (3-4 times). The filtrate was discarded. The Celite®/silica plug was then washed with dichloromethane to elute the product. The crude product was chromatographed on silica gel (pre-treated with 20% triethylamine in hexane) with 40% to 100 DCM in hexane (v/v). The product was crystallized from DCM/hexane and then sublimed to yield 1.37 g (48%) of Compound 4 was obtained after sublimation.

Synthesis of Compound 5

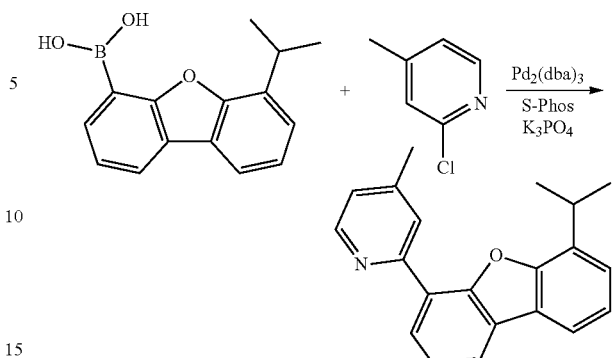

Synthesis of 2-(6-isopropyldibenzo[b,d]furan-4-yl)-4-methylpyridine: (6-Isopropyldibenzo[b,d]furan-4-yl)boronic acid (5.5 g, 21.65 mmol) and potassium phosphate (11.25 g, 64.9 mmol) were dissolved in 80 mL of toluene and 8 mL of water. The reaction was purged with nitrogen for 20 minutes and then 2-chloropyridine (2.418 ml, 21.65 mmol), $Pd_2(dba)_3$ (0.595 g, 0.649 mmol) and S-Phos (0.8 g, 1.948 mmol) were added. The reaction was refluxed for 18 hours. After cooling the reaction back to room temperature, 50 mL of water was added into reaction mixture. The aqueous layer was extracted twice with 100 mL of DCM. The organic layers were passed through a plug of silica gel, eluting with DCM. After evaporation of the solvent, the crude product was subjected to column chromatography ($SiO_2$, 5% ethyl acetate in hexane to 10% ethyl acetate in hexane, v/v) to yield 4.3 g (66%) pure product.

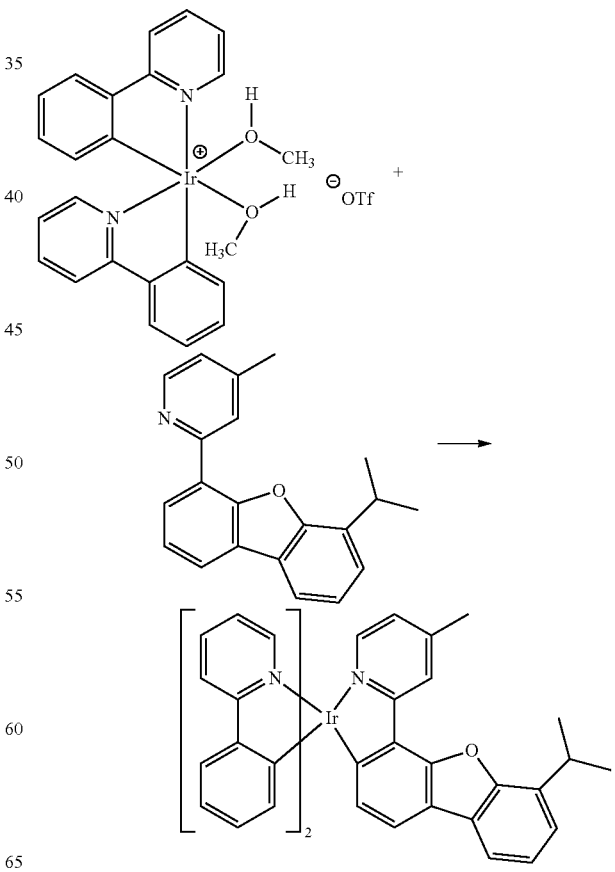

Synthesis of Compound 5: A mixture of iridium trifluoromethanesulfonate complex (1.5 g, 2.06 mmol) and 2-phenylpyridine (3 g, 6.18 mmol) in EtOH (25 mL) and MeOH (25 mL) was refluxed for 20 hours under nitrogen atmosphere. The reaction mixture was cooled to room temperature, diluted with ethanol, Celite® was added and the mixture stirred for 10 minutes. The mixture was filtered on a small silica gel plug and washed with ethanol (3-4 times) and with hexane (3-4 times). The filtrate was discarded. The Celite®/silica plug was then washed with dichloromethane to elute the product. The crude product was chromatographed on silica gel with 70% dichloromethane in hexane (v/v) to yield 0.45 g (28%) of desired product, which was confirmed by LC/MS.

Synthesis of Compound 6

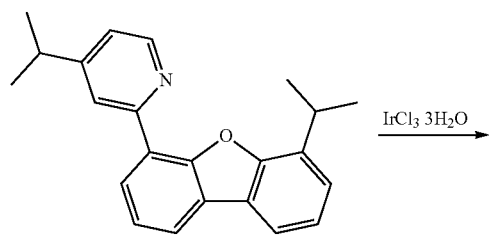

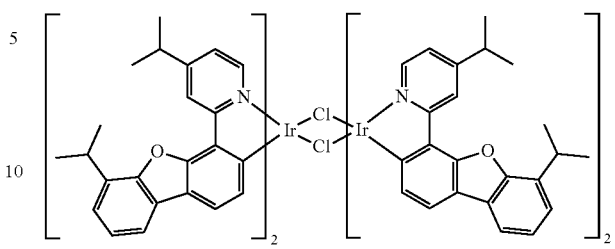

Synthesis of chloro-bridged dimer: 2-(6-Isopropyldibenzo[b,d]furan-4-yl)-4-isopropylpyridine (3.27 g, 9.92 mmol) and iridium(III) chloride (1.66 g, 3.31 mmol) were placed in a 200 mL flask containing 2-ethoxyethanol (45 mL) and water (15 mL) under a nitrogen atmosphere. The resulting reaction mixture was refluxed at 130° C. for 18 hours. After cooling back to room temperature, this reaction mixture was filtered and washed with 3× methanol followed by 3× hexane. The product obtained was dried under vacuum to yield 2.5 g (60%) of the desired product.

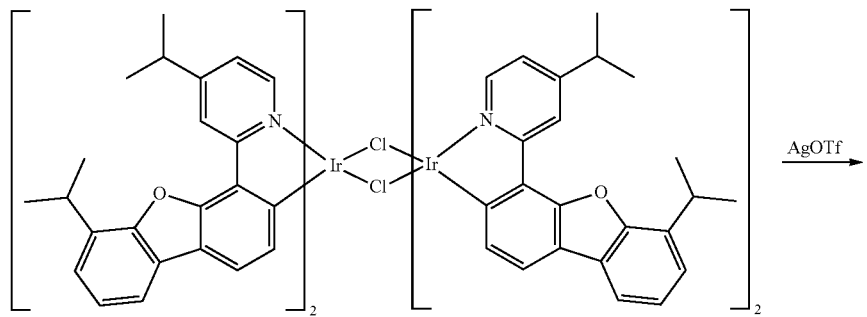

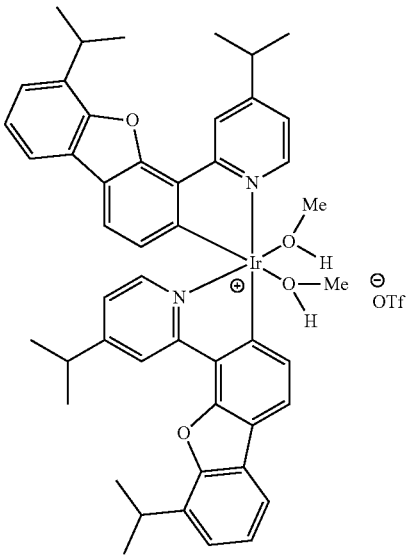

Synthesis of iridium trifluoromethanesulfonate salt: The iridium dimer (2.5 g, 1.41 mmol) was dissolved in 300 mL of dichloromethane. In a separate flask, silver (I) trifluoromethanesulfonate (0.799 g, 3.11 mmol) was dissolved in MeOH (150 mL) and added slowly to the dichloromethane solution with continuous stirring at room temperature overnight in the dark. The reaction mixture was filtered through silica gel which was topped with a tightly packed Celite® bed. The product was obtained as a dark yellow solid after removal of solvent, yielding 2.5 g (78%) and used without further purification.

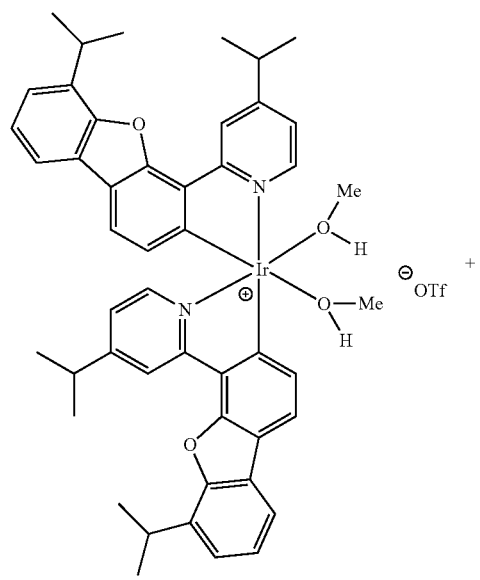

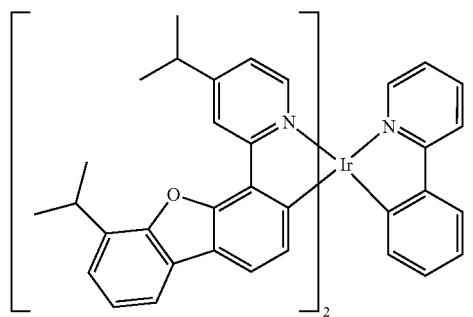

Synthesis of Compound 6: A mixture of iridium trifluoromethanesulfonate complex (2.5 g, 2.01 mmol) and 2-phenylpyridine (0.862 g, 6.03 mmol) in EtOH (25 mL) and MeOH (25 mL) was refluxed for 20 hours under nitrogen atmosphere. The reaction mixture was cooled back to room temperature and diluted with ethanol. Celite® was added to the mixture and it was stirred for 10 minutes, and then filtered on a small silica gel plug and washed with ethanol (3-4 times) and hexane (3-4 times). The filtrate was discarded. The Celite®/silica plug was then washed with dichloromethane to elute the product. The crude product was chromatographed on silica gel (pre-treated with 20% triethylamine in hexane) with 40% DCM in hexane (v/v) to yield 0.8 g (40%) of Compound 6, which was confirmed by LC-MS.

Synthesis of Compound 7

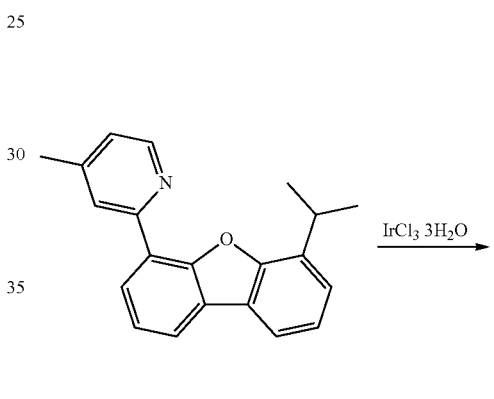

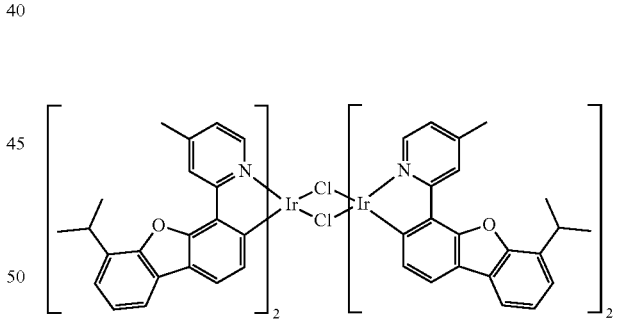

Synthesis of chloro-bridged dimer: 2-(6-isopropyldibenzo[b,d]furan-4-yl)-4-methylpyridine (2.1 g, 6.97 mmol) and iridium(III) chloride (1.229 g, 3.48 mmol) were placed in a 200 mL flask to which was added 2-ethoxyethanol (45 mL) and water (15 mL) under a nitrogen atmosphere. The resulting reaction mixture was refluxed at 130° C. for 18 hours. After cooling back to room temperature, this reaction mixture was filtered and washed with 3× methanol and 3× hexane. The product obtained was dried under vacuum to yield 2.9 g (70.1%) of the desired product for next step reaction.

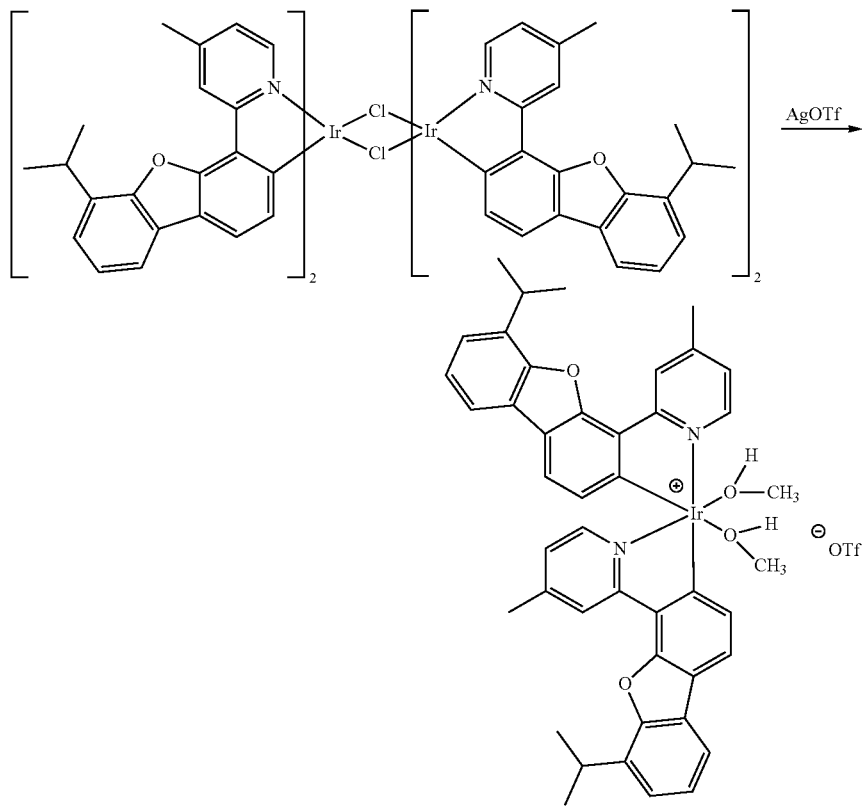

Synthesis of iridium trifluoromethanesulfonate salt: The iridium dimer (2.9 g, 1.75 mmol) was dissolved in 300 mL of dichloromethane. In a separate flask, silver (I) trifluoromethanesulfonate (0.944 g, 3.36 mmol) was dissolved in MeOH (150 mL) and added slowly to the dichloromethane solution with continuous stirring at room temperature for 7 hours in the dark. The reaction mixture was filtered through silica gel topped with a tightly packed Celite® bed and the solvent was removed under vacuum to yield 3.1 g (80.1%) of product as a dark yellow solid. The product was used without further purification.

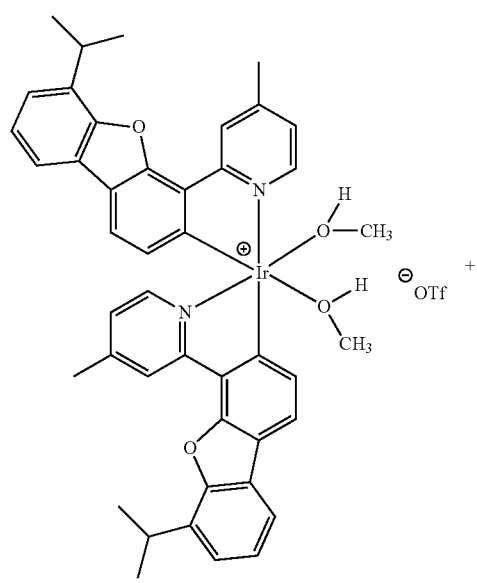

-continued

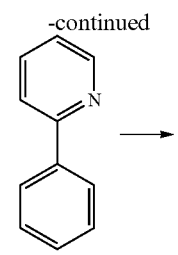

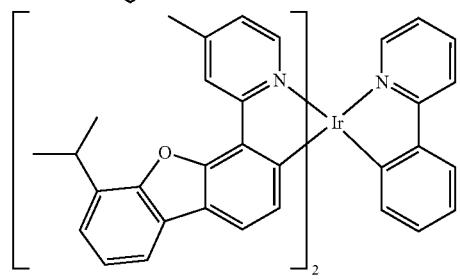

Synthesis of Compound 7: A mixture of iridium trifluoromethanesulfonate complex (3.0 g, 2.99 mmol) and 2-phenylpyridine (1.85 g, 11.95 mmol) in EtOH (25 mL) and MeOH (25 mL) were refluxed for 20 hours under nitrogen atmosphere. The reaction mixture was cooled back to room temperature, diluted with ethanol, and Celite® was added. The mixture was stirred for 10 minutes and was filtered on a small silica gel plug and washed with ethanol (3-4 times) and hexane (3-4 times). The filtrate was discarded. The Celite®/silica plug was then washed with dichloromethane to elute the product. The crude product was chromatographed on silica gel (pre-treated with 20% triethylamine in hexane) with 30% DCM in hexane (v/v) to yield 1 g (35.3%) of Compound 7, which was confirmed by LC-MS.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A compound having the formula:

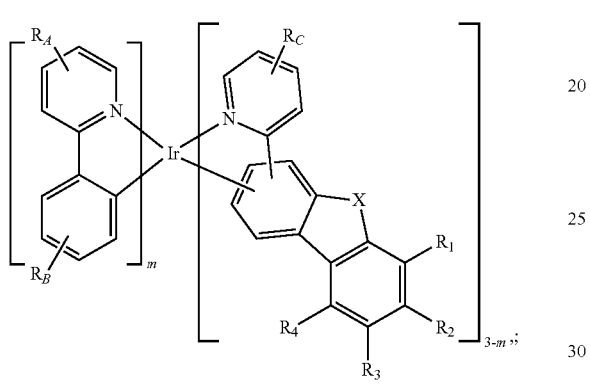

Formula I wherein $R_1$ is alkyl or cycloalkyl;

wherein $R_2$, $R_3$, $R_4$, $R_A$, $R_B$, and $R_C$, are independently selected from the group consisting of hydrogen, deuterium, alkyl, cycloalkyl, aryl, heteroaryl, and combinations thereof;

wherein $R_A$, $R_B$, and $R_C$ may represent mono, di, tri, or tetra substitutions;

wherein two adjacent substituents $R_1$, $R_2$, $R_3$, $R_4$, $R_A$, and $R_C$ are optionally joined to form a fused ring;

wherein X is selected from the group consisting of O, S, and Se; and wherein m is 1 or 2.

2. The compound of claim 1, wherein $R_C$ is alkyl.

3. The compound of claim 2, wherein $R_A$ and $R_B$ are hydrogen.

4. The compound of claim 1, wherein $R_3$ is alkyl.

5. The compound of claim 1, wherein $R_C$ and $R_3$ are alkyl.

6. The compound of claim 1, wherein X is O.

7. The compound of claim 1, wherein m is 2.

8. The compound of claim 1, wherein $R_C$ represents monoalkyl substitution and $R_C$ is para to N.

9. The compound of claim 1, wherein $R_1$ is methyl or $CH(CH_3)_2$; and $R_2$, $R_3$, and $R_4$ are independently selected from the group consisting of methyl, $CH(CH_3)_2$, and phenyl.

10. The compound of claim 1, wherein $R_2$, $R_3$, and $R_4$ are independently selected from the group consisting of alkyl, hydrogen, and deuterium.

11. The compound of claim 1, wherein the compound has a sublimation temperature from about 180° C. to about 240° C. at pressure ranging from $10^{-7}$ to $10^{-8}$ torr.

12. The compound of claim 1, having the formula:

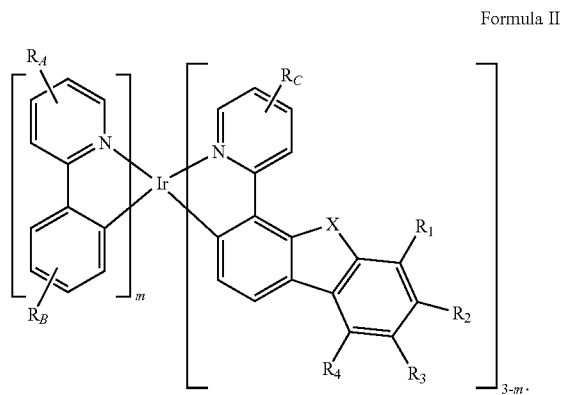

Formula II

13. A first device comprising a first organic light emitting device, comprising:
an anode;
a cathode; and
an organic layer, disposed between the anode and the cathode, comprising a compound having the formula:

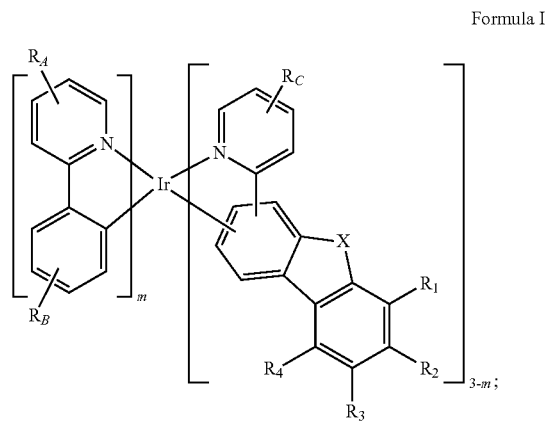

Formula I wherein $R_1$ is alkyl or cycloalkyl;

wherein $R_2$, $R_3$, $R_4$, $R_A$, $R_B$, and $R_C$, are independently selected from the group consisting of hydrogen, deuterium, alkyl, cycloalkyl, aryl, heteroaryl, and combinations thereof;

wherein $R_A$, $R_B$, and $R_C$ may represent mono, di, tri, or tetra substitutions;

wherein two adjacent substituents $R_1$, $R_2$, $R_3$, $R_4$, $R_A$, and $R_C$ are optionally joined to form a fused ring;

wherein X is selected from the group consisting of O, S, and Se; and wherein m is 1 or 2.

14. The first device of claim 13, wherein the first device is a consumer product.

15. The first device of claim 13, wherein the first device is an organic light-emitting device.

16. The first device of claim 13, wherein the first device comprises a lighting panel.

17. The first device of claim 13, wherein the organic layer is an emissive layer and the compound is a non-emissive dopant.

18. The first device of claim 13, wherein the organic layer further comprises a host.

19. The first device of claim 18, wherein the host comprises a triphenylene containing benzo-fused thiophene or benzo-fused furan;

wherein the host is, optionally, further substituted by an unfused substituent independently selected from the group consisting of $C_nH_{2n+1}$, $OC_nH_{2n+1}$, $OAr_1$, $N(C_nH_{2+1})_2$, $N(Ar_1)(Ar_2)$, $CH=CH-C_nH_{2n+1}$, $C\equiv CC_nH_{2n+1}$, $Ar_1$, $Ar_1-Ar_2$, and $C_nH_{2n}-Ar_1$;

wherein n is from 1 to 10; and wherein $Ar_1$ and $Ar_2$ are independently selected from the group consisting of benzene, biphenyl, naphthalene, triphenylene, carbazole, and heteroaromatic analogs thereof.

20. The first device of claim 19, wherein the host has the formula:

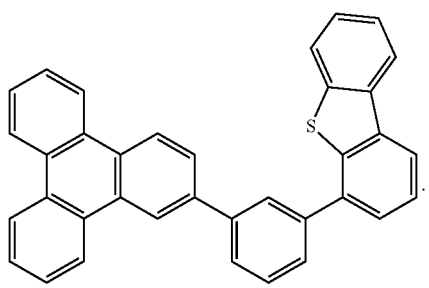 [SMILES: c1cc(-c2ccc3c4ccccc4c4ccccc4c3c2)cc(-c2cccc3c2sc2ccccc23)c1]

21. The first device of claim 18, wherein the host is selected from the group consisting of:

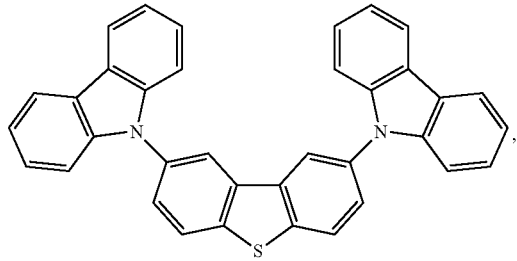

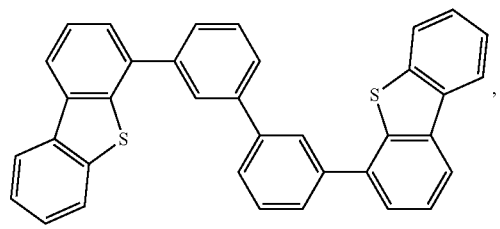

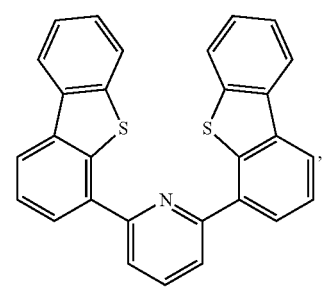

-continued

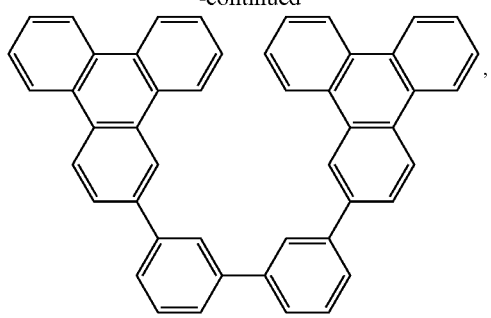

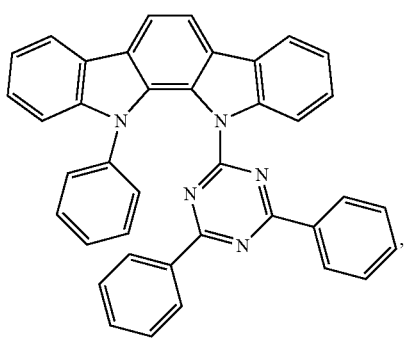

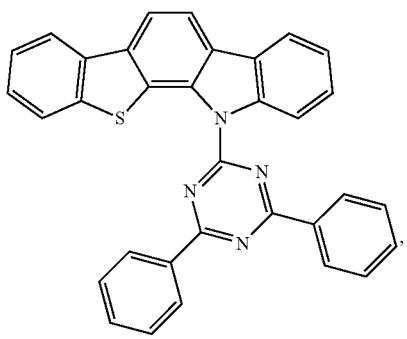

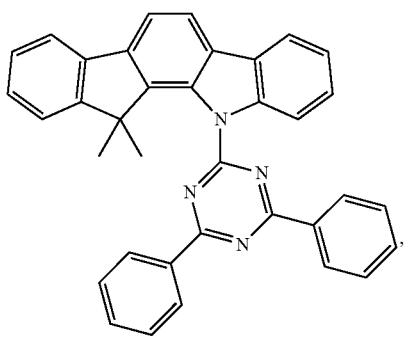

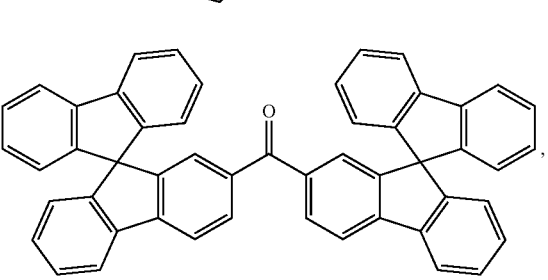

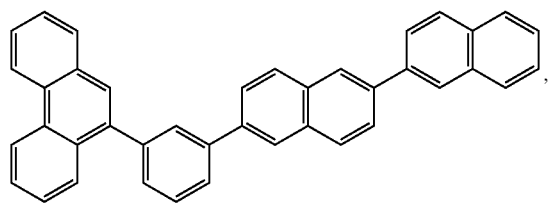
and combinations thereof.
22. The first device of claim 18, wherein the host is a metal complex.
23. The compound of claim 1, wherein the compound is selected from the group consisting of:
Compound 1
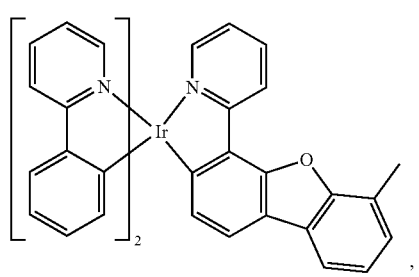
Compound 2
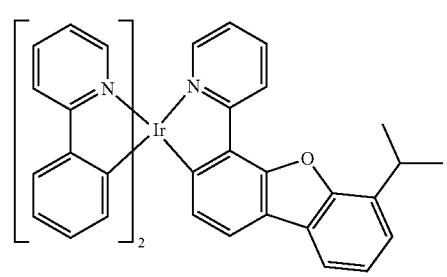
Compound 4
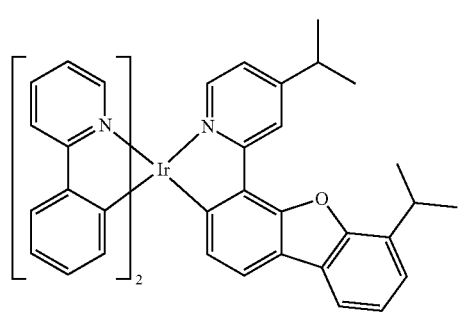
Compound 5
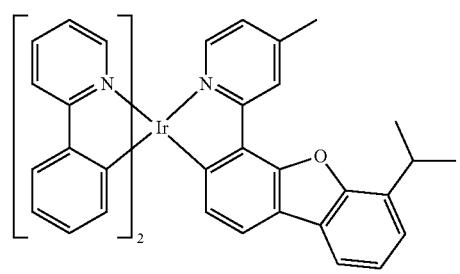
Compound 6
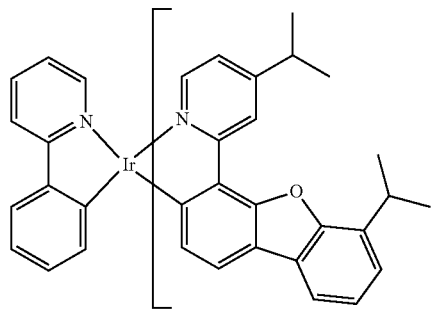
Compound 7
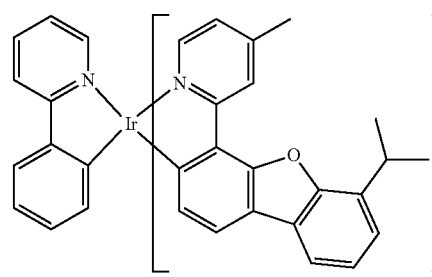
Compound 8
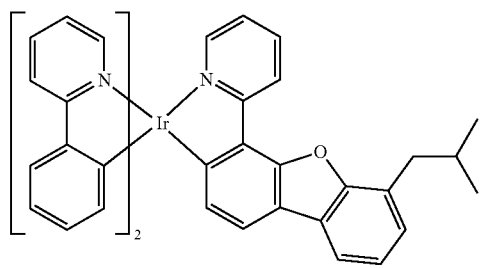
Compound 9
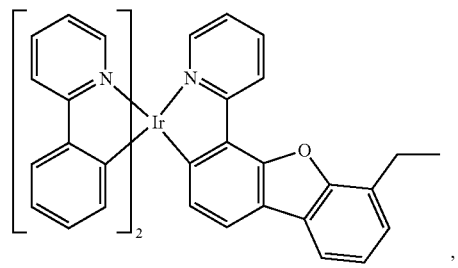
Compound 10
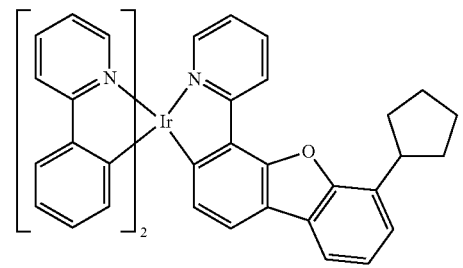

Compound 21
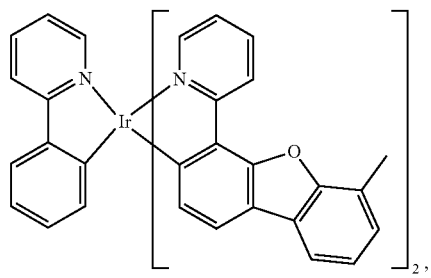
Compound 22
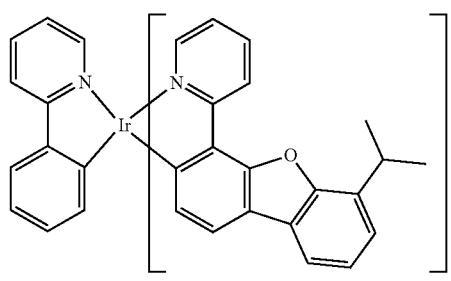
Compound 23
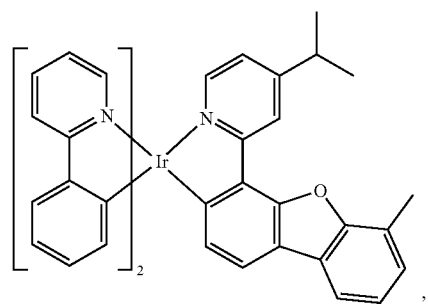
Compound 24
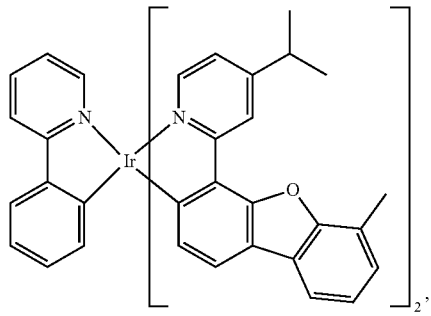
Compound 27
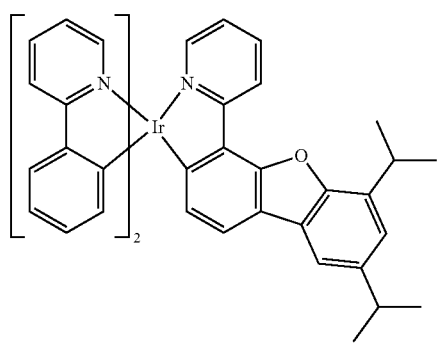
Compound 28
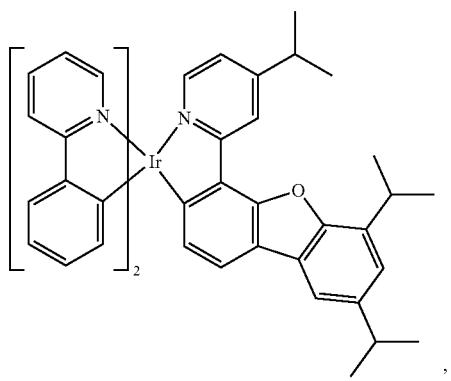
Compound 29
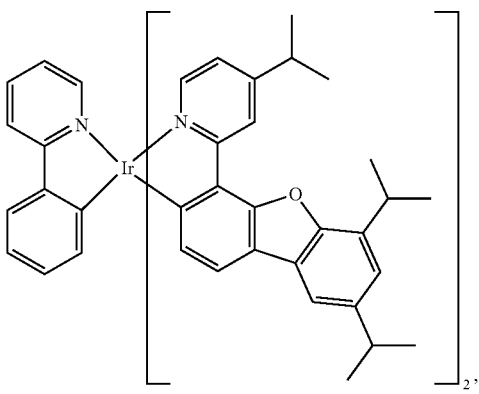
Compound 30
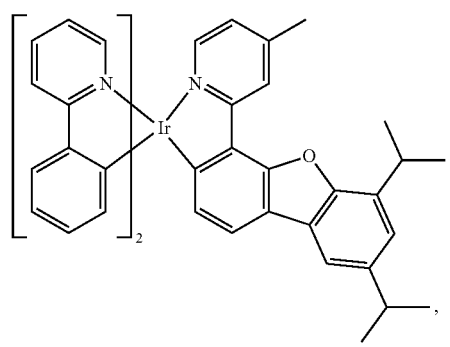
Compound 31
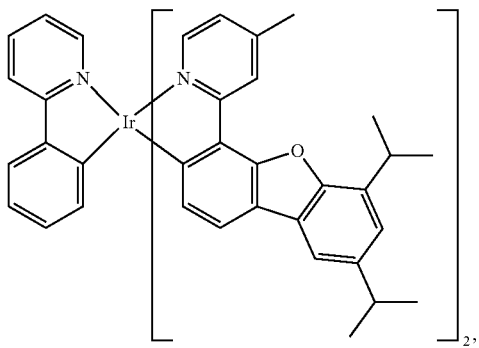

-continued
Compound 32
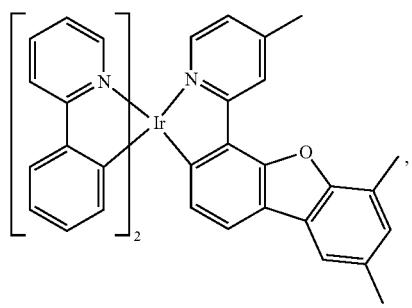
Compound 33
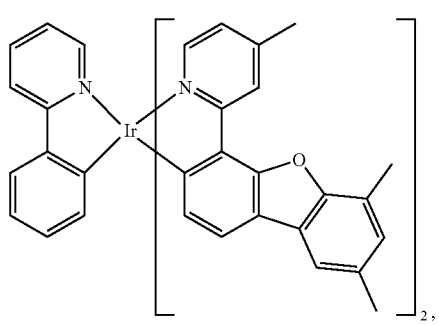
Compound 34
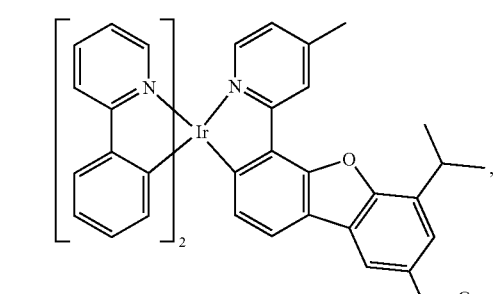
Compound 35
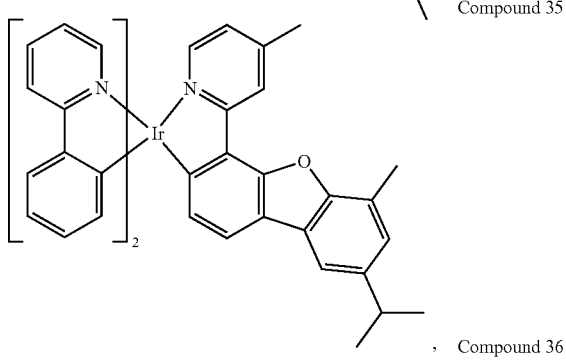
Compound 36
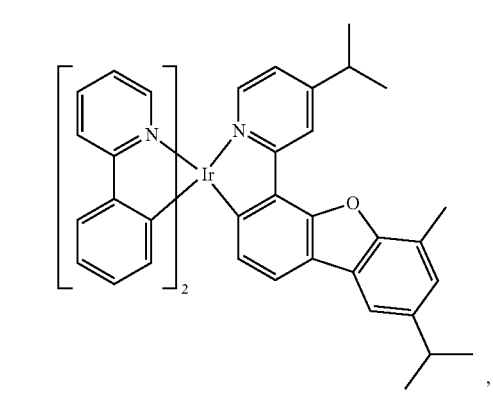
-continued
Compound 37
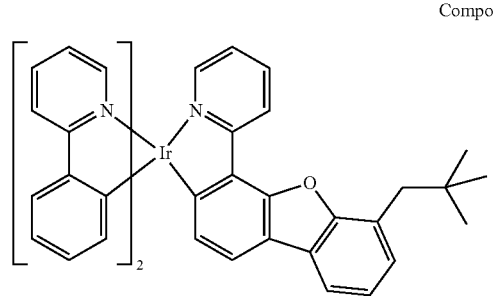
Compound 38
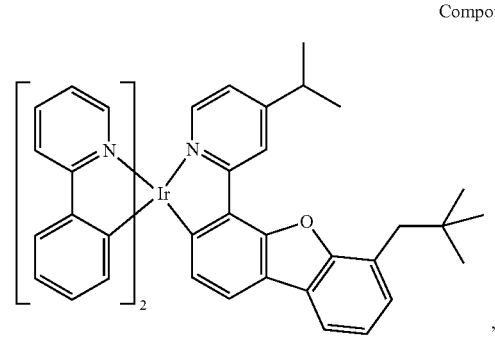
Compound 41
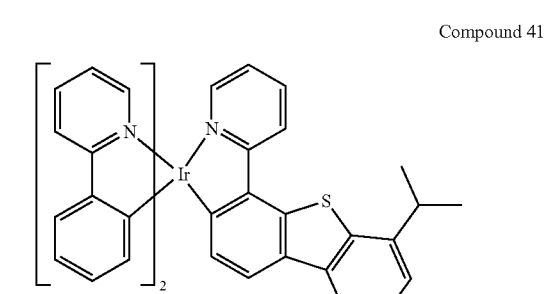
Compound 42
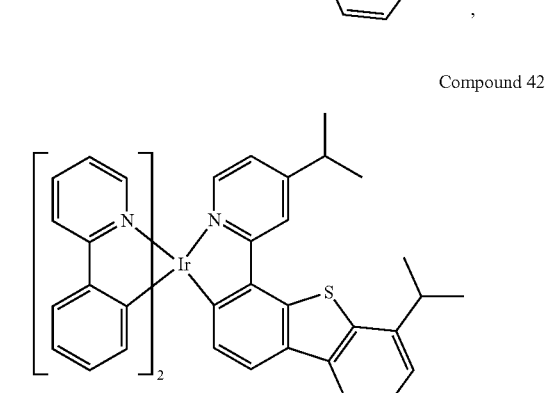
Compound 43
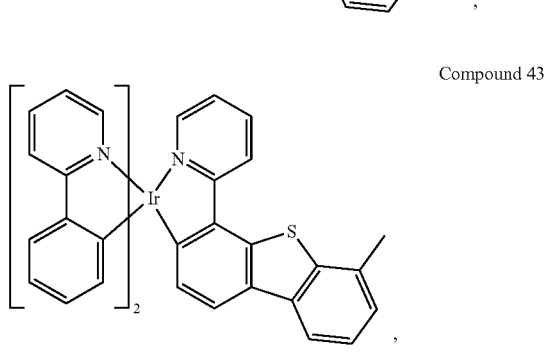

Compound 44
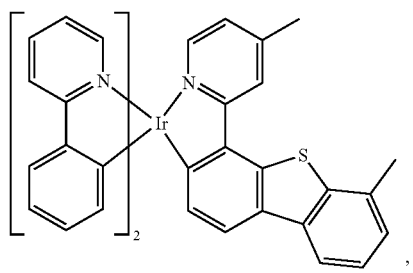
Compound 45
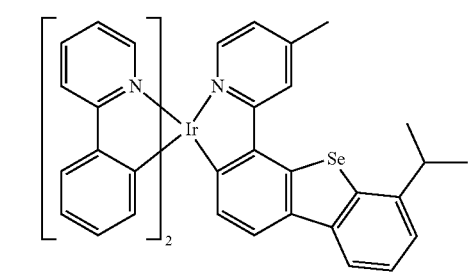
Compound 46
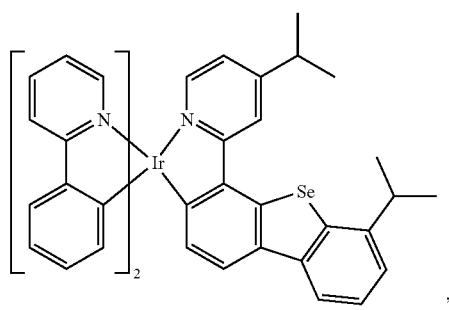
Compound 47
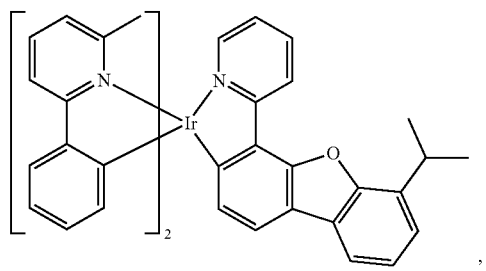
Compound 48
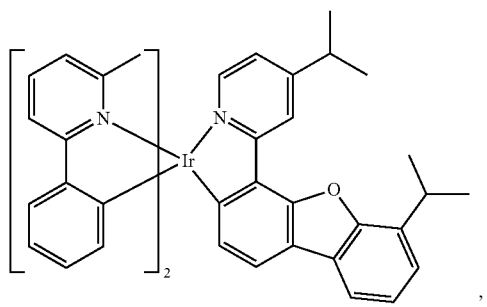
Compound 49
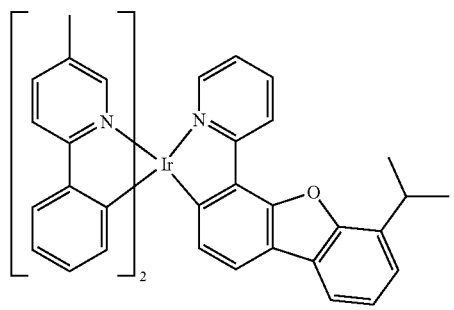
Compound 50
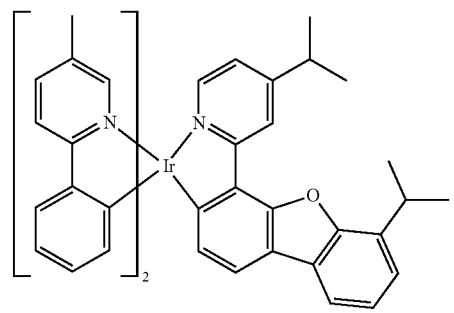
Compound 51
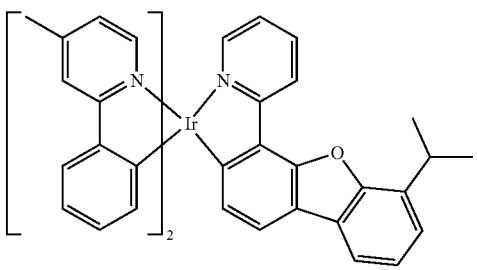
Compound 52
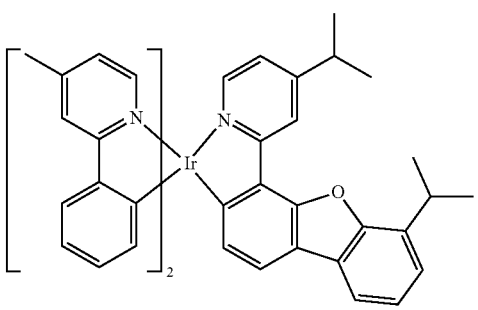
Compound 53
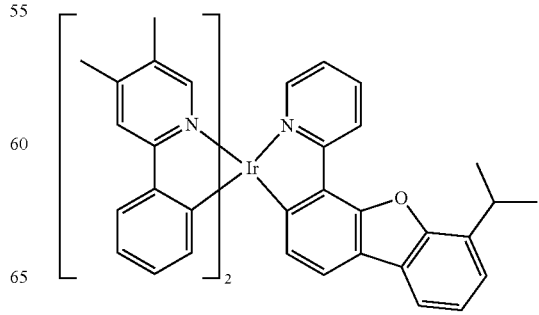
and Compound 54
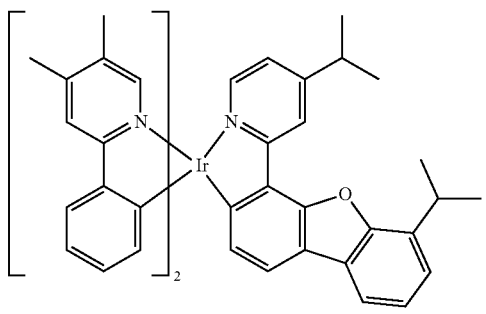
24. The compound of claim 1, wherein the compound is selected from the group consisting of:
Compound 55
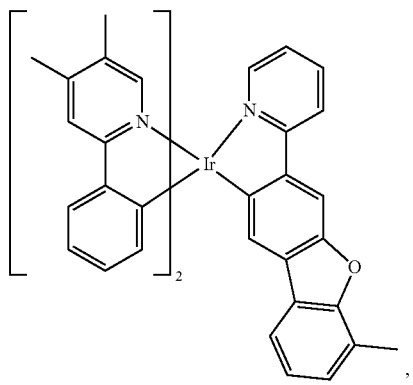
Compound 56
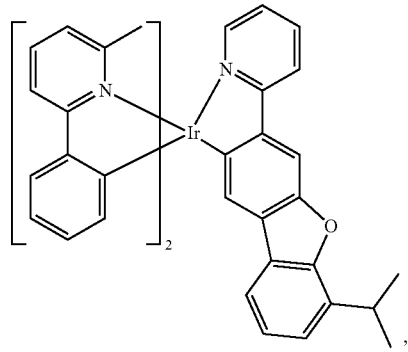
Compound 59
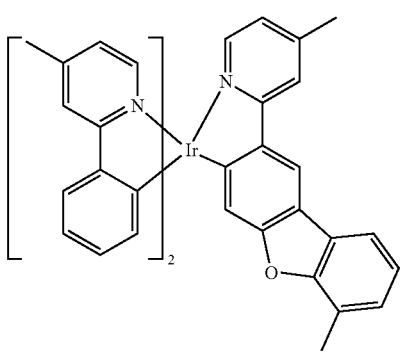
Compound 60
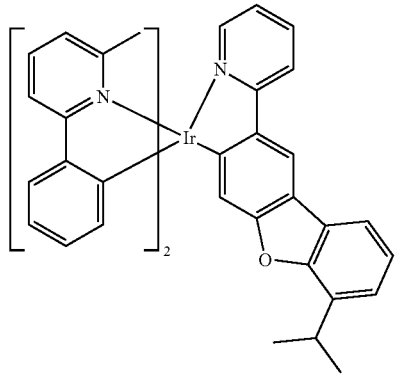
Compound 62
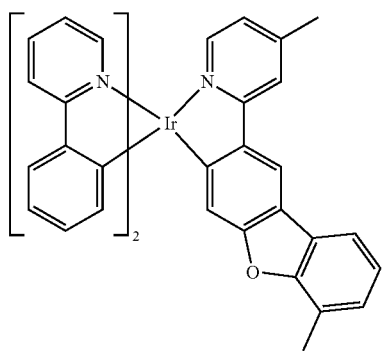
, and
Compound 63
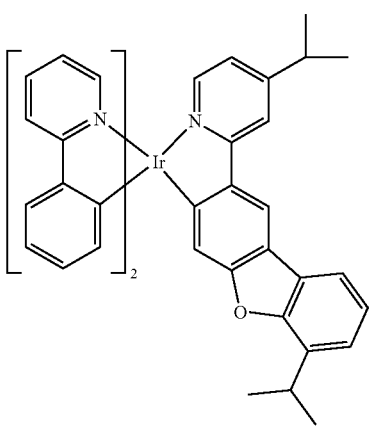
25. The compound of claim 1, wherein $R_2$, $R_3$, and $R_4$ are hydrogen or deuterium.
* * * * *

UNITED STATES PATENT AND TRADEMARK OFFICE
CERTIFICATE OF CORRECTION

PATENT NO. : 9,193,745 B2
APPLICATION NO. : 13/296806
DATED : November 24, 2015
INVENTOR(S) : Bin Ma et al.

It is certified that error appears in the above-identified patent and that said Letters Patent is hereby corrected as shown below:

In the Specification:
In Column 20, lines 27-37 delete

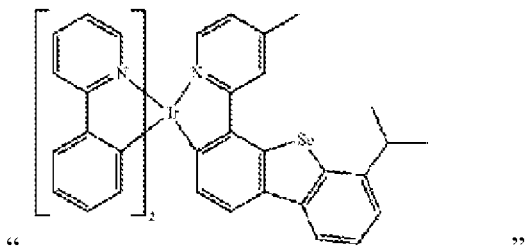

" "

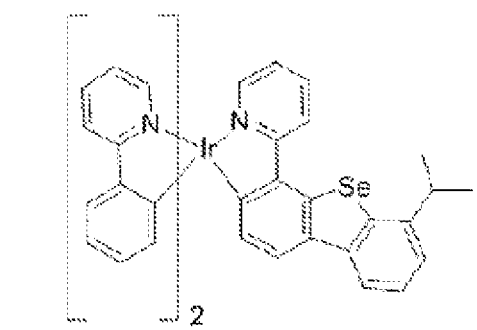

and insert -- Compound 45 --

Signed and Sealed this
Sixteenth Day of August, 2016

Michelle K. Lee
*Director of the United States Patent and Trademark Office*

CERTIFICATE OF CORRECTION (continued)
U.S. Pat. No. 9,193,745 B2

In the Claims:
In Claim 23, Column 139, lines 12-25 delete

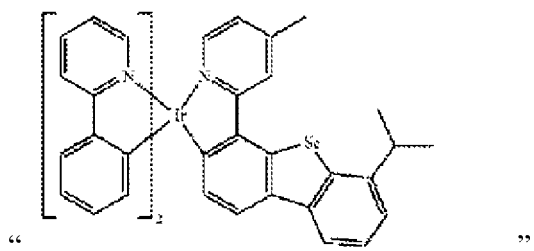

" "

and insert -- 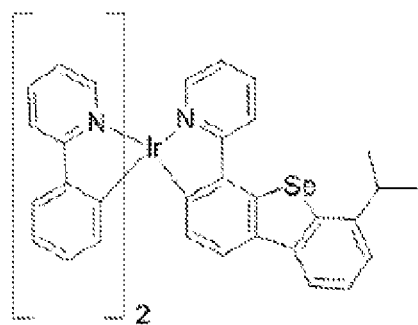 Compound 45 --